(12) United States Patent
Brautaset et al.

(10) Patent No.: US 9,322,000 B2
(45) Date of Patent: Apr. 26, 2016

(54) **METHANOL DEHYDROGENASE ENZYMES FROM *BACILLUS***

(71) Applicants: Sinvent AS, Trondheim (NO); Rijksuniversiteit Groningen, CP Groningen (NL); ETH Zurich, Zurich (CH)

(72) Inventors: Trygve Brautaset, Trondheim (NO); Tonje Marita Bjerkan Heggeset, Trondheim (NO); Anne Krog, Trondheim (NO); Wilhelmus Johannes Quax, AV Groningen (NL); Mark Jan Jacobus Bernhard Sibbald, AV Groningen (NL); Julia Vorholt, Zürich (CH); Jonas Müller, Zürich (CH); Patrick Kiefer, Zürich (CH); Eva Potthoff, Zürich (CH); Volker F Wendisch, Bielefeld (DE); Lennart Lessmeier, Bielefeld (DE); Stéphanie Heux, Balma (FR); Jean-Charles Portais, Pibrac (FR)

(73) Assignees: SINTEF TTO AS, Sluppen (NO); ETH ZURICH, Zurich (CH); RIJKSUNIVERSITEIT GRONINGEN, CP Groningen (NL)

(*) Notice: Subject to any disclaimer, the term of this patent is extended or adjusted under 35 U.S.C. 154(b) by 0 days.

(21) Appl. No.: 14/374,878

(22) PCT Filed: Jan. 25, 2013

(86) PCT No.: PCT/EP2013/051516
§ 371 (c)(1),
(2) Date: Jul. 25, 2014

(87) PCT Pub. No.: WO2013/110797
PCT Pub. Date: Aug. 1, 2013

(65) Prior Publication Data
US 2015/0267177 A1 Sep. 24, 2015

(30) Foreign Application Priority Data
Jan. 25, 2012 (GB) .................................. 1201178.9

(51) Int. Cl.
*C12N 9/04* (2006.01)
(52) U.S. Cl.
CPC ....... *C12N 9/0006* (2013.01); *C12Y 101/01244* (2013.01)
(58) Field of Classification Search
CPC .................................................... C12N 9/0006
USPC ..................... 435/183, 252.3, 320.1; 530/350
See application file for complete search history.

(56) References Cited

U.S. PATENT DOCUMENTS 6,261,825 B1 7/2001 Hanson et al.
6,331,428 B1 12/2001 Kato
7,163,810 B2 1/2007 Yasueda et al.
2004/0142435 A1 7/2004 Gunji et al.

FOREIGN PATENT DOCUMENTS

| DE | 10354024 A1 | 6/2004 |
|---|---|---|
| EP | 0984066 A2 | 3/2000 |
| EP | 1170371 A1 | 1/2002 |

(Continued)

OTHER PUBLICATIONS

International Search Report and Written Opinion of corresponding PCT/EP2013/051516, dated Apr. 8, 2013, 13 pages.
Brautaset, et al., "Plasmid-Dependent Methylotrophy in Thermotolerant *Bacillus methanolicus*", Journal of Bacteriology, vol. 186, No. 5, Mar. 2004, pp. 1229-1238, XP002694286.
Brautaset, et al., "*Bacillus methanolicus*: a candidate for industrial production of amino acids from methanol at 50° C.", Appl Microbiology Biotechnol vol. 74:22-34, No. 1, Jan. 11, 2007, pp. 22-34, XP019472575.
Heggeset, et al., "Genome Sequence of Thermotolerant *Bacillus methanolicus*: Features and Regulation Related to Methylotrophy and Production of $_L$-Lysine and $_L$-Glutamate from Methanol", Applied and Environmental Microbiology, vol. 78, No. 15. Aug. 2012, pp. 5170-5181, XP002694287.

(Continued)

*Primary Examiner* — Maryam Monshipouri
(74) *Attorney, Agent, or Firm* — Lewis Roca Rothgerber Christie LLP

(57) ABSTRACT

The present invention relates to a nucleic acid molecule, which encodes a polypeptide having alcohol dehydrogenase activity, in particular methanol dehydrogenase activity, comprising having a nucleotide sequence selected from the group consisting of: (i) a nucleotide sequence as set forth in any one of SEQ ID NOs: 1 (mdh2-MGA3), 3 (mdh3-MGA3), or 5 (mdh2-PB1); (ii) a nucleotide sequence having at least 90% sequence identity, more particularly at least 91, 92, 93, 94, 95, 96, 97, 98 or 99% sequence identity, with a nucleotide sequence as set forth in any one of SEQ ID NOs: 1, 3 or 5; (iii) a nucleotide sequence which is degenerate with any one of the nucleotide sequences of SEQ ID NOs: 1, 3 or 5; (iv) a nucleotide sequence which is a part of the nucleotide sequence of any one of SEQ ID NOs: 1, 3 or 5, or of a nucleotide sequence which is degenerate with a sequence of SEQ ID NOs: 1, 3 or 5; (v) a nucleotide sequence encoding all or part of a polypeptide whose amino acid sequence is set forth in any one of SEQ ID NOs: 2 (Mdh2-MGA3), 4 (Mdh3-MGA3) or 6 (Mdh2-PB1); and (vi) a nucleotide sequence encoding all or part of a polypeptide which has an amino acid sequence having at least 90% sequence identity, preferably at least 91, 92, 93, 94, 95, 96, 97, 98 or 99% sequence identity, with an amino acid sequence as set forth in any one of SEQ ID NOs: 2, 4 or 6; or a nucleic acid molecule comprising a nucleotide sequence which is complementary to the nucleotide sequence of any one of (i) to (vi). Also provided are recombinant constructs, vectors and host cells comprising such a nucleic acid molecule and polypeptides encoded thereby. Such molecules may advantageously be used in the genetic modification of host cells, for example to introduce or modify methanol dehydrogenase activity.

12 Claims, 18 Drawing Sheets

(56) References Cited

FOREIGN PATENT DOCUMENTS

Figure 7:
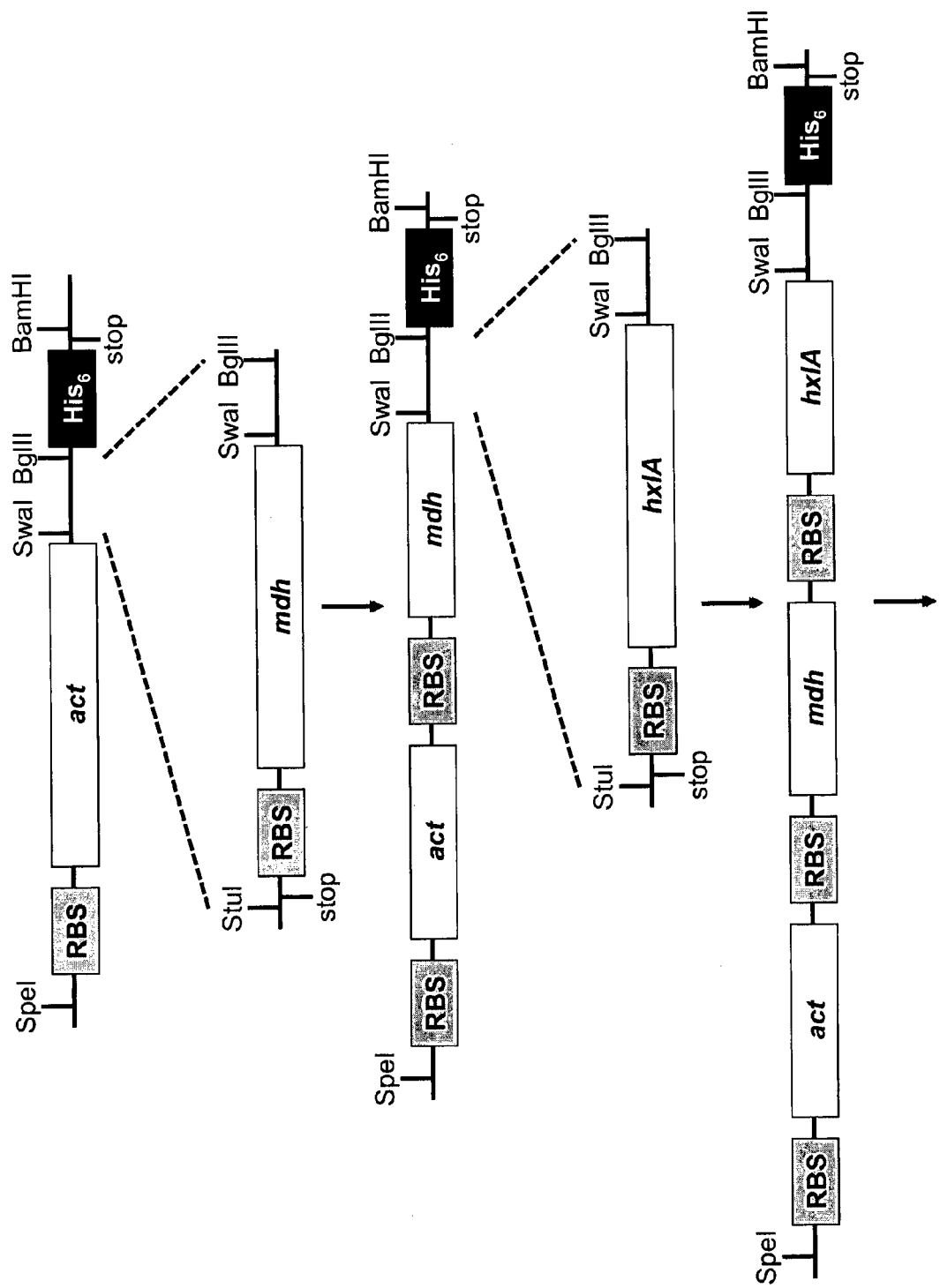

| | | |
|---|---|---|
| EP | 1266966 A2 | 12/2002 |
| EP | 1454991 A1 | 9/2004 |
| WO | WO 90/12105 | 10/1990 |
| WO | WO 00/20785 | 4/2000 |
| WO | WO 2011/011627 | 1/2011 |

OTHER PUBLICATIONS

Dijkhuizen, L., et al., "The Physiology and Biochemistry of Aerobic Methanol-Utilizing Gram-Negative and Gram Positive Bacteria", Methane and Methanol Utilizers, Plenum Press (1992), pp. 149-181.

Alber, Birgit E., "Biotechnological potential of the ethylmalonyl-CoA pathway", Appl. Microbiol Biotechnol., 2011, vol. 89, pp. 17-25.

Anthony, C., "The Biochemistry of Methylotrophs", Academic Press Inc., 1982, pp. 1-430.

Arfman, Nico, et al., "Properties of an NAD(H)-containing methanol dehydrogenase and its activator protein from *Bacillus methanolicus*", Eur. J. Biochem., 1997, vol. 244, pp. 426-433.

Arfman, N., et al., "Environmental regulation of alcohol metabolism in thermotolerant methylotrophic *Bacillus* strains", Archives of Microbiology, 1992, vol. 157, pp. 272-278.

Arfman, N., et al., "Methanol metabolism in thermotolerant methylotrophic *Bacillus* strains involving a novel catabolic NAD-dependent methanol dehydrogenase as a key enzyme", Archives of Microbiology, 1989, vol. 152, pp. 280-288.

Altschul, Stephen F., et al., "Gapped BLAST and PSI-BLAST: a new generation of protein database search programs", Nucleic Acids Research, 1997, vol. 25, No. 17, pp. 3389-3402.

Altschul, Stephen F., et al., "Basic Local Alignment Search Tool", J. Mol. Biol., 1990, vol. 215, pp. 403-410.

Arnold, Konstantin, et al., "The SWISS-MODEL workspace: a web-based environment for protein structure homology modelling", Bioinformatics, 2006, vol. 22, No. 2, 195-201.

Aziz, Ramy K., et al., "The RAST Server: Rapid Annotations using Subsystems Technology", BMC Geonomics, 2008, vol. 9, No. 75, pp. 1-15.

Brautaset, Trygve, et al., "*Bacillus methanolicus* pyruvate carboxylase and homoserine dehydrogenase I and II and their roles for $_L$-lysine production from methanol at 50° C.", Appl Microbiol Biotechnol, 2010, vol. 87, pp. 951-964.

Brautaset, Trygve, et al., "Role of the *Bacillus methanolicus* Citrate Synthase II Gene, *citY*, in Regulating the Secretion of Glutamate in $_L$-Lysine-Secreting Mutants", Applied and Environmental Microbiology, 2003, vol. 69, No. 7, pp. 3986-3995.

Bron, Sierd, et al., "Protein secretion and possible roles for multiple signal peptidases for precursor processing in Bacilli", Journal of Biotechnology, 1998, vol. 64, pp. 3-13.

Chao, Liu, et al., "Complete nucleotide sequence of pBMB67, a 67-kb plasmid from *Bacillus thuringiensis* strain YBT-1520", Plasmid, 2007, vol. 57, pp. 44-54.

Chistoserdova, Ludmila, "Modularity of methylotrophy, revisited", Environmental Microbiology, 2011, vol. 13, No. 10, pp. 2603-2622.

Chistoserdova, Ludmila, et al., "The Expanding World of Methylotrophic Metabolism", Annu. Rev. Miocrobiol., 2009, vol. 63, pp. 477-499.

Commichau, Fabian M., et al., "Regulatory links between carbon and nitrogen metabolism", Current Opinion in Microbiology, 2006, vol. 9, pp. 167-172.

Commichau, Fabian M., et al., "Glutamate Metabolism in *Bacillus subtilis*: Gene Expression and Enzyme Activities Evolved to Avoid Futile Cycles and to Allow Rapid Responses to Perturbations of the System", Journal of Bacteriology, 2008, vol. 190, No. 10, pp. 3557-3564.

DeVries, G.E. et al., "Cloning, Expression, and Sequence Analysis of the *Bacillus methanolicus* C1 Methanol Dehydrogenase Gene", Journal of Bacteriology, 1992, pp. 5346-5353, vol. 174, No. 16.

De Vries, Gert E., et al., "Physiology and genetics of methylotrophic bacteria", FEMS Microbiology Reviews, 1990, vol. 75, pp. 57-102.

Dijkhuizen, L., P. R. Levering, et al., "The Physiology and Biochemistry of Aerobic Methanol-Utilizing Gram-Negative and Gram Positive Bacteria", J.C. Murrell, et al. (eds.), New York, Plenum Press (1992), pp. 149-181 (on Order).

Haima, Peter, et al. "The effect of restriction on shotgun cloning and plasmid stability in *Bacillus subtilis* Marburg", Mol Gen Genet (1987) 209:335-342.

Hanson, R. S., et al., "Production of L-Lysine and Some Other Amino Acids by Mutants of *B. methanolicus*", Microbial Growth on $C_1$ Compounds, pp. 227-236, Kluwer Academic Publishers.

Hektor, Harm, J., et al., "Identification of a Magnesium-dependent NAD(P)(H)-binding Domain in the Nicotinoprotein Methanol Dehydrogenase from *Bacillus methanolicus*", The Journal of Biological Chemistry, 2002, vol. 277, 49, pp. 46966-46973.

Heid, Christian A., et al., "Genome Methods Real Time Quantitative PCR", Genome Research, 1996, pp. 986-994.

Holm, Liisa, et al., "Touring protein fold space with Dali/FSSP", Nucleic Acids Research, 1998, vol. 26, No. 1, pp. 316-319.

Jakobsen, Oyvind M., et al., "Overexpression of Wild-Type Aspartokinase Increases $_L$-Lysine Production in the Thermotolerant Methylotrophic Bacterium, *Bacillus methanolicus*", Applied and Environmental Microbiology, Feb. 2009, vol. 75, No. 3, pp. 652-661.

Jakobsen, Oyvind M., et al., "Upregulated Transcription of Plasmid and Chromosomal Ribulose Monophosphate Pathway Genes Is Critical for Methanol Assimilation Rate and Methanol Tolerance in the Methylotrophic Bacterium *Bacillus methanolicus*", Journal of Bacteriology, Apr. 2006, vol. 188, No. 8, pp. 3063-3072.

Kiefer, Florian, et al., "The SWISS-MODEL Repository and associated resources", Nucleic Acids Research, 2009, vol. 37, pp. D387-D392.

Kloosterman, Harm, et al., "Molecular, Biochemical, and Functional Characterization of a Nudix Hydrolase Protein That Stimulates the Activity of a Nicotinoprotein Alcohol Dehydrogenase", The Journal of Biological Chemistry, vol. 277, No. 38, Sep. 2002, pp. 34785-34792.

Komives, Claire F., et al., "Growth of *Bacillus methanolicus* in seawater-based media", J Ind Microbiol Biotechnol, 2005, vol. 32, No. 2, pp. 61-66.

Krog, Anne, et al., "Functional Characterization of Key Enzymes involved in $_L$-Glutamate Synthesis and Degradation in the Thermotolerant and Methylotrophic Bacterium *Bacillus methanolicus*", Applied and Environmental Microbiology, Sep. 2013, vol. 79, No. 17, pp. 5321-5328.

Kunst, F., et al., "The complete genome sequence of the Gram-positive bacterium *Bacillus subtilis*", Nature, 1997, vol. 390, No. 20, pp. 249-256.

Mills, David, A., et al., "Cloning and Sequence Analysis of the meso-Diaminopimelate Decarboxylase Gene from *Bacillus methanolicus* MGA3 and Comparison to Other Decarboxylase Genes", Applied and Environmental Microbiology, Sep. 1993, vol. 59, No. 9, pp. 2927-2937.

Nguyen, Hoang Duc, et al., "Construction of plasmid-based expression vectors for *Bacillus subtilis* exhibiting full structural stability", Plasmid, vol. 54, 2005, pp. 241-248.

NCBI Reference Sequence: YP_004860127.1, "iron-containing alcohol dehydrogenase, [Bacillus coagulans 36D1]", FASTA Graphics, 3 pages.

Pearson W.R., "Rapid and sensitive sequence comparison with FASTP and FASTA.", Methods Enzymol., 1990; 183:63-98 (one sheet).

Pearson, William R., et al., "Improved tools for biological sequence comparison", Proc. Natl. Adac. Sci., 1998, vol. 85, pp. 2444-2448.

Peyraud, Remi, et al., "Demonstration of the ethylmalonyl-CoA pathway by using $^{13}C$ metabolomics", PNAS, Mar. 24, 2009, vol. 106, No. 12, pp. 4846-4851.

Pluschkell, Stefanie B., et al., "Dissimilation of [$^{13}C$]methanol by continuous cultures of *Bacillus methanolicus* MGA3 at 50° C. studied by $^{13}C$ NMR and isotope-ratio mass spectrometry", Microbiology (2002), vol. 148, pp. 3223-3233.

Schendel, Frederick J., et al.. "$_L$-Lysine Production at 50° C. by Mutants of a Newly Isolated and Characterized Methylotrophic *Bacillus* sp.", Applied and Environmental Microbiology, 1990, vol. 56, No. 4, pp. 963-970.

(56) References Cited

OTHER PUBLICATIONS

Schendel, Frederick J., et al., "Cloning and Nucleotide Sequence of the Gene Coding for Aspartokinase II from a Thermophilic Methylotreophic *Bacillus* sp.", Applied and Environmental Microbiology, 1992, vol. 58, No. 9, pp. 2806-2814.

Schaffer, Alejandro A., et al., "Improving the accuracy of PSI-BLAST protein database searches with composition-based statistics and other refinements", Nucleic Acids Research, 2001, vol. 29, No. 14, pp. 2994-3005.

Thomson, Julie D., et al., "Clustal W: improving the sensitivity of progressive multiple sequence alignment through sequence weighting, position-specific gap penalties and weight matrix choice", 1994 Oxford University Press, Nucleic Acids Res., 22: 4673-4680; Abstract (one sheet).

Uniprot accession No. D7WPP7_9BACI, Unreviewed; 401 AA (one sheet).

Uniprot accession No. A3I908_9BACI, Unreviewed; 401 AA (two sheets).

Uniprot accession No. B1HX72_LYSSC, Unreviewed; 402 AA (one sheet).

Vonck, Janet, et al., "Electron Microscopic Analysis and Biochemical Characterization of a Novel Methanol Dehydrogenase from the Thermotolerant *Bacillus* sp. C1*", The Journal of Biological Chemistry, 1991, vol. 266, No. 6, pp. 3949-3954.

Van Domselaar, Gary H., et al. "BASys: a web server for automated bacterial genome annotation", Nucleic Acids Research, 2005, vol. 33 Web Server issue, pp. W455-W459.

Vorholt, Julia A., "Cofactor-dependent pathways of formaldehyde oxidation in methylotrophic bacteria", Arch Microbiol (2002) 178: 239-249.

Figure 1

```
mdh MGA3     1 atgac---aa-----caaact----tttttcattccaccagccagcgtaat
mdh-PB1      1 .....gca..-----g..----...................t........
mdh1-PB1     1 .....taa..-----.....a.----...........t..t....ct...t.
mdh2 MGA3    1 ..........---...acact.....g.gcat....t..g..tt...t..atc..t.
mdh3 MGA3    1 ....a---...acact.....g.gcat....a...g..tt...t..atc..t.
mdh2-PB1     1 ..........---...acact.....g.atat...a...a..tt...t..att.gt.

mdh MGA3    39 tggacgcggtgcagtaaaggaagtaggaacaagacttaagcaaattggag
mdh-PB1     42 .........c..t.....a...............................
mdh1-PB1    42 ......a..c..t...........tg.......a..agct..........
mdh2 MGA3   48 ...tgca..at....t..t...g..t......tc..t.agctg.tc....t.
mdh3 MGA3   48 ...tgca..ct.t..t..t...g..t......tc..t.agctggtc....t.
mdh2-PB1    48 ...t.ca..at.t..t...t...g..t......tc..t.agctggcc....c.

mdh MGA3    89 ctaagaaagcgcttatcgttacagatgcattccttcacagcacaggttta
mdh-PB1     92 ...ca.....a...................t.....tg..........g
mdh1-PB1    92 ...c......a...............c.......................g
mdh2 MGA3   98 tg...a.....tt.at.a..........tggt......g.ttt....c.t
mdh3 MGA3   98 tg...a.....tt.at.a..........tggt...........ttt...cc.t
mdh2-PB1    98 tg...a.....tt.at.a..........tggt......g..tt....c.t mdh MGA3   139 tctgaagaagttgctaaaaacattcgtgaagctggcgttgatgttgcgat
mdh-PB1    142 ..a............................c.......c...ta..
mdh1-PB1   142 ..a............................c...........ta..
mdh2 MGA3  148 ......a..a..t.c.gt.tt.........c......t..g...a..at.c..
mdh3 MGA3  148 ......a..a....cggt.t..............t..g...a..a..t..
mdh2-PB1   148 ......a..a....c.gt.t...............t..g...a..atta..

mdh MGA3   189 tttcccaaaagctcaaccagatccagcagatacacaagttcatgaaggtg
mdh-PB1    192 ................................................c.
mdh1-PB1   192 ...t..t.........................................c.
mdh2 MGA3  198 ...t........cg.....a......a.c.....a.a.c..cgca......t
mdh3 MGA3  198 ...t........cg.....a......a.t.....a.a.c..cgca......t
mdh2-PB1   198 ...t........cg.....a......a.t.....a.a.c..cgca......t mdh MGA3   239 tagatgtattcaaacaagaaaactgtgattcacttgtttctatcggtgga
mdh-PB1    242 .....a...............a......g.....................
mdh1-PB1   242 ....g................a......g....................g
mdh2 MGA3  248 ....a.cg.at..cgct..........cagca....ca..c.g..c..c
mdh3 MGA3  248 ....a.cg.at..cgct..........cagca....ca..c.t..c..c
mdh2-PB1   248 .g...a..g.at..cgct..........cagca....ca..t.g..c..c mdh MGA3   289 ggtagctctcacgatacagctaaagcaatcggtttagttgcagcaaacgg
mdh-PB1    292 ....................a.............................
mdh1-PB1   292 ..c.................a....g......c.................
mdh2 MGA3  298 ...a..t..a..t...g.c.ga.....c...t.ca.....a..t..t..t..
mdh3 MGA3  298 ...a.....a..t...g.t.ga.....c...t.ca.....a..t..t.....
mdh2-PB1   298 ...a.....g..t...g.t.ga....gc..t.ca.....a..t..t.....

mdh MGA3   339 cggaagaatcaatgactatcaaggtgtaaacagcgtagaaaaaccagtcg
mdh-PB1    342 ............c......................t...........g..t.
mdh1-PB1   342 ............c......................t..t...........a....
mdh2 MGA3  348 t.....a...tc.c...t...g.......cg.tgtatc.a...g.....a.g.
mdh3 MGA3  348 t.....c...tc.c...t...g.......cg.tgtatc.a.........a.g.
mdh2-PB1   348 t.....c...tt.c...t...g.......cg.t.aatc.a.........a.g.
```

Figure 1 contd.

```
mdh MGA3      389  ttccagtagttgcaatcactacaacagctggtactggtagtgaaacaaca
mdh-PB1       392  ..................................................
mdh1-PB1      392  .....caga........................a................
mdh2 MGA3     398  .c..gc..a....g...t.a.............a..c......tt...t
mdh3 MGA3     398  .c..tc..a....g...t.a.............a..c......tt...t
mdh2-PB1      398  .c..gc.ca....g...t.a.............a..c......tt...t mdh MGA3      439  tctcttgcggttattacagactctgcacgtaaagtaaaaatgcctgttat
mdh-PB1       442  .....................t........................a.....
mdh1-PB1      442  ...........................................g.....
mdh2 MGA3     448  aaat.ca.aa.c...c.....ta...a...c.....g......g.ca..g.
mdh3 MGA3     448  aaat.ca.aa.c...c.....ta...a...c.....g......g.ca..g.
mdh2-PB1      448  agat...a.aa.c...c.....ta...a.........g......g.ga..g.

mdh MGA3      489  tgatgagaaaattactccaactgtagcaattgttgacccagaattaatgg
mdh-PB1       492  c..............a..................................
mdh1-PB1      492  ......a........a..................................
mdh2 MGA3     498  g...a.ac.tg.a..a..t..ac.tt....caac........gc......
mdh3 MGA3     498  ....a.ac.tg.a..a..t..ac.tt....caa.........gc......
mdh2-PB1      498  ....a.ac.tg.a..a..t..ac.tt....caac........c......

mdh MGA3      539  tgaaaaaaccagctggattaacaatcgcaactggtatggatgcattgtcc
mdh-PB1       542  .........................t....................a...
mdh1-PB1      542  ..........................a...................a...
mdh2 MGA3     548  .tgg..tg..tc.gtcc.....tgct..t.....at.a........aa.t
mdh3 MGA3     548  .tgg..tg..tc.gtcc.....gct..t.....at.a........aa.t
mdh2-PB1      548  .cgg..tg..tc.gtct......gct..t.....at.a........aa.t mdh MGA3      589  catgcaattgaagcatatgttgcaaaaggtgctacaccagttactgatgc
mdh-PB1       592  ......................c...........................
mdh1-PB1      592  ......................c...........................
mdh2 MGA3     598  ..................t...ct........t...a....a......
mdh3 MGA3     598  ......g...........t...ct........t...a....a......
mdh2-PB1      598  ..............t......t...cg.c.....t...a....a......

mdh MGA3      639  atttgctattcaagcaatgaaacttatcaatgaatacttaccaaaagcgg
mdh-PB1       642  g.....a................c..t..............cgt....
mdh1-PB1      642  ......g................c..t......................
mdh2 MGA3     648  .c....a.....g..g..c...a.c..ttc.a.......g..gcgt...a
mdh3 MGA3     648  .c....a.....g..g..c...a....ttc.a.......g..gcgt...a
mdh2-PB1      648  .c....c.....g..g..c...a.c..ttc.a.......g...cgt...at mdh MGA3      689  ttgcgaacggagaagacatcgaagcacgtgaaaaaatggcttatgcacaa
mdh-PB1       692  ....a..t.....................gc...................
mdh1-PB1      692  ....a..t.....................gc...................
mdh2 MGA3     698  ....a..t...a......t.............c......c.tc...t...
mdh3 MGA3     698  ....a..t...a......t.............c......c.tc......
mdh2-PB1      698  ....a..t..ca....t..g...........gc......c.tc...t...

mdh MGA3      739  tacatggcaggagtggcatttaacaacggtggtttaggactagttcactc
mdh-PB1       742  ..............................a........t....a......
mdh1-PB1      742  ....................t.....a.........t....a......
mdh2 MGA3     748  .cat.a..t..ca........c..t....cg........ctat.....tg.
mdh3 MGA3     748  .cat.a..t..ca........c..t....cg........ctat.....tg.
mdh2-PB1      748  .cat.a..t..ta..........t.....c.tc......ctat.....tg.
```

Figure 1 contd.

```
mdh MGA3     789  tatttctcaccaagtaggtggagtttacaaattacaacacggaatctgta
mdh-PB1      792  ................................g.................
mdh1-PB1     792  ..................................................
mdh2 MGA3    798  g...g.a......t....a...t.c......c..c.ct..t..cg.t..c.
mdh3 MGA3    798  g...g.a......t....a...t.c......c..c.ct..t..cg.t..c.
mdh2-PB1     798  a...g.a......t.t..c...t.c......c..c.ct..t..cg.t..c.

mdh MGA3     839  actcagttaatatgccacacgtttgcgcattcaacctaattgctaaaact
mdh-PB1      842  .........................ca......t.........cgt...
mdh1-PB1     842  ........gta.......t......ca......t.........cgt...
mdh2 MGA3    848  .tg.g..cct.c.....t.t...a..tcg...t...t......t.....gtg
mdh3 MGA3    848  .tg.ga.cct.c....g..t.....tcgt......t.....t.....gtg
mdh2-PB1     848  .tg.ga.cct.c.......t...a...cg...t..tt.....t.....gtg mdh MGA3     889  gagcgcttcgcacacattgctgagcttttaggtgagaatgttgctggctt
mdh-PB1      892  ...a...............................c.........t........
mdh1-PB1     892  ...a...............................c.........t........
mdh2 MGA3    898  ...a..t.at...g.a..c....ctt..c.t......a......c.ac..tc.
mdh3 MGA3    898  ...a..t.at...g.a..c....ctt..c.t......a......c.ac...c.
mdh2-PB1     898  ...a..t..t...g.a.........ct..cc.......a.......c...c....c.

mdh MGA3     939  aagcactgcagcagctgctgagagagcaattgtagctcttgaaagaatca
mdh-PB1      942  .........t.t.....................g...c..c.ctat.
mdh1-PB1     942  .........t.t.....a..a...a......c...g......c.cta..
mdh2 MGA3    948  ...t..gtac.at..a......a.a...t...aa...ga.c........gg
mdh3 MGA3    948  ......ctac.a...a......a.a...t...aa...ga.c........gg
mdh2-PB1     948  ...t...cgc.a...a......a.a..gt...aa...ga.c........gg mdh MGA3     989  acaaatccttcggtatcccatctggctatgcagaaatgggcgtgaaagaa
mdh-PB1      992  .....aa................................a......
mdh1-PB1     992  ...g.aa........t.....a......aa..c.........a......
mdh2 MGA3    998  ct...ga.c.taac..t...aaa....t.aa....c.a..t.ct......
mdh3 MGA3    998  ct.g.ga.c.taac..t...aaa....t.aa....c.a..t.ct......
mdh2-PB1     998  ct...ga.c.taac..t...aga....t.aa....c....t.ct......

mdh MGA3    1039  gaggatatcgaattattagcgaaaaacgcatacgaagacgtatgtactca
mdh-PB1     1042  .................c.....g...c.................t
mdh1-PB1    1042  ...a..............a..c......atgc....t..........t
mdh2 MGA3   1048  ...a..c...t..gact.....t..g..t..gatga....t.c....g.att
mdh3 MGA3   1048  ...a.....t...gact.....t.....t..gatga.t..t.c....g.att
mdh2-PB1    1048  ...a..c...t.tgact.....tg....t..gatga....t.c.acgg.att mdh MGA3    1089  aagcaacccacgcgttcctactgttcaagacattgcacaaatcatcaaaa
mdh-PB1     1092  .gat........t.....................................
mdh1-PB1    1092  .ga......t..t..c.....g............ca...............
mdh2 MGA3   1098  ..ca..t..t...taaa....agt.ag....ag.catc.....t..t....
mdh3 MGA3   1098  ..ca..t..t...taaa....agt.ag....ag.catc.....t..t....
mdh2-PB1    1098  ..ca..t..t...taaa....agt.gg....ag..at......t..t....

mdh MGA3    1139  acgctatgtaa     (SEQ ID NO:7)
mdh-PB1     1142  .....c.....     (SEQ ID NO:9)
mdh1-PB1    1142  .....c.....     (SEQ ID NO:11)
mdh2 MGA3   1148  .t..g......     (SEQ ID NO:1)
mdh3 MGA3   1148  .t.........     (SEQ ID NO:3)
mdh2-PB1    1148  .t.........     (SEQ ID NO:5)
```

Figure 2

(A)

```
mdh  MGA3 protein    1  ---mt-t-n---ffippasvigrgavkevgtrlkqigakkalivtdaflh
mdh  PB1  protein    1  ---..-qr.---..........................t...........
mdh1 PB1  protein    1  ---..k.-k---....sst.f.........a....a....t..........
mdh2 MGA3 protein    1  ---..-n-tqsa...m.svnlf.a.s.n......adl.v....l....g..
mdh3 MGA3 protein    1  mkntq-s-a---.ym.svnlf.a.s.n......agl.v....l....g..
mdh2 PB1  protein    1  ---..-n-tqsi.y..svnlf.p.s.n......agl.v....l....g..

mdh  MGA3 protein   43  stglseevaknireagvdvaifpkaqpdpadtqvhegvdvfkqencdslv
mdh  PB1  protein   44  g..............l.av......................i....k..a..
mdh1 PB1  protein   44  ...............l..v............................e....k..a..
mdh2 MGA3 protein   46  gl....kissi..a...e.s......e.n.t.kn.a...leayna.....i.
mdh3 MGA3 protein   46  .l....ki.gi......e.......e.n.t.kn.a...leayna.....i.
mdh2 PB1  protein   46  gl....ki.si......e.l.....e.n.t.kn.a...le.yna.....i.

mdh  MGA3 protein   93  sigggsshdtakaiglvaanggrindyqgvnsvekpvvpvvaitttagtg
mdh  PB1  protein   94  ..................................................
mdh1 PB1  protein   94  .........g.......................q...qi..........
mdh2 MGA3 protein   96  tl.......ag...a........k.h..e..dvske.m..li..n......
mdh3 MGA3 protein   96  tl.......ag...a........t.h..e..dvsk..m..li..n......
mdh2 PB1  protein   96  tl.......ag.g.a........t.y..e..dksk..m..li..n......

mdh  MGA3 protein  143  settslavitdsarkvkmpvidekitptvaivdpelmvkkpagltiatgm
mdh  PB1  protein  144  ..................................................
mdh1 PB1  protein  144  ..................................................
mdh2 MGA3 protein  146  ..l.kfti...te.....aiv.khv...ls.n......gm.ps..a...l
mdh3 MGA3 protein  146  ..l.kfti...te.....aiv.khv...ls.n......gm.ps..a...l
mdh2 PB1  protein  146  ..l.rfti...te.....aiv.khv...ls.n......gm.ps..a...l mdh  MGA3 protein  193  dalshaieayvakgatpvtdafaiqamklineylpkavangediearekm
mdh  PB1  protein  194  .............r......................r...........a.
mdh1 PB1  protein  194  .............r......................r...........a.
mdh2 MGA3 protein  196  ...t........st....i....l.....i.i.sk...r.....k......q.
mdh3 MGA3 protein  196  ...t........st....i....l.....i.i.sk...r.....k......q.
mdh2 PB1  protein  196  ...t........sta...i....l.....i.i.sk...r.f...k.m....q.

mdh  MGA3 protein  243  ayaqymagvafnngglglvhsishqvggvyklqhgicnsvnmphvcafnl
mdh  PB1  protein  244  ............................................q...
mdh1 PB1  protein  244  .......................................v.....q...
mdh2 MGA3 protein  246  .f..sl..m....a...y..a.a..l..f.nfp..v..a.ll.y..r...
mdh3 MGA3 protein  246  .f..sl..m....a...y..a.a..l..f.nfp..v..aill.y..r...
mdh2 PB1  protein  246  .f..sl..m....as..y..a.a..f..f.nfp..v..aill....r...

mdh  MGA3 protein  293  iakterfahiaellgenvaglstaaaaeraivalerinksfgipsgyaem
mdh  PB1  protein  294  ...r.................s......s..........q.y..n.........
mdh1 PB1  protein  294  ...r.................s......s.....t.a....y.rn........ka.
mdh2 MGA3 protein  296  .s.v..y.e...af.....d....yd...k..k.i..ma.dln..k.fk.l
mdh3 MGA3 protein  296  .s.v..y.e...af.....d....ye...k..k.i..mardln..k.fk.l
mdh2 PB1  protein  296  .s.v....e...a..........re...kg.k.i..ma.dln..r.fk.l mdh  MGA3 protein  343  gvkeediellaknayedvctqsnprvptvqdiaqiiknam (SEQ ID NO:8)
mdh  PB1  protein  344  ..........n...q....ld..................l (SEQ ID NO:10)
mdh1 PB1  protein  344  ..........n...mq....ld.................q......l (SEQ ID NO:12)
mdh2 MGA3 protein  346  .a......t.....mk.a.alt...k.kleevi....... (SEQ ID NO:2)
mdh3 MGA3 protein  346  .a......t.....mn.a.alt...k.kleevi....... (SEQ ID NO:4)
mdh2 PB1  protein  346  .a.....vt..e...mk.atalt...k.kleevi....... (SEQ ID NO:6)
```

Figure 2 contd.
(B)

```
Sequence              Start    End    Match   NonMatch   %Match
mdh2 MGA3 protein        1     385
mdh3 MGA3 protein        1     385     370       15        96
mdh2 PB1 protein         1     385     353       32        91 mdh2 MGA3 protein      1 mtntqsaffmpsvnlfgagsvnevgtrladlgvkkallvtdaglhglgls
mdh3 MGA3 protein      1 .k......y....................g...............s....
mdh2 PB1 protein       1 ......i.yi.......p...........g....................

mdh2 MGA3 protein     51 ekissiiraagvevsifpkaepnptdknvaegleaynaencdsivtlggg
mdh3 MGA3 protein     51 ...ag...e.....a...................................
mdh2 PB1 protein      51 ...a....e.....l.......................v...........

mdh2 MGA3 protein    101 sshdagkaialvaanggkihdyegvdvskepmvpliainttagtgseltk
mdh3 MGA3 protein    101 .................t...........k....................
mdh2 PB1 protein     101 .......g........t.y......k...k...................r mdh2 MGA3 protein    151 ftiitdterkvkmaivdkhvtptlsindpelmvgmppsltaatgldalth
mdh3 MGA3 protein    151 ..................................................
mdh2 PB1 protein     151 ..................................................

mdh2 MGA3 protein    201 aieayvstgatpitdalaiqaikiiskylpravangkdieareqmafaqs
mdh3 MGA3 protein    201 ..................................................
mdh2 PB1 protein     201 ........a.......................f.....m..........

mdh2 MGA3 protein    251 lagmafnnaglgyvhaiahqlggfynfphgvcnavllpyvcrfnliskve
mdh3 MGA3 protein    251 ..........................................i...h..........
mdh2 PB1 protein     251 ..........s...........f.................i...h............

mdh2 MGA3 protein    301 ryaeiaaflgenvdglstydaaekaikaiermakdlnipkgfkelgakee
mdh3 MGA3 protein    301 ....................e..............r..............
mdh2 PB1 protein     301 .f.....l.....a....re....g..............r..........

mdh2 MGA3 protein    351 dietlaknamkdacaltnprkpkleeviqiiknam  (SEQ ID NO:2)
mdh3 MGA3 protein    351 ..........n........................  (SEQ ID NO:4)
mdh2 PB1 protein     351 ...v...e......t....................  (SEQ ID NO:6)
```

Figure 3
(A)
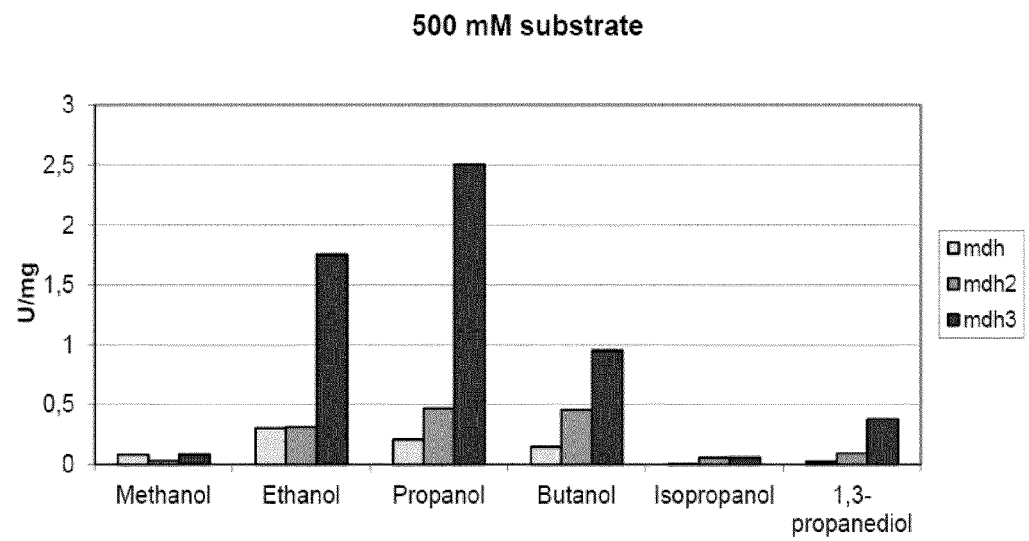
(B)
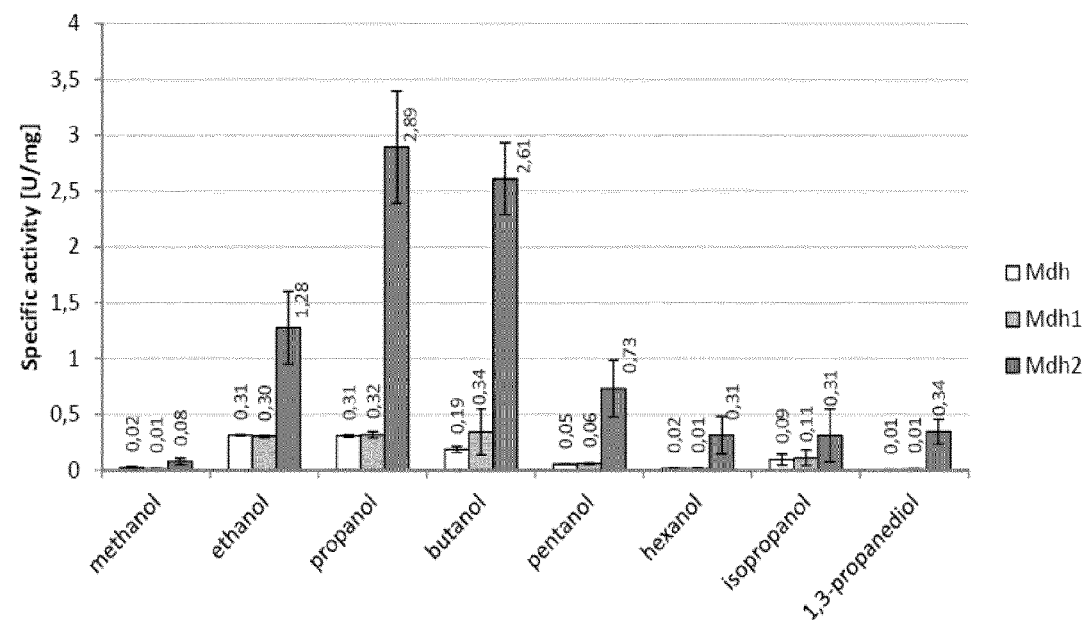

Figure 4
(A)
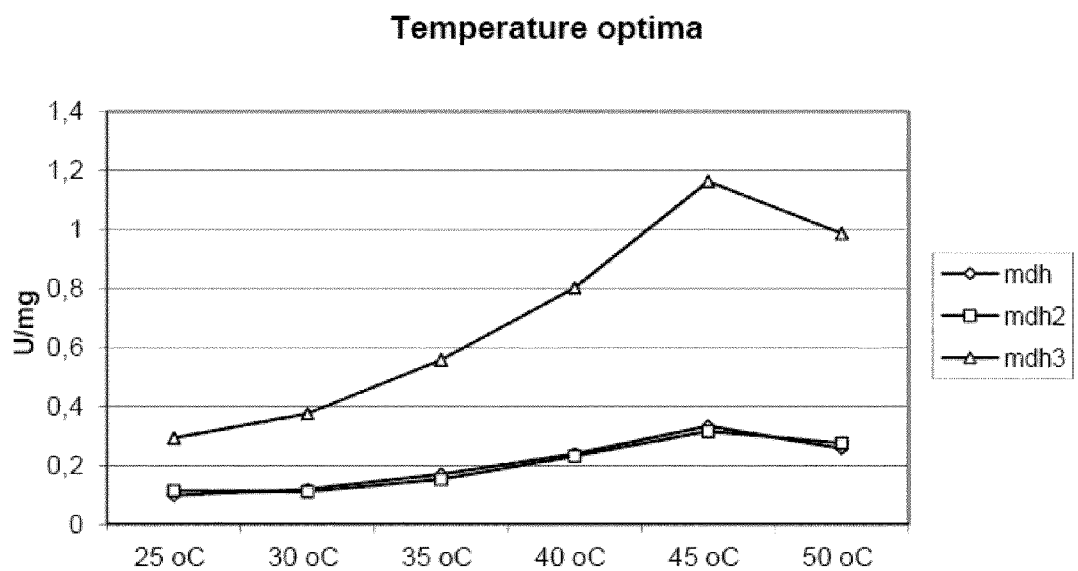
(B)
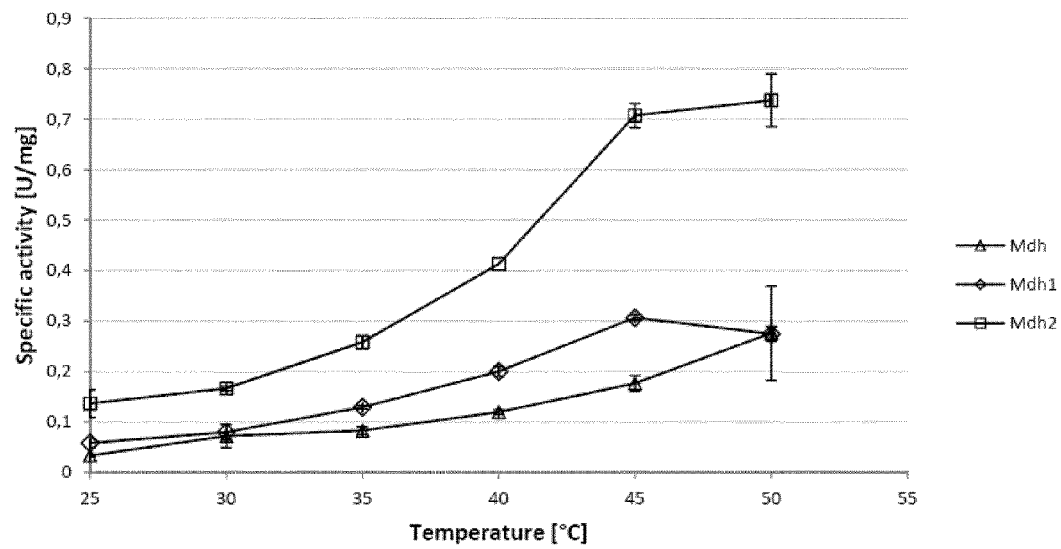

Figure 5
(A)
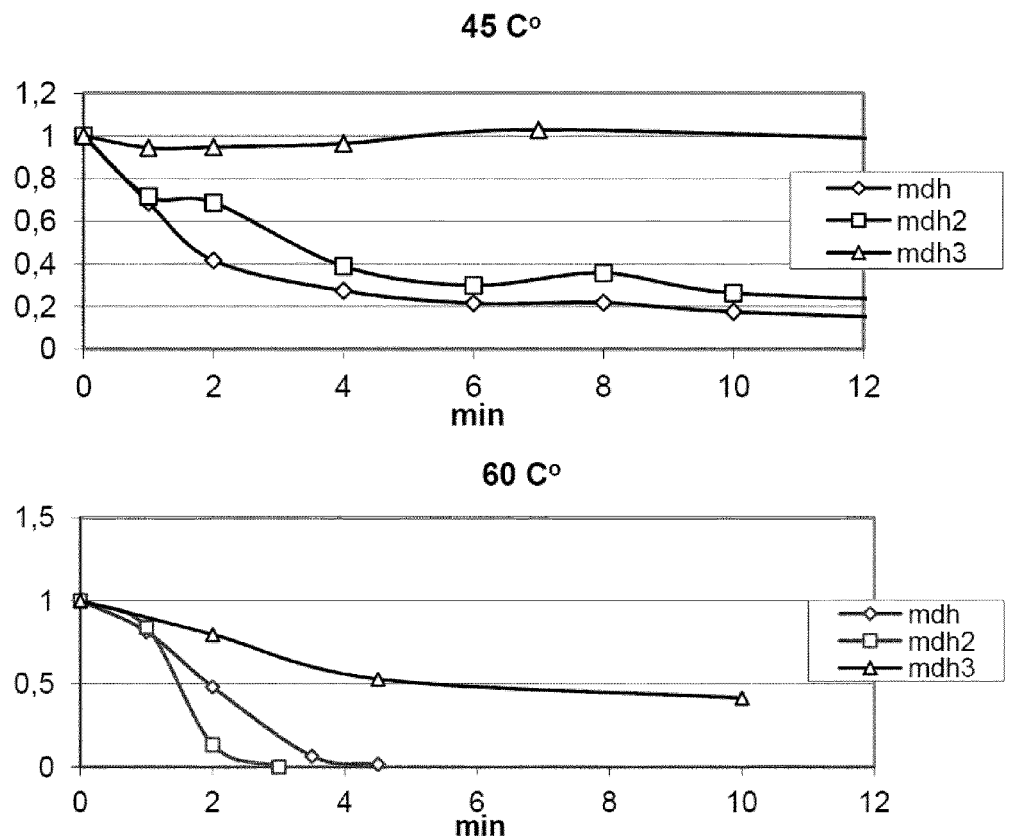
(B)
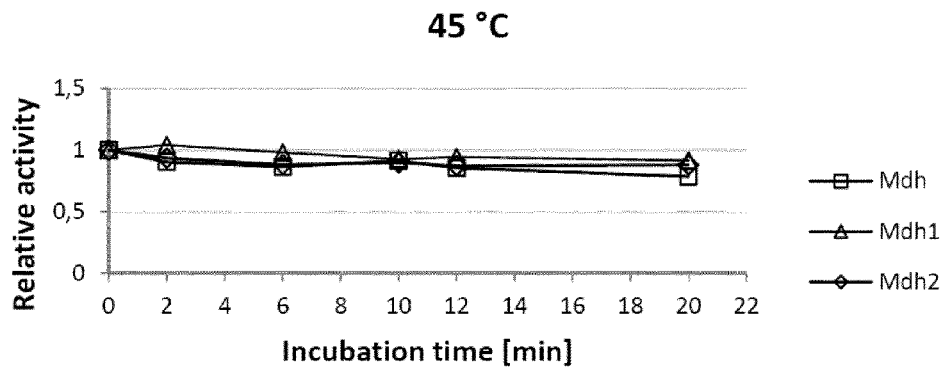

Figure 5 contd.
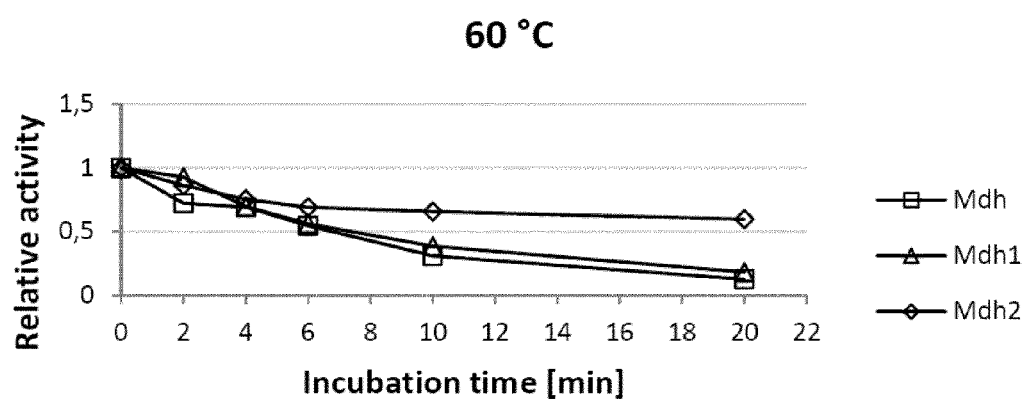

Figure 6
(A)
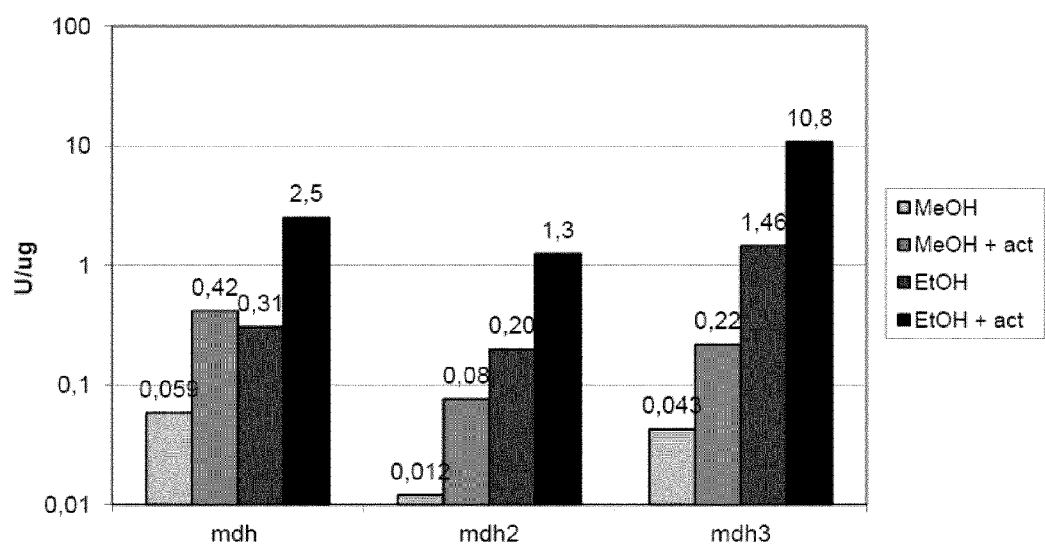
(B)
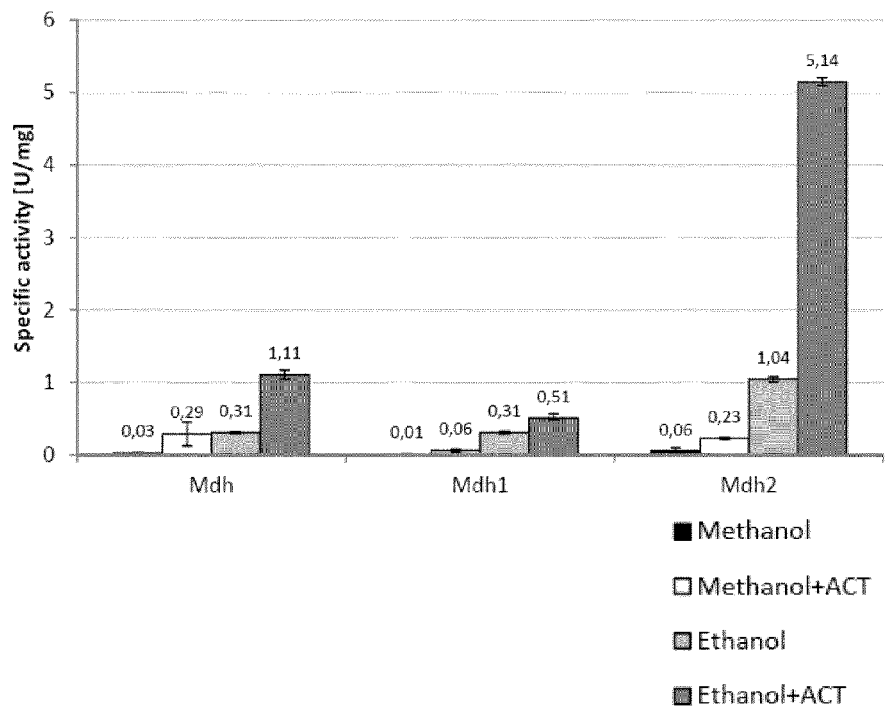

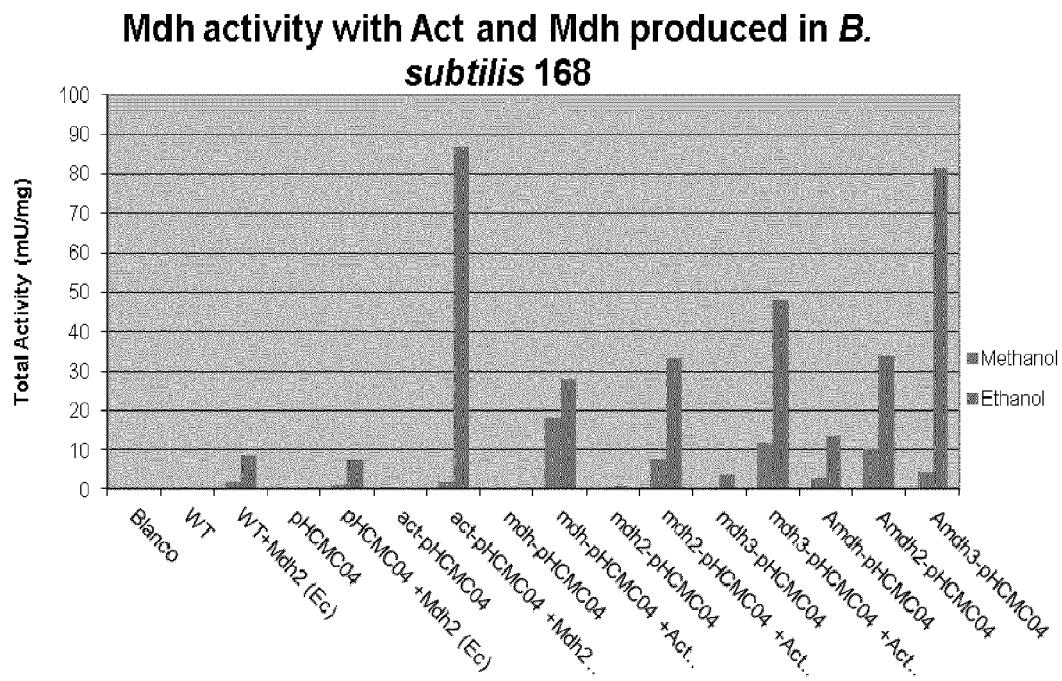

Abbreviations:
Blanco =Resuspension buffer;
WT = wildtype host *B. subtilis* 168;
WT + Mdh2(EC) =*E. coli* lysate with Mdh2 expressed from the pET21a plasmid;
pHCMC04 = B. subtilis 168 with empty vector pHCMC04;
pHCMC04+Mdh2(Ec) = pHCMC04 with E. coli lysate with mdh2 expressed from pET21a plasmid;
act-pHCMC04 = *B. subtilis* 168 lysate with Act expressed from the pHCMC04 plasmid;
act-pHCMC04+Mdh2(Ec) = act-pHCMS04 with E. coli lysate with mdh2 expressed from pET21a plasmid;
mdh1-pHCMC04 = *B. subtilis* 168 lysate with mdh1 expressed from the pHCMC04 plasmid;
mdh1-pHCMC04+Act(Ec) = mdh1-pHCMC04 with *E. coli* lysate with act expressed from the pET21a plasmid;
mdh2-pHCMC04 = *B. subtilis* 168 lysate with mdh2 expressed from the pHCMC04 plasmid;
mdh2-pHCMC04+Act(Ec) = mdh2-pHCMC04 with *E. coli* lysate with act expressed from the pET21a plasmid;
mdh3-pHCMC04 = *B. subtilis* 168 lysate with mdh3 expressed from the pHCMC04 plasmid;
mdh3-pHCMC04+Act(Ec) = mdh3-pHCMC04 with *E. coli* lysate with act expressed from the pET21a plasmid;
Amdh1-pHCMC04 =*B. subtilis* 168 lysate with act and mdh1 expressed from the pHCMC04 plasmid.
Amdh2-pHCMC04 =*B. subtilis* 168 lysate with act and mdh2 expressed from the pHCMC04 plasmid.
Amdh3-pHCMC04 =*B. subtilis* 168 lysate with act and mdh3 expressed from the pHCMC04 plasmid.

| Construct | operon |
|---|---|
| act | Spel — RBS — act — SwaI BglII — His6 — BamHI |
| Amdh | Spel — RBS — act — RBS — mdh — SwaI BglII — His6 — BamHI |
| AMhxlA | Spel — RBS — act — RBS — mdh — RBS — hxlA — SwaI BglII — His6 — BamHI |
| AMhxlB | Spel — RBS — act — RBS — mdh — RBS — hxlA — RBS — hxlB — SwaI BglII — His6 — BamHI |
| AMABglpX | Spel — RBS — act — RBS — mdh — RBS — hxlA — RBS — hxlB — RBS — glpX — SwaI BglII — His6 — BamHI |
| AMABGfba | Spel — act — mdh — hxlA — hxlB — glpX — fba — Swa BglII — His6 — BamHI |
| AMABGftkt | Spel — act — mdh — hxlA — hxlB — glpX — fba — tkt — Swa BglII — His6 — BamHI |
| AMABGFTpfk | Spel — act — mdh — hxlA — hxlB — glpX — fba — tkt — pfk — Swa BglII — His6 — BamHI |
| AMABGFTPrpe | Spel — act — mdh — hxlA — hxlB — glpX — fba — tkt — pfk — rpe — Swa BglII — His6 — BamHI |

SEQUENCE LISTING

```
<160> NUMBER OF SEQ ID NOS: 45

<210> SEQ ID NO 1
<211> LENGTH: 1158
<212> TYPE: DNA
<213> ORGANISM: Bacillus methanolicus MGA3

<400> SEQUENCE: 1
atgacaaaca ctcaaagtgc attttttatg ccttcagtca atctatttgg tgcaggatca      60
gttaatgagg ttggaactcg attagctgat cttggtgtga aaaaagcttt attagttaca     120
gatgctggtc ttcacggttt aggtctttct gaaaaaattt ccagtattat tcgtgcagct     180
ggtgtggaag tatccatttt tccaaaagcc gaaccaaatc caaccgataa aaacgtcgca     240
gaaggtttag aagcgtataa cgctgaaaac tgtgacagca ttgtcactct gggcggcgga     300
agttcacatg atgccggaaa agccattgca ttagtagctg ctaatggtgg aaaaattcac     360
gattatgaag gtgtcgatgt atcaaaagaa ccaatggtcc cgctaattgc gattaataca     420
acagctggta caggcagtga attaactaaa ttcacaatca tcacagatac tgaacgcaaa     480
gtgaaaatgg ccattgtgga taacatgta acacctacac tttcaatcaa cgacccagag     540
ctaatggttg gaatgcctcc gtccttaact gctgctactg gattagatgc attaactcat     600
gcaattgaag catatgtttc aactggtgct actccaatta cagatgcact tgcaattcag     660
gcgatcaaaa tcatttctaa atacttgccg cgtgcagttg caaatggaaa agacattgaa     720
gcacgtgaac aaatggcctt cgctcaatca ttagctggca tggcattcaa taacgcgggt     780
ttaggctatg ttcatgcgat tgcacaccaa ttaggaggat tctacaactt ccctcatggc     840
gtttgcaatg cggtccttct gccatatgta tgtcgattta acttaatttc taaagtggaa     900
cgttatgcag aaatcgctgc ttttcttggt gaaaatgtcg acggtctaag tacgtacgat     960
gcagctgaaa aagctattaa agcgatcgaa agaatggcta aagaccttaa cattccaaaa    1020
ggctttaaag aactaggtgc taaagaagaa gacattgaga ctttagctaa gaatgcgatg    1080
aaagatgcat gtgcattaac aaatcctcgt aaacctaagt tagaagaagt catccaaatt    1140
```

```
attaaaaatg cgatgtaa                                                    1158
```

<210> SEQ ID NO 2
<211> LENGTH: 385
<212> TYPE: PRT
<213> ORGANISM: Bacillus methanolicus MGA3

<400> SEQUENCE: 2

```
Met Thr Asn Thr Gln Ser Ala Phe Phe Met Pro Ser Val Asn Leu Phe
1               5                   10                  15

Gly Ala Gly Ser Val Asn Glu Val Gly Thr Arg Leu Ala Asp Leu Gly
            20                  25                  30

Val Lys Lys Ala Leu Leu Val Thr Asp Ala Gly Leu His Gly Leu Gly
        35                  40                  45

Leu Ser Glu Lys Ile Ser Ile Ile Arg Ala Ala Gly Val Glu Val
    50                  55                  60

Ser Ile Phe Pro Lys Ala Glu Pro Asn Pro Thr Asp Lys Asn Val Ala
65                  70                  75                  80

Glu Gly Leu Glu Ala Tyr Asn Ala Glu Asn Cys Asp Ser Ile Val Thr
                85                  90                  95

Leu Gly Gly Gly Ser Ser His Asp Ala Gly Lys Ala Ile Ala Leu Val
            100                 105                 110

Ala Ala Asn Gly Gly Lys Ile His Asp Tyr Glu Gly Val Asp Val Ser
        115                 120                 125

Lys Glu Pro Met Val Pro Leu Ile Ala Ile Asn Thr Thr Ala Gly Thr
    130                 135                 140

Gly Ser Glu Leu Thr Lys Phe Thr Ile Ile Thr Asp Thr Glu Arg Lys
145                 150                 155                 160

Val Lys Met Ala Ile Val Asp Lys His Val Thr Pro Thr Leu Ser Ile
                165                 170                 175

Asn Asp Pro Glu Leu Met Val Gly Met Pro Pro Ser Leu Thr Ala Ala
            180                 185                 190

Thr Gly Leu Asp Ala Leu Thr His Ala Ile Glu Ala Tyr Val Ser Thr
        195                 200                 205

Gly Ala Thr Pro Ile Thr Asp Ala Leu Ala Ile Gln Ala Ile Lys Ile
    210                 215                 220

Ile Ser Lys Tyr Leu Pro Arg Ala Val Ala Asn Gly Lys Asp Ile Glu
225                 230                 235                 240

Ala Arg Glu Gln Met Ala Phe Ala Gln Ser Leu Ala Gly Met Ala Phe
                245                 250                 255

Asn Asn Ala Gly Leu Gly Tyr Val His Ala Ile Ala His Gln Leu Gly
            260                 265                 270

Gly Phe Tyr Asn Phe Pro His Gly Val Cys Asn Ala Val Leu Leu Pro
        275                 280                 285

Tyr Val Cys Arg Phe Asn Leu Ile Ser Lys Val Glu Arg Tyr Ala Glu
    290                 295                 300

Ile Ala Ala Phe Leu Gly Glu Asn Val Asp Gly Leu Ser Thr Tyr Asp
305                 310                 315                 320

Ala Ala Glu Lys Ala Ile Lys Ala Ile Glu Arg Met Ala Lys Asp Leu
                325                 330                 335

Asn Ile Pro Lys Gly Phe Lys Glu Leu Gly Ala Lys Glu Glu Asp Ile
            340                 345                 350

Glu Thr Leu Ala Lys Asn Ala Met Lys Asp Ala Cys Ala Leu Thr Asn
        355                 360                 365
```

Pro Arg Lys Pro Lys Leu Glu Glu Val Ile Gln Ile Ile Lys Asn Ala
      370                 375                 380

Met
385

<210> SEQ ID NO 3
<211> LENGTH: 1158
<212> TYPE: DNA
<213> ORGANISM: Bacillus methanolicus MGA3

<400> SEQUENCE: 3

```
atgaaaaaca ctcaaagtgc attttacatg ccttcagtca atctatttgg tgcaggctct     60
gttaatgagg ttggaactcg attagctggt cttggtgtga aaaaagcttt attagttaca    120
gatgctggtc ttcacagttt aggcctttct gaaaaaattg ccggtatcat tcgtgaagct    180
ggtgtggaag tagctatttt tccaaaagcc gaaccaaatc caactgataa aaacgtcgca    240
gaaggtttag aagcgtataa cgctgaaaac tgtgacagca ttgtcactct ggcggcgga    300
agctcacatg atgctggaaa agccattgca ttagtagctg ctaacggtgg aacaattcac    360
gattatgaag gtgtcgatgt atcaaaaaaa ccaatggtcc ctctaattgc gattaataca    420
acagctggta caggcagtga attaactaaa ttcacaatca tcacagatac tgaacgcaaa    480
gtgaaaatgg ccattgttga taaacatgta acacctacac tttcaatcaa tgacccagag    540
ctaatggttg aatgcctcc gtccttaaca gctgctactg gattagatgc attaactcat    600
gcgattgaag catatgtttc aactggtgct actccaatta cagatgcact tgcaattcag    660
gcgatcaaaa ttatttctaa atacttgccg cgtgcagttg caaatggaaa agacattgaa    720
gcacgtgaac aaatggcctt cgcacaatca ttagctggca tggcattcaa taacgcgggt    780
ttaggctatg ttcatgcgat tgcacaccaa ttaggaggat tctacaactt ccctcatggc    840
gtttgcaatg cgatccttct gccgcatgtt tgtcgtttca acttaatttc taaagtggaa    900
cgttatgcag aaatcgctgc ttttcttggt gaaaatgtcg acggcctaag cacctacgaa    960
gcagctgaaa agctattaa agcgatcgaa agaatggcta gagaccttaa cattccaaaa   1020
ggctttaaag aactaggtgc taagaagaa gatattgaga ctttagctaa aaatgcgatg   1080
aatgatgcat gtgcattaac aaatcctcgt aaacctaagt tagaagaagt catccaaatt   1140
attaaaaatg ctatgtaa                                                 1158
```

<210> SEQ ID NO 4
<211> LENGTH: 385
<212> TYPE: PRT
<213> ORGANISM: Bacillus methanolicus MGA3

<400> SEQUENCE: 4

Met Lys Asn Thr Gln Ser Ala Phe Tyr Met Pro Ser Val Asn Leu Phe
1               5                   10                  15

Gly Ala Gly Ser Val Asn Glu Val Gly Thr Arg Leu Ala Gly Leu Gly
            20                  25                  30

Val Lys Lys Ala Leu Leu Val Thr Asp Ala Gly Leu His Ser Leu Gly
        35                  40                  45

Leu Ser Glu Lys Ile Ala Gly Ile Ile Arg Glu Ala Gly Val Glu Val
    50                  55                  60

Ala Ile Phe Pro Lys Ala Glu Pro Asn Pro Thr Asp Lys Asn Val Ala
65                  70                  75                  80

Glu Gly Leu Glu Ala Tyr Asn Ala Glu Asn Cys Asp Ser Ile Val Thr 85                  90                  95
Leu Gly Gly Gly Ser Ser His Asp Ala Gly Lys Ala Ile Ala Leu Val
            100                 105                 110

Ala Ala Asn Gly Gly Thr Ile His Asp Tyr Glu Gly Val Asp Val Ser
        115                 120                 125

Lys Lys Pro Met Val Pro Leu Ile Ala Ile Asn Thr Thr Ala Gly Thr
    130                 135                 140

Gly Ser Glu Leu Thr Lys Phe Thr Ile Ile Thr Asp Thr Glu Arg Lys
145                 150                 155                 160

Val Lys Met Ala Ile Val Asp Lys His Val Thr Pro Thr Leu Ser Ile
                165                 170                 175

Asn Asp Pro Glu Leu Met Val Gly Met Pro Pro Ser Leu Thr Ala Ala
            180                 185                 190

Thr Gly Leu Asp Ala Leu Thr His Ala Ile Glu Ala Tyr Val Ser Thr
        195                 200                 205

Gly Ala Thr Pro Ile Thr Asp Ala Leu Ala Ile Gln Ala Ile Lys Ile
    210                 215                 220

Ile Ser Lys Tyr Leu Pro Arg Ala Val Ala Asn Gly Lys Asp Ile Glu
225                 230                 235                 240

Ala Arg Glu Gln Met Ala Phe Ala Gln Ser Leu Ala Gly Met Ala Phe
                245                 250                 255

Asn Asn Ala Gly Leu Gly Tyr Val His Ala Ile Ala His Gln Leu Gly
            260                 265                 270

Gly Phe Tyr Asn Phe Pro His Gly Val Cys Asn Ala Ile Leu Leu Pro
        275                 280                 285

His Val Cys Arg Phe Asn Leu Ile Ser Lys Val Glu Arg Tyr Ala Glu
    290                 295                 300

Ile Ala Ala Phe Leu Gly Glu Asn Val Asp Gly Leu Ser Thr Tyr Glu
305                 310                 315                 320

Ala Ala Glu Lys Ala Ile Lys Ala Ile Glu Arg Met Ala Arg Asp Leu
                325                 330                 335

Asn Ile Pro Lys Gly Phe Lys Glu Leu Gly Ala Lys Glu Glu Asp Ile
            340                 345                 350

Glu Thr Leu Ala Lys Asn Ala Met Asn Asp Ala Cys Ala Leu Thr Asn
        355                 360                 365

Pro Arg Lys Pro Lys Leu Glu Glu Val Ile Gln Ile Ile Lys Asn Ala
    370                 375                 380

Met
385

<210> SEQ ID NO 5
<211> LENGTH: 1158
<212> TYPE: DNA
<213> ORGANISM: Bacillus methanolicus PB1

<400> SEQUENCE: 5
atgacaaaca ctcaaagtat atttacata ccttcagtca atttgtttgg tccaggatct        60
gttaatgagg ttggaactcg attagctggc cttggcgtga aaaaagcttt attagttaca       120
gatgctggtc ttcacggctt aggtctttct gaaaaattg ccagtatcat tcgtgaagct       180
ggtgtggaag tattaatttt tccaaaagcc gaaccaaatc caactgataa aaacgtcgca       240
gaaggtttgg aagtgtataa cgctgaaaac tgtgacagca ttgtcacttt gggcggcgga       300
agctcgcatg atgctggaaa aggcattgca ttagtagctg ctaacggtgg aacaatttac       360

-continued

```
gattatgaag gtgtcgataa atcaaaaaaa ccaatggtcc cgctcattgc gattaataca    420
acagctggta caggcagtga attaactaga tttacaatca tcacagatac tgaacgtaaa    480
gtgaaaatgg cgattgttga taaacatgta acacctacac tttcaatcaa cgacccagaa    540
ctaatggtcg gaatgcctcc gtctttaaca gctgctactg gattagatgc attaactcat    600
gcaattgaag cttatgtttc aacggctgct actccaatta cagatgcact tgccattcag    660
gcgatcaaaa tcatttctaa atacttgcca cgtgcatttg caaatggcaa agatatggaa    720
gcacgtgagc aaatggcctt cgctcaatca ttagctggta tggcatttaa taacgcttct    780
ttaggctatg ttcatgcaat tgcacaccaa tttggcggat tctacaactt ccctcatggc    840
gtttgcaatg cgatccttct gccacatgta tgccgattta atttaatttc taagtggaa     900 cgttttgcag aaattgctgc tctcctaggt gaaaatgtcg ccggcctaag tactcgcgaa    960
gcagctgaaa aaggtattaa agcgatcgaa agaatggcta agaccttaa cattccaaga    1020 ggctttaaag aactgggtgc taagaagaa gacattgtga ctttagctga aaatgcgatg    1080
aaagatgcaa cggcattaac aaatcctcgt aaacctaagt tggaagaagt tatacaaatt    1140
attaaaaatg ctatgtaa                                                 1158
```

<210> SEQ ID NO 6
<211> LENGTH: 385
<212> TYPE: PRT
<213> ORGANISM: Bacillus methanolicus PB1

<400> SEQUENCE: 6

```
Met Thr Asn Thr Gln Ser Ile Phe Tyr Ile Pro Ser Val Asn Leu Phe
1               5                   10                  15

Gly Pro Gly Ser Val Asn Glu Val Gly Thr Arg Leu Ala Gly Leu Gly
            20                  25                  30

Val Lys Lys Ala Leu Leu Val Thr Asp Ala Gly Leu His Gly Leu Gly
        35                  40                  45

Leu Ser Glu Lys Ile Ala Ser Ile Ile Arg Glu Ala Gly Val Glu Val
    50                  55                  60

Leu Ile Phe Pro Lys Ala Glu Pro Asn Pro Thr Asp Lys Asn Val Ala
65                  70                  75                  80

Glu Gly Leu Glu Val Tyr Asn Ala Glu Asn Cys Asp Ser Ile Val Thr
                85                  90                  95

Leu Gly Gly Gly Ser Ser His Asp Ala Gly Lys Gly Ile Ala Leu Val
            100                 105                 110

Ala Ala Asn Gly Gly Thr Ile Tyr Asp Tyr Glu Gly Val Asp Lys Ser
        115                 120                 125

Lys Lys Pro Met Val Pro Leu Ile Ala Ile Asn Thr Thr Ala Gly Thr
    130                 135                 140

Gly Ser Glu Leu Thr Arg Phe Thr Ile Ile Thr Asp Thr Glu Arg Lys
145                 150                 155                 160

Val Lys Met Ala Ile Val Asp Lys His Val Thr Pro Thr Leu Ser Ile
                165                 170                 175

Asn Asp Pro Glu Leu Met Val Gly Met Pro Pro Ser Leu Thr Ala Ala
            180                 185                 190

Thr Gly Leu Asp Ala Leu Thr His Ala Ile Glu Ala Tyr Val Ser Thr
        195                 200                 205

Ala Ala Thr Pro Ile Thr Asp Ala Leu Ala Ile Gln Ala Ile Lys Ile
    210                 215                 220

Ile Ser Lys Tyr Leu Pro Arg Ala Phe Ala Asn Gly Lys Asp Met Glu
```

```
                225                 230                 235                 240
Ala Arg Glu Gln Met Ala Phe Ala Gln Ser Leu Ala Gly Met Ala Phe
                    245                 250                 255

Asn Asn Ala Ser Leu Gly Tyr Val His Ala Ile Ala His Gln Phe Gly
                260                 265                 270

Gly Phe Tyr Asn Phe Pro His Gly Val Cys Asn Ala Ile Leu Leu Pro
            275                 280                 285

His Val Cys Arg Phe Asn Leu Ile Ser Lys Val Glu Arg Phe Ala Glu
        290                 295                 300

Ile Ala Ala Leu Leu Gly Glu Asn Val Ala Gly Leu Ser Thr Arg Glu
305                 310                 315                 320

Ala Ala Glu Lys Gly Ile Lys Ala Ile Glu Arg Met Ala Lys Asp Leu
                325                 330                 335

Asn Ile Pro Arg Gly Phe Lys Glu Leu Gly Ala Lys Glu Glu Asp Ile
                340                 345                 350

Val Thr Leu Ala Glu Asn Ala Met Lys Asp Ala Thr Ala Leu Thr Asn
            355                 360                 365

Pro Arg Lys Pro Lys Leu Glu Glu Val Ile Gln Ile Ile Lys Asn Ala
        370                 375                 380

Met
385

<210> SEQ ID NO 7
<211> LENGTH: 1149
<212> TYPE: DNA
<213> ORGANISM: Bacillus methanolicus MGA3

<400> SEQUENCE: 7
atgacaacaa acttttcat tccaccagcc agcgtaattg acgcggtgc agtaaaggaa      60 gtaggaacaa gacttaagca aattggagct aagaaagcgc ttatcgttac agatgcattc     120
cttcacagca caggtttatc tgaagaagtt gctaaaaaca ttcgtgaagc tggcgttgat     180
gttgcgattt tcccaaaagc tcaaccagat ccagcagata cacaagttca tgaaggtgta     240
gatgtattca acaagaaaaa ctgtgattca cttgtttcta tcggtggagg tagctctcac     300
gatacagcta aagcaatcgg tttagttgca gcaaacggcg aagaatcaa tgactatcaa     360 ggtgtaaaca gcgtagaaaa accagtcgtt ccagtagttg caatcactac aacagctggt     420
actggtagtg aaacaacatc tcttgcggtt attacagact ctgcacgtaa agtaaaaatg     480
cctgttattg atgagaaaat tactccaact gtagcaattg ttgacccaga attaatggtg     540
aaaaaaccag ctggattaac aatcgcaact ggtatggatg cattgtccca tgcaattgaa     600
gcatatgttg caaaggtgc tacaccagtt actgatgcat tgctattca gcaatgaaa      660 cttatcaatg aatacttacc aaaagcggtt gcgaacggag aagacatcga agcacgtgaa     720
aaaatggctt atgcacaata catggcagga gtggcattta caacggtgg tttaggacta     780 gttcactcta tttctcacca gtaggtgga gtttacaaat acaacacgg aatctgtaac      840 tcagttaata tgccacacgt ttgcgcattc aacctaattg ctaaaactga gcgcttcgca     900
cacattgctg agcttttagg tgagaatgtt gctggcttaa gcactgcagc agctgctgag     960
agagcaattg tagctcttga agaatcaac aaatccttcg gtatcccatc tggctatgca    1020
gaaatgggcg tgaaagaaga ggatatcgaa ttattagcga aaacgcata cgaagacgta    1080 tgtactcaaa gcaaccccacg cgttcctact gttcaagaca ttgcacaaat catcaaaaac    1140
gctatgtaa                                                           1149
```

<210> SEQ ID NO 8
<211> LENGTH: 382
<212> TYPE: PRT
<213> ORGANISM: Bacillus methanolicus MGA3

<400> SEQUENCE: 8

Met Thr Thr Asn Phe Phe Ile Pro Pro Ala Ser Val Ile Gly Arg Gly
1               5                   10                  15

Ala Val Lys Glu Val Gly Thr Arg Leu Lys Gln Ile Gly Ala Lys Lys
            20                  25                  30

Ala Leu Ile Val Thr Asp Ala Phe Leu His Ser Thr Gly Leu Ser Glu
        35                  40                  45

Glu Val Ala Lys Asn Ile Arg Glu Ala Gly Val Asp Val Ala Ile Phe
    50                  55                  60

Pro Lys Ala Gln Pro Asp Pro Ala Asp Thr Gln Val His Glu Gly Val
65                  70                  75                  80

Asp Val Phe Lys Gln Glu Asn Cys Asp Ser Leu Val Ser Ile Gly Gly
                85                  90                  95

Gly Ser Ser His Asp Thr Ala Lys Ala Ile Gly Leu Val Ala Ala Asn
            100                 105                 110

Gly Gly Arg Ile Asn Asp Tyr Gln Gly Val Asn Ser Val Glu Lys Pro
        115                 120                 125

Val Val Pro Val Val Ala Ile Thr Thr Thr Ala Gly Thr Gly Ser Glu
    130                 135                 140

Thr Thr Ser Leu Ala Val Ile Thr Asp Ser Ala Arg Lys Val Lys Met
145                 150                 155                 160

Pro Val Ile Asp Glu Lys Ile Thr Pro Thr Val Ala Ile Val Asp Pro
                165                 170                 175

Glu Leu Met Val Lys Lys Pro Ala Gly Leu Thr Ile Ala Thr Gly Met
            180                 185                 190

Asp Ala Leu Ser His Ala Ile Glu Ala Tyr Val Ala Lys Gly Ala Thr
        195                 200                 205

Pro Val Thr Asp Ala Phe Ala Ile Gln Ala Met Lys Leu Ile Asn Glu
    210                 215                 220

Tyr Leu Pro Lys Ala Val Ala Asn Gly Glu Asp Ile Glu Ala Arg Glu
225                 230                 235                 240

Lys Met Ala Tyr Ala Gln Tyr Met Ala Gly Val Ala Phe Asn Asn Gly
                245                 250                 255

Gly Leu Gly Leu Val His Ser Ile Ser His Gln Val Gly Gly Val Tyr
            260                 265                 270

Lys Leu Gln His Gly Ile Cys Asn Ser Val Asn Met Pro His Val Cys
        275                 280                 285

Ala Phe Asn Leu Ile Ala Lys Thr Glu Arg Phe Ala His Ile Ala Glu
    290                 295                 300

Leu Leu Gly Glu Asn Val Ala Gly Leu Ser Thr Ala Ala Ala Ala Glu
305                 310                 315                 320

Arg Ala Ile Val Ala Leu Glu Arg Ile Asn Lys Ser Phe Gly Ile Pro
                325                 330                 335

Ser Gly Tyr Ala Glu Met Gly Val Lys Glu Glu Asp Ile Glu Leu Leu
            340                 345                 350

Ala Lys Asn Ala Tyr Glu Asp Val Cys Thr Gln Ser Asn Pro Arg Val
        355                 360                 365

Pro Thr Val Gln Asp Ile Ala Gln Ile Ile Lys Asn Ala Met

<210> SEQ ID NO 9
<211> LENGTH: 1152
<212> TYPE: DNA
<213> ORGANISM: Bacillus methanolicus PB1

<400> SEQUENCE: 9

```
atgacgcaaa gaaactttt cattccacca gctagcgtaa ttggacgcgg cgctgtaaaa      60
gaagtaggaa caagacttaa gcaaattgga gctacaaaag cacttatcgt tacagatgca    120
tttcttcatg gcacaggttt gtcagaagaa gttgctaaaa acattcgtga agctggcctt    180
gatgctgtaa tttttcccaaa agctcaacca gatccagcag atacacaagt tcatgaaggc    240
gtagatatat caaacaaga aaatgtgat gcacttgttt ctatcggtgg aggtagctct    300
cacgatacag caaagcaat cggtttagtt gcagcaaacg gcggaagaat caacgactat    360
caaggtgtaa acagtgtaga aaaccggtt gttccagtag ttgcaatcac tacaacagct    420
ggtactggta gtgaaacaac atctcttgcg gttattacag attctgcacg taaagtaaaa    480
atgccagtta tcgatgagaa aattacacca actgtagcaa tgttgaccc agaattaatg    540
gtgaaaaaac cagctggatt aacaattgca actggtatgg atgcattatc ccatgcaatt    600
gaagcatatg ttgcaaaacg tgctacacca gttactgatg cgtttgcaat tcaagcaatg    660
aaactcatta tgaatactt accacgtgcg gttgcaaatg gagaagacat cgaagcacgt    720
gaagcaatgg cttatgcaca atacatggca ggagtggcat ttaacaacgg aggtttagga    780
ttagtacact ctatttctca ccaagtaggt ggagtttaca gttacaaca cggaatctgt    840
aactcagtta atatgccaca cgtttgccaa ttcaacttaa ttgctcgtac tgaacgcttc    900
gcacacattg ctgagcttt aggcgagaat gtttctggct taagcactgc atctgctgct    960
gagagagcaa ttgtagcgct tcaacgctat aacaaaaact tcggtatccc atctggctat   1020
gcagaaatgg gcgtaaaaga agaggatatc gaattattag cgaacaacgc gtaccaagac   1080
gtatgtactc tagataaccc acgtgttcct actgttcaag acattgcaca aatcatcaaa   1140
aacgctctgt aa                                                       1152
```

<210> SEQ ID NO 10
<211> LENGTH: 383
<212> TYPE: PRT
<213> ORGANISM: Bacillus methanolicus PB1

<400> SEQUENCE: 10

```
Met Thr Gln Arg Asn Phe Phe Ile Pro Pro Ala Ser Val Ile Gly Arg
1               5                   10                  15

Gly Ala Val Lys Glu Val Gly Thr Arg Leu Lys Gln Ile Gly Ala Thr
            20                  25                  30

Lys Ala Leu Ile Val Thr Asp Ala Phe Leu His Gly Thr Gly Leu Ser
        35                  40                  45

Glu Glu Val Ala Lys Asn Ile Arg Glu Ala Gly Leu Asp Ala Val Ile
    50                  55                  60

Phe Pro Lys Ala Gln Pro Asp Pro Ala Asp Thr Gln Val His Glu Gly
65                  70                  75                  80

Val Asp Ile Phe Lys Gln Glu Lys Cys Asp Ala Leu Val Ser Ile Gly
                85                  90                  95

Gly Gly Ser Ser His Asp Thr Ala Lys Ala Ile Gly Leu Val Ala Ala
            100                 105                 110
```

Asn Gly Gly Arg Ile Asn Asp Tyr Gln Gly Val Asn Ser Val Glu Lys
            115                 120                 125

Pro Val Pro Val Val Ala Ile Thr Thr Thr Ala Gly Thr Gly Ser
    130                 135                 140

Glu Thr Thr Ser Leu Ala Val Ile Thr Asp Ser Ala Arg Lys Val Lys
145                 150                 155                 160

Met Pro Val Ile Asp Glu Lys Ile Thr Pro Thr Val Ala Ile Val Asp
                165                 170                 175

Pro Glu Leu Met Val Lys Lys Pro Ala Gly Leu Thr Ile Ala Thr Gly
            180                 185                 190

Met Asp Ala Leu Ser His Ala Ile Glu Ala Tyr Val Ala Lys Arg Ala
        195                 200                 205

Thr Pro Val Thr Asp Ala Phe Ala Ile Gln Ala Met Lys Leu Ile Asn
    210                 215                 220

Glu Tyr Leu Pro Arg Ala Val Ala Asn Gly Glu Asp Ile Glu Ala Arg
225                 230                 235                 240

Glu Ala Met Ala Tyr Ala Gln Tyr Met Ala Gly Val Ala Phe Asn Asn
                245                 250                 255

Gly Gly Leu Gly Leu Val His Ser Ile Ser His Gln Val Gly Gly Val
            260                 265                 270

Tyr Lys Leu Gln His Gly Ile Cys Asn Ser Val Asn Met Pro His Val
        275                 280                 285

Cys Gln Phe Asn Leu Ile Ala Arg Thr Glu Arg Phe Ala His Ile Ala
    290                 295                 300

Glu Leu Leu Gly Glu Asn Val Ser Gly Leu Ser Thr Ala Ser Ala Ala
305                 310                 315                 320

Glu Arg Ala Ile Val Ala Leu Gln Arg Tyr Asn Lys Asn Phe Gly Ile
                325                 330                 335

Pro Ser Gly Tyr Ala Glu Met Gly Val Lys Glu Asp Ile Glu Leu
            340                 345                 350

Leu Ala Asn Asn Ala Tyr Gln Asp Val Cys Thr Leu Asp Asn Pro Arg
        355                 360                 365

Val Pro Thr Val Gln Asp Ile Ala Gln Ile Ile Lys Asn Ala Leu
    370                 375                 380

<210> SEQ ID NO 11
<211> LENGTH: 1152
<212> TYPE: DNA
<213> ORGANISM: Bacillus methanolicus PB1

<400> SEQUENCE: 11
atgactaaaa caaaattttt cattccatca tccactgtat ttggacgagg cgctgtaaag     60
gaagtaggtg caagactaaa agctattgga gctacgaaag cacttatcgt tacagacgca    120
ttccttcaca gcacaggttt gtcagaagaa gttgctaaaa acattcgtga agctggcctt    180
gatgttgtaa ttttttccta agctcaacca gatccagcag atacacaagt tcatgaaggc    240
gtagaggtat tcaaacaaga aaaatgtgat gcacttgttt ctatcggtgg gggcagctct    300
cacgatacag caaaaggaat cggcttagtt gcagcaaacg gcggaagaat caacgactat    360
caaggtgtaa atagtgtaga aaacaagtc gttccacaga ttgcaatcac tacaacagct    420
ggtactggaa gtgaaacaac atctcttgcg gttattacag actctgcacg taaagtaaaa    480
atgccggtta ttgatgaaaa attaacacca actgtagcaa ttgttgaccc agaattaatg    540
gtgaaaaaac cagctggatt aacaatagca actggtatgg atgcattatc ccatgcaatt    600

-continued

```
gaagcatatg ttgcaaaacg tgctacacca gttactgatg catttgcgat tcaagcaatg    660
aaactcatta atgaatactt accaaaagcg gttgcaaatg agaagacat cgaagcacgt     720 gaagcaatgg cttatgcaca atacatggca ggagtggcat ttaataacgg aggtttagga    780
ttagtacact ctatttctca ccaagtaggt ggagtttaca aattacaaca cggaatctgt    840
aactcagttg taatgccaca tgtttgccaa ttcaacttaa ttgctcgtac tgaacgcttc    900
gcacacattg ctgagctttt aggcgagaat gtttctggct taagcactgc atctgctgca    960
gaaagaacaa ttgcagcgct tgaacgctac aacagaaact tcggtattcc atcaggctat   1020
aaagcaatgg gcgtaaaaga agaagatatc gaattattag caaacaacgc aatgcaagat   1080
gtatgtactc tagacaaccc tcgtgtccct acggttcaag acattcaaca aatcatcaaa   1140
aacgctctgt aa                                                       1152
```

<210> SEQ ID NO 12
<211> LENGTH: 383
<212> TYPE: PRT
<213> ORGANISM: Bacillus methanolicus PB1

<400> SEQUENCE: 12

```
Met Thr Lys Thr Lys Phe Phe Ile Pro Ser Ser Thr Val Phe Gly Arg
1               5                   10                  15

Gly Ala Val Lys Glu Val Gly Ala Arg Leu Lys Ala Ile Gly Ala Thr
            20                  25                  30

Lys Ala Leu Ile Val Thr Asp Ala Phe Leu His Ser Thr Gly Leu Ser
        35                  40                  45

Glu Glu Val Ala Lys Asn Ile Arg Glu Ala Gly Leu Asp Val Val Ile
    50                  55                  60

Phe Pro Lys Ala Gln Pro Asp Pro Ala Asp Thr Gln Val His Glu Gly
65                  70                  75                  80

Val Glu Val Phe Lys Gln Glu Lys Cys Asp Ala Leu Val Ser Ile Gly
                85                  90                  95

Gly Gly Ser Ser His Asp Thr Ala Lys Gly Ile Gly Leu Val Ala Ala
            100                 105                 110

Asn Gly Gly Arg Ile Asn Asp Tyr Gln Gly Val Asn Ser Val Glu Lys
        115                 120                 125

Gln Val Val Pro Gln Ile Ala Ile Thr Thr Thr Ala Gly Thr Gly Ser
    130                 135                 140

Glu Thr Thr Ser Leu Ala Val Ile Thr Asp Ser Ala Arg Lys Val Lys
145                 150                 155                 160

Met Pro Val Ile Asp Glu Lys Ile Thr Pro Thr Val Ala Ile Val Asp
                165                 170                 175

Pro Glu Leu Met Val Lys Lys Pro Ala Gly Leu Thr Ile Ala Thr Gly
            180                 185                 190

Met Asp Ala Leu Ser His Ala Ile Glu Ala Tyr Val Ala Lys Arg Ala
        195                 200                 205

Thr Pro Val Thr Asp Ala Phe Ala Ile Gln Ala Met Lys Leu Ile Asn
    210                 215                 220

Glu Tyr Leu Pro Lys Ala Val Ala Asn Gly Glu Asp Ile Glu Ala Arg
225                 230                 235                 240

Glu Ala Met Ala Tyr Ala Gln Tyr Met Ala Gly Val Ala Phe Asn Asn
                245                 250                 255

Gly Gly Leu Gly Leu Val His Ser Ile Ser His Gln Val Gly Gly Val
            260                 265                 270
```

```
Tyr Lys Leu Gln His Gly Ile Cys Asn Ser Val Val Met Pro His Val
        275                 280                 285

Cys Gln Phe Asn Leu Ile Ala Arg Thr Glu Arg Phe Ala His Ile Ala
        290                 295                 300

Glu Leu Leu Gly Glu Asn Val Ser Gly Leu Ser Thr Ala Ser Ala Ala
305                 310                 315                 320

Glu Arg Thr Ile Ala Ala Leu Glu Arg Tyr Asn Arg Asn Phe Gly Ile
                325                 330                 335

Pro Ser Gly Tyr Lys Ala Met Gly Val Lys Glu Glu Asp Ile Glu Leu
            340                 345                 350

Leu Ala Asn Asn Ala Met Gln Asp Val Cys Thr Leu Asp Asn Pro Arg
        355                 360                 365

Val Pro Thr Val Gln Asp Ile Gln Gln Ile Ile Lys Asn Ala Leu
    370                 375                 380

<210> SEQ ID NO 13
<211> LENGTH: 30
<212> TYPE: DNA
<213> ORGANISM: Artificial sequence
<220> FEATURE:
<223> OTHER INFORMATION: con16_rev primer

<400> SEQUENCE: 13
aaccatggat gaggaggatg tttgtatgac                                    30

<210> SEQ ID NO 14
<211> LENGTH: 31
<212> TYPE: DNA
<213> ORGANISM: Artificial sequence
<220> FEATURE:
<223> OTHER INFORMATION: con18_rev primer

<400> SEQUENCE: 14
aaccatggca acaaagggg atgtatgtat g                                   31

<210> SEQ ID NO 15
<211> LENGTH: 27
<212> TYPE: DNA
<213> ORGANISM: Artificial sequence
<220> FEATURE:
<223> OTHER INFORMATION: con41_rev primer

<400> SEQUENCE: 15
aggatcccct ccgttttgtc gtattac                                       27

<210> SEQ ID NO 16
<211> LENGTH: 28
<212> TYPE: DNA
<213> ORGANISM: Artificial sequence
<220> FEATURE:
<223> OTHER INFORMATION: con43_rev primer

<400> SEQUENCE: 16
tggatcctct tcgtctttgg cgaattac                                      28

<210> SEQ ID NO 17
<211> LENGTH: 26
<212> TYPE: DNA
<213> ORGANISM: Artificial sequence
<220> FEATURE:
<223> OTHER INFORMATION: mdh_fwd-MGA3 primer

<400> SEQUENCE: 17
```
catatgacaa caaactttttt cattcc					26

<210> SEQ ID NO 18
<211> LENGTH: 29
<212> TYPE: DNA
<213> ORGANISM: Artificial sequence
<220> FEATURE:
<223> OTHER INFORMATION: mdh_rev-MGA3 primer

<400> SEQUENCE: 18
ctcgagcata gcgttttttga tgatttgtg					29

<210> SEQ ID NO 19
<211> LENGTH: 23
<212> TYPE: DNA
<213> ORGANISM: Artificial sequence
<220> FEATURE:
<223> OTHER INFORMATION: mdh2_fwd-MGA3 primer

<400> SEQUENCE: 19
catatgacaa acactcaaag tgc					23

<210> SEQ ID NO 20
<211> LENGTH: 28
<212> TYPE: DNA
<213> ORGANISM: Artificial sequence
<220> FEATURE:
<223> OTHER INFORMATION: mdh2_rev-MGA3 primer

<400> SEQUENCE: 20
ctcgagcatc gcattttttaa taatttgg					28

<210> SEQ ID NO 21
<211> LENGTH: 30
<212> TYPE: DNA
<213> ORGANISM: Artificial sequence
<220> FEATURE:
<223> OTHER INFORMATION: mdh3_fwd-MGA3 primer

<400> SEQUENCE: 21
catatgaaaa acactcaaag tgcattttac					30

<210> SEQ ID NO 22
<211> LENGTH: 29
<212> TYPE: DNA
<213> ORGANISM: Artificial sequence
<220> FEATURE:
<223> OTHER INFORMATION: mdh_rev-MGA3 primer

<400> SEQUENCE: 22
ctcgagcata gcgttttttga tgatttgtg					29

<210> SEQ ID NO 23
<211> LENGTH: 25
<212> TYPE: DNA
<213> ORGANISM: Artificial sequence
<220> FEATURE:
<223> OTHER INFORMATION: act_fwd-MGA3 primer

<400> SEQUENCE: 23
aaacatatgg gaaaattatt tgagg					25

<210> SEQ ID NO 24
<211> LENGTH: 30
<212> TYPE: DNA
<213> ORGANISM: Artificial sequence

```
<220> FEATURE:
<223> OTHER INFORMATION: act_rev-MGA3 primer

<400> SEQUENCE: 24
aaactcgagt ttatttttga gagcctcttg                                              30

<210> SEQ ID NO 25
<211> LENGTH: 31
<212> TYPE: DNA
<213> ORGANISM: Artificial sequence
<220> FEATURE:
<223> OTHER INFORMATION: mdh_fwd-PB1 primer

<400> SEQUENCE: 25
atacatatga cgcaaagaaa ctttttcatt c                                            31

<210> SEQ ID NO 26
<211> LENGTH: 30
<212> TYPE: DNA
<213> ORGANISM: Artificial sequence
<220> FEATURE:
<223> OTHER INFORMATION: mdh_rev-PB1 primer

<400> SEQUENCE: 26
atactcgagc agagcgtttt tgatgatttg                                              30

<210> SEQ ID NO 27
<211> LENGTH: 31
<212> TYPE: DNA
<213> ORGANISM: Artificial sequence
<220> FEATURE:
<223> OTHER INFORMATION: mdh1_fwd-PB1 primer

<400> SEQUENCE: 27
atacatatga ctaaaacaaa attttttcatt c                                           31

<210> SEQ ID NO 28
<211> LENGTH: 33
<212> TYPE: DNA
<213> ORGANISM: Artificial sequence
<220> FEATURE:
<223> OTHER INFORMATION: mdh2_fwd-PB1 primer

<400> SEQUENCE: 28
atacatatga caaacactca aagtatattt tac                                          33

<210> SEQ ID NO 29
<211> LENGTH: 36
<212> TYPE: DNA
<213> ORGANISM: Artificial sequence
<220> FEATURE:
<223> OTHER INFORMATION: mdh2_rev-PB1 primer

<400> SEQUENCE: 29
atactcgagc atagcatttt taataatttg tataac                                       36

<210> SEQ ID NO 30
<211> LENGTH: 29
<212> TYPE: DNA
<213> ORGANISM: Artificial sequence
<220> FEATURE:
<223> OTHER INFORMATION: act_frw-PB1 primer

<400> SEQUENCE: 30
ttttcatatg ggaaaattat ttgaggaaa                                               29
```

<210> SEQ ID NO 31
<211> LENGTH: 31
<212> TYPE: DNA
<213> ORGANISM: Artificial sequence
<220> FEATURE:
<223> OTHER INFORMATION: act_rev-PB1 primer

<400> SEQUENCE: 31
ttttctcgag tttatttttg agagcctctt g                                31

<210> SEQ ID NO 32
<211> LENGTH: 35
<212> TYPE: DNA
<213> ORGANISM: Artificial sequence
<220> FEATURE:
<223> OTHER INFORMATION: nudF-fwd primer

<400> SEQUENCE: 32
ttttcatatg aaatcattag aagaaaaaac aattg                            35

<210> SEQ ID NO 33
<211> LENGTH: 30
<212> TYPE: DNA
<213> ORGANISM: Artificial sequence
<220> FEATURE:
<223> OTHER INFORMATION: nudF-rev primer

<400> SEQUENCE: 33
ttttctcgag tttttgtgct tggagcgctt                                  30

<210> SEQ ID NO 34
<211> LENGTH: 20
<212> TYPE: DNA
<213> ORGANISM: Artificial sequence
<220> FEATURE:
<223> OTHER INFORMATION: mdh-MGA3 fwd primer

<400> SEQUENCE: 34
attccaccag ccagcgtaat                                             20

<210> SEQ ID NO 35
<211> LENGTH: 26
<212> TYPE: DNA
<213> ORGANISM: Artificial sequence
<220> FEATURE:
<223> OTHER INFORMATION: mdh-MGA3 rev primer

<400> SEQUENCE: 35
cttagctcca atttgcttaa gtcttg                                      26

<210> SEQ ID NO 36
<211> LENGTH: 26
<212> TYPE: DNA
<213> ORGANISM: Artificial sequence
<220> FEATURE:
<223> OTHER INFORMATION: mdh2-MGA3 fwd primer

<400> SEQUENCE: 36
ggatacatgt caaacactca aagtgc                                      26

<210> SEQ ID NO 37
<211> LENGTH: 31
<212> TYPE: DNA
<213> ORGANISM: Artificial sequence
<220> FEATURE:
<223> OTHER INFORMATION: mdh2-MGA3 rev primer

```
<400> SEQUENCE: 37
tctagacacc atcgcatttt taataatttg g                                    31

<210> SEQ ID NO 38
<211> LENGTH: 26
<212> TYPE: DNA
<213> ORGANISM: Artificial sequence
<220> FEATURE:
<223> OTHER INFORMATION: mdh3-MGA3 fwd primer

<400> SEQUENCE: 38
ggatacatgt aaaacactca aagtgc                                          26

<210> SEQ ID NO 39
<211> LENGTH: 34
<212> TYPE: DNA
<213> ORGANISM: Artificial sequence
<220> FEATURE:
<223> OTHER INFORMATION: mdh3-MGA3 rev primer

<400> SEQUENCE: 39
tctagacacc atagcatttt taataatttg gatg                                 34

<210> SEQ ID NO 40
<211> LENGTH: 21
<212> TYPE: DNA
<213> ORGANISM: Artificial sequence
<220> FEATURE:
<223> OTHER INFORMATION: mdh-PB1 fwd primer

<400> SEQUENCE: 40
tccaccagct agcgtaattg g                                               21

<210> SEQ ID NO 41
<211> LENGTH: 22
<212> TYPE: DNA
<213> ORGANISM: Artificial sequence
<220> FEATURE:
<223> OTHER INFORMATION: mdh-PB1 rev primer

<400> SEQUENCE: 41
aacctgtgcc atgaagaaat gc                                              22

<210> SEQ ID NO 42
<211> LENGTH: 21
<212> TYPE: DNA
<213> ORGANISM: Artificial sequence
<220> FEATURE:
<223> OTHER INFORMATION: mdh1-PB1 fwd primer

<400> SEQUENCE: 42
tccatcatcc actgtatttg g                                               21

<210> SEQ ID NO 43
<211> LENGTH: 21
<212> TYPE: DNA
<213> ORGANISM: Artificial sequence
<220> FEATURE:
<223> OTHER INFORMATION: mdh1-PB1 rev primer

<400> SEQUENCE: 43
acctgtgctg tgaaggaatg c                                               21

<210> SEQ ID NO 44
```

```
<211> LENGTH: 23
<212> TYPE: DNA
<213> ORGANISM: Artificial sequence
<220> FEATURE:
<223> OTHER INFORMATION: mdh2-PB1 fwd primer

<400> SEQUENCE: 44
cgtgaagctg gtgtggaagt att                                              23

<210> SEQ ID NO 45
<211> LENGTH: 20
<212> TYPE: DNA
<213> ORGANISM: Artificial sequence
<220> FEATURE:
<223> OTHER INFORMATION: mdh2-PB1 rev primer

<400> SEQUENCE: 45
tccaaacctt ctgcgacgtt                                                  20
```

METHANOL DEHYDROGENASE ENZYMES FROM *BACILLUS*

CROSS-REFERENCE TO RELATED APPLICATION(S)

This application is a National Phase Patent Application and claims priority to and the benefit of International Application Number PCT/EP2013/051516, filed on Jan. 25, 2013, which claims priority to British Patent Application Number 1201178.9, filed on Jan. 25, 2012, the entire contents of all of which are incorporated herein by reference.

SEQUENCE LISTING

The instant application contains a Sequence Listing which was previously submitted in ASCII format to WIPO and is hereby incorporated by reference in its entirety. Said ASCII copy, last modified on Feb. 11, 2013, is named eolf-seq1.txt and is 36,564 bytes in size.

The present invention relates to previously unknown methanol dehydrogenase (MDH) enzymes identified in methylotrophic bacteria, and in particular concerns novel MDH-encoding genes identified in *Bacillus methanolicus* MGA3 and *Bacillus methanolicus* PB1. The invention is based on the surprising finding that multiple MDH isoforms exist in these strains of *B. methanolicus* which differ in their biochemical properties. Such novel genes encoding previously unknown MDH isoforms may be used in the genetic engineering of host microorganisms, for example in the context of utilisation of methanol and/or other C1 compounds as a growth substrate. Thus the novel genes/enzymes may be used to introduce or modify, e.g. enable/enhance MDH activity in a host microorganism.

Methylotrophic microorganisms can utilize one-carbon (C1) sources such as methane and methanol as their sole sources for energy and biomass generation and there exists a variety of different enzymes and pathways for C1 metabolism among methylotrophs. A number of Gram-positive thermotolerant bacilli with ability to grow on methanol at temperatures up to 60° C. have been isolated and classified as *Bacillus methanolicus*. *B. methanolicus* is a so-called restricted methylotroph which implies that it can utilize few multicarbon sources for energy and growth. Scientific interest in these organisms has mainly been focused on their potential as cell factories for industrial production of amino acids, notably L-lysine and L-glutamate, from methanol at elevated temperatures, but their potential use as hosts for production of other useful products, including vitamins, cytochromes, coenzymes and recombinant proteins has also been proposed.

*B. methanolicus* MGA3 (ATCC53907) was originally isolated from soil samples in Minnesota (Schendel, Bremmon et al. (1990) Appl Environ Microbiol 56(4): 963-970) and it has been a major model strain used for metabolic engineering of this bacterium (Brautaset, Jakobsen et al. (2007) Appl Microbiol Biotechnol 74(1): 22-34; Jakobsen, Brautaset et al. (2009) Appl Environ Microbiol 75(3): 652-661; Brautaset, Jakobsen et al. (2010) Appl Microbiol Biotechnol 87(3): 951-964). *B. methanolicus* has several unique traits including a NAD-dependent methanol dehydrogenase (MDH) for methanol oxidation (de Vries, Arfman et al. (1992) J Bacteriol 174(16): 5346-5353; Arfman, Hektor et al. (1997) Eur J Biochem 244(2): 426-433; Hektor, Kloosterman et al. (2002) J Biol Chem 277(49): 46966-46973). The activity of methanol dehydrogenase (MDH) is a key attribute for methylotrophic growth and is involved in the first step of methanol fermentation, namely the oxidation of methanol to formaldehyde.

Formaldehyde is an intermediate in methanol metabolism and the detoxification of this cell-toxic metabolite is therefore very important. Formaldehyde can be assimilated via the RuMP pathway. Also a linear dissimilatory pathway for the direct conversion of formaldehyde into $CO_2$ has been proposed. The dissimilatory pathways are assumed to be important for the overall energy generation in the cells upon growth on methanol. Together with the RuMP pathway, the dissimilatory pathways may also play roles in regulating formaldehyde below toxic levels in the cells. Therefore, efficient methanol oxidation and concomitant formaldehyde assimilation is of crucial importance for growth and energy flow into the primary metabolism and for production of desired products. In addition, all this has to be carefully balanced in order to ensure efficient conversion of methanol and at the same time avoiding toxic accumulation of formaldehyde in the cells. In this regard, MDH plays a crucial role in bacterial methylotrophy.

Bacterial MDHs can be divided into groups according to their reaction mechanisms and use of a cofactor(s). The most studied is the two-subunit pyrroloquinoline quinone (PQQ)-dependent quinoprotein MDHs, widely found in Gram-negative methylotrophic bacteria. Gram-positive methylotrophy commonly encode $NAD(P)^+$-dependent methanol dehydrogenases and in addition to the MDH from strain MGA3 discussed above, an $NAD^+$-dependant MDH has been identified in another strain of *B. methanolicus* strain C1 (Vonck, Arfman et at (1991) J Biol Chem 266(6): 3949-3954; de Vries, Arfman et al. (1992) J Bacteriol 174(16): 5346-5353). The *B. methanolicus* MDH displays primary sequence similarity to iron containing alcohol dehydrogenases, and has therefore been classified with the family III of NAD-dependent alcohol dehydrogenases. The enzyme is composed of ten identical subunits that each contains a tightly, but non-covalently, bound NAD(H) molecule in addition to a $Zn^{2+}$-ion and 1-2 $Mg^{2+}$-ions Methylotrophy in *B. methanolicus* has been found to be plasmid-dependent and involves the concerted recruitment of both plasmid and chromosomal genes. Work in *B. methanolicus* MGA3 has identified a natural plasmid pBM19 carrying mdh and five RuMP pathway genes; curing of pBM19 results in loss of ability to grow on methanol. In work leading up to the present invention, and not previously reported, a corresponding analogous plasmid, designated pBM20, has been shown in the physiologically very different alternative model strain PB1 (NCIMB 13113).

NAD-dependent MDH enzymes have been shown to be catalytically activated by the activator protein Act which is classified within the nudix hydrolase family.

Methanol oxidation is a major bottleneck in attempts to engineer methylotrophy in host microorganisms. Indeed, even in the context of host organisms which are naturally methylotrophic, e.g. *B. methanolicus*, modification of MDH activity or expression may be beneficial in improving growth and/or yield of desired products. There is therefore a continuing need for MDH enzymes, and in particular novel mdh genes which may be used for genetic engineering of organisms, especially such genes encoding novel enzymes having altered or improved properties with respect to MDH enzymes of the art, for example improved activity or stability, or which may in any way be beneficial to use in the genetic modification of desired hosts.

With a view to better understanding the physiology of the methylotrophic host cell *B. methanolicus*, the present inventors have sequenced the genome of MGA3 and the alternative wild-type strain PB1. Surprisingly, in the course of this sequencing it has been found that both strains possess multiple MDH iso forms; in both strains three genes encoding three separate NAD-dependent MDH proteins have been identified. Thus, in *B. methanolicus* MGA3, in addition to the previously reported plasmid-encoded mdh-MGA3 gene, two new genes, termed herein mdh2-MGA3 and mdh3-MGA3, have been identified. Interestingly, these new mdh genes are chromosomally located. In *B. methanolicus* PB1, three new genes, termed herein mdh-PB1, mdh1-PB1 and mdh2-PB1, the first plasmid borne (on plasmid pBM20) and the latter two chromosomal, have been identified. All these genes have been recombinantly expressed, purified and characterized biochemically in vitro. Whilst displaying some similarities, it became clear that these different MDH enzymes may have different properties, which includes their activity. Based on these studies, and in particular the sequence analysis, two distinct MDH sub-families have been identified.

The first sub-family includes the previously described plasmid-borne mdh gene of strain MGA3 (mdh-MGA3), and two genes from strain PB1, mdh-PB1 and mdh1-PB1 (mdh-PB1 being plasmid borne and mhd1-PB1 being chromosomal) and is identified herein as the "mdh/mdh1-type family". The second sub-family includes the novel chromosomal genes mdh2-MGA3, mdh3-MGA3 and mdh2-PB1 and is identified herein as the "mdh2/mdh3-type family". It is this latter family which forms the subject of the present invention.

The members of the mdh2/mdh3-type family have at least 90% sequence identity to each other at the DNA level (see FIG. 1) and at the amino acid sequence level with respect to the encoded proteins (see FIG. 2). In particular, the coding sequences of mdh2-MGA3 (SEQ ID NO. 1) and mdh3-MGA3 (SEQ ID NO.3) share 96% DNA sequence identity and the deduced polypeptides Mdh2-MGA3 (SEQ ID NO.2) and Mdh3-MGA3 (SEQ ID NO.4) share 96% amino acid identity (see FIG. 2B). The deduced Mdh2-PB1 polypeptide (SEQ ID NO. 6) is 91% identical to the deduced Mdh2-MGA3 polypeptide (SEQ ID NO.2) and 92% identical to the deduced Mdh3-MGA3 polypeptide (SEQ ID NO.4) (see FIG. 2B).

On the other hand, sequence identity between members of the two different sub-families is much lower, in the region of 60-66%. For example, the mdh2-MGA3 coding sequence (SEQ ID NO. 1) is 65% identical to the mdh-MGA3 coding sequence (SEQ ID NO. 7) and the deduced Mdh2-MGA3 polypeptide (SEQ ID NO.2) is 61% identical to the deduced Mdh-MGA3 polypeptide (SEQ ID NO.8). The coding sequence of the mdh3-MGA3 gene (SEQ ID NO. 3) is 66% identical to the coding sequence of mdh-MGA3 (SEQ ID NO.7) and the deduced Mdh3 polypeptide (SEQ ID NO. 4) is 62% identical to Mdh-MGA3 (SEQ ID NO. 8).

As noted above, biochemical characterisation studies have revealed differences between the MDH enzymes of the mdh2/mdh3-type family and those of the mdh/mdh1-type family. For example, Mdh3-MGA3 (SEQ ID NO. 4) and Mdh2-PB1 (SEQ ID NO. 6) have improved thermostability. Differences in substrate specificity and in the level of activity on different alcohol substrates have also been observed. This opens up the possibility to use such enzymes in the oxidation of different alcohols (e.g. ethanol or propanol) and not just methanol.

Studies have also been performed to express the genes heterologously in different non-methylotrophic hosts. These studies establish the utility of the new mdh2/mdh3-type family sequences of the invention in genetic engineering of a range of different host cells to introduce MDH activity and thereby enable methanol utilisation. It is proposed that the present invention has broad applicability insofar as different host cells are concerned and in the studies described herein two biotechnologically well characterized and phylogenetically very diverse bacterial host strains have been used, i.e. the Gram-negative *Escherichia coli*, and the Gram-positives *Bacillus subtilis*, and each genetically modified host microorganism has been shown to display increased MDH activity when modified to express the novel MDH enzymes of the present invention, specifically enzymes from the mdh2/mdh3-type family from *B. methanolicus* MGA3 and *B. methanolicus* PB1.

Notably results presented herein show that different particular enzymes may exhibit improved activity in different hosts. For example, for expression of MDH activity in the host *E. coli*, Mdh2-MGA3 (SEQ ID NO. 1) gave the best results. The choice of MDH enzyme may also depend on the circumstances of the expression and the precise nature of the host cell and/or culture conditions, for example, whether and if so which particular act gene is co-expressed. Thus, the new enzymes of the invention and their coding sequences advantageously provide a new and expanded repertoire of MDH enzymes and encoding nucleic acid molecules for use in the oxidation of alcohols, including methanol, and in particular for use in the genetic modification of host cells, (e.g. for the production of recombinant host cells), for example to introduce or modify alcohol dehydrogenase activity in a host cell, particularly MDH activity, or to introduce methylotrophy into a host cell. As described further below, nucleic acid molecules encoding the new enzymes of the present invention may be used alone or in combination.

Accordingly, in a first aspect the present invention provides a nucleic acid molecule, particularly an isolated nucleic acid molecule, which encodes a polypeptide (or protein) having alcohol dehydrogenase activity, in particular methanol dehydrogenase activity, comprising or having (e.g. consisting of) a nucleotide sequence selected from the group consisting of:
(i) a nucleotide sequence as set forth in any one of SEQ ID NO:s 1 (mdh2-MGA3), 3 (mdh3-MGA3), or 5 (mdh2-PB1);
(ii) a nucleotide sequence having at least 90% sequence identity, more particularly at least 91, 92, 93, 94, 95, 96, 97, 98 or 99% sequence identity, with a nucleotide sequence as set forth in any one of SEQ ID NOs: 1, 3 or 5:
(iii) a nucleotide sequence which is degenerate with any one of the nucleotide sequences of SEQ ID NOs: 1, 3 or 5;
(iv) a nucleotide sequence which is a part of the nucleotide sequence of any one of SEQ ID NO.s 1, 3 or 5, or of a nucleotide sequence which is degenerate with a sequence of SEQ ID NOs: 1, 3 or 5;
(v) a nucleotide sequence encoding all or part of a polypeptide whose amino acid sequence is set forth in any one of SEQ ID NOs: 2 (Mdh2-MGA3), 4 (Mdh3-MGA3) or 6 (Mdh2-PB1); and
(vi) a nucleotide sequence encoding all or part of a polypeptide which has an amino acid sequence having at least 90% sequence identity, preferably at least 91, 92, 93, 94, 95, 96, 97, 98 or 99% sequence identity, with an amino acid sequence as set forth in any one of SEQ ID NOs: 2, 4 or 6;
or a nucleic acid molecule comprising a nucleotide sequence which is complementary to the nucleotide sequence of any one of (i) to (vi).

In a further aspect the present invention provides a polypeptide having alcohol dehydrogenase activity, in particular methanol dehydrogenase activity, and comprising or having (e.g. consisting of) a sequence of amino acids selected from the group consisting of:
(i) all or part of an amino acid sequence as set forth in any one of SEQ ID NOs: 2, 4 or 6; and
(ii) all or part of an amino acid sequence having at least 90% sequence identity, preferably at least 91, 92, 93, 94, 95, 96, 97, 98 or 99% sequence identity, with an amino acid sequence as set forth in any one of SEQ ID NOs: 2, 4 or 6.

The nucleic acid molecules of the present invention advantageously allow for the introduction or modification of alcohol dehydrogenase, and in particular MDH, activity in a host organism. This may be achieved by modifying the organism to express one or more nucleic acid molecules of the invention. As noted above, said nucleic acid molecules may be obtained, or derived from the mdh genes of strains of *B. methanolicus*, in particular the MGA3 and PB1 strains. In a particular embodiment, nucleic acid molecules encoding, or derived from nucleic acid molecules encoding, different MDH enzymes (e.g. different isoenzymes or enzymes from different strains, or different polypeptide variants etc.) may be used in combination. Thus two or more different nucleic acid molecules may be co-expressed.

The present invention thus provides a method for introducing or modifying MDH activity in a host organism by the expressing in said organism one or more nucleic acid molecules of the invention. In particular, the nucleic acid molecule may be heterologous, or non-native to the host organism. It may be expressed under the control of a native or non-native promoter.

Accordingly in a still further aspect the present invention provides a method for introducing or modifying alcohol dehydrogenase activity, and in particular MDH activity, in a host organism, said method comprising introducing into said organism a nucleic acid molecule of the invention as hereinbefore defined and growing (or culturing) said organism under conditions in which said nucleic acid molecule is expressed.

It will be seen that in this aspect, the invention can also be seen to provide a method for producing a polypeptide(s) having alcohol dehydrogenase activity, and in particular MDH activity, said method comprising introducing into a host organism a nucleic acid molecule of the invention as hereinbefore defined and growing (or culturing) said organism under conditions in which said polypeptide(s) is produced. The host organism may be an organism which does not natively (e.g. in its wild-type) possess MDH activity (i.e. does not have or possess an endogenous MDH), and hence in such an embodiment the invention provides for the introduction of MDH activity into a host. Alternatively viewed, in such an embodiment the host may be modified to introduce the ability to convert methanol to formaldehyde, or in other words to modify a host to allow the initial step of C1-carbon source utilisation, particularly methanol utilisation.

In an alternative embodiment the host organism may have or possess an endogenous MDH enzyme, and the method of the invention may therefore involve modifying MDH activity in such a host by introducing a nucleic acid molecule encoding further or additional MDH enzyme, which may for example be heterologous to the host. Also encompassed is the over-expression of MDH activity in a host organism by introducing into said organism a nucleic acid molecule encoding a native MDH enzyme (i.e. in which the introduced nucleic acid molecule encodes an endogenous MDH enzyme).

The modified host organism may be cultured or grown using any desirable carbon source as a substrate, including but not limited to methanol or a higher alcohol. A method of the invention may thus in one embodiment comprise culturing or growing a host organism which contains one or more exogenously-introduced MDH-encoding nucleic acid molecules as defined herein.

In yet another aspect, the present invention provides a host organism which has been modified to introduce a nucleic acid molecule of the invention as hereinbefore defined.

In particular, in this aspect of the invention the nucleic acid molecule which is introduced comprises a nucleotide sequence which is heterologous to the host organism. The heterologous sequence may be the nucleotide sequence encoding the alcohol dehydrogenase (e.g. MDH) polypeptide or it may be a heterologous expression control sequence or some other sequence (e.g. vector or marker sequence). In the case of a host organism which endogenously expresses an alcohol dehydrogenase enzyme, the modified host may be distinguished from the non-modified host organism by containing a further copy of the nucleic acid molecule encoding the alcohol dehydrogenase polypeptide. In other words it may contain more copies of the encoding nucleotide sequence than an unmodified host.

As mentioned above, the nucleic acid molecules encoding the novel MDH enzymes of the present invention may be obtained, e.g. isolated or cloned, from *B. methanolicus*, in particular the MGA3 and PB1 strains. Thus, the MDH enzyme may be Mdh2 or Mdh3 from MGA3 (SEQ ID NOs: 2 or 4 respectively), or Mdh2 from PB1 (SEQ ID NO: 6). However, in addition to the specific native ("wild-type") sequences indicated above, also included are variants of these sequences which have at least 90% nucleotide sequence identity thereto and which retain alcohol dehydrogenase, and particularly MDH, activity. Such variants may include natural variants, e.g. different variants which may occur in the strains in nature or which may be obtained from other strains of *B. methanolicus*, and which encode MDH polypeptides which are functionally equivalent to the MDH polypeptides of SEQ ID NOs. 2, 4 or 6. Alternatively, the variants may be synthetic or artificial variants, e.g. obtained or derived by modification (e.g. mutation) of the amino acid sequences of SEQ ID NOs. 2, 4 or 6 or the nucleotide sequences of SEQ ID NOs. 1, 3 or 5. As noted above combinations of two or more different nucleic acid molecules of the invention may be used. A nucleic acid molecule of the invention may alternatively comprise two or more different nucleotide sequences encoding a polypeptide having alcohol dehydrogenase activity, as defined herein, or a complement thereof. Modifications may be selected on the basis of improved methanol dehydrogenase activity of the corresponding variant or alternatively may be constructed on the basis of protein design algorithms using molecular structures or models to predict improved enzymatic activity.

The MDH polypeptide of the present invention may also include a polypeptide encoded by a fragment (part) of the nucleotide sequence of SEQ ID NOs. 1, 3 or 5, or may comprise or consist of a fragment (or part) of the amino acid sequence of SEQ ID NOs. 2, 4 or 6. A "part" of a nucleotide or amino acid sequence of the invention may include or comprise at least 50, 55, 60, 65, 70, 75, 80, 81, 82, 83, 84, 85, 86, 87, 88, 89, 90, 91, 92, 93, 94, 95, 96, 97, 98 or 99% or more contiguous nucleotides or amino acids of the sequence.

The host organism may be any suitable host organism, but in particular will be a microbial host organism (i.e. a microorganism). It may be any prokaryotic organism, but particularly will be a bacterium. Any gram positive or gram negative bacterium may be used, but particular mention may be made of the following classes or genera: *Escherichia, Corynebacterium* and *Bacillus*. Representative host organisms include *E. coli, B. subtilis* and *C. glutamicum*. As noted above, *B. methanolicus* or other methylotrophic host organisms may also be used, for example, *Methylomonas, Methylobacillus, Methylobacterium, Methylophilus* or *Methylococcus*. However, the present invention is not limited to these organisms and extends to any microbial host.

*C. glutamicum* is a rod shaped, nonpathogenic and Gram-positive soil bacterium. It grows under aerobic and anaerobic conditions and is biotin auxotroph. *C. glutamicum* is capable of growing on a variety of substrates as single or combined sources of carbon and energy. Among the substrates metabolized are sugars like glucose, fructose or sucrose and organic acids such as L-lactate and acetate. Furthermore, *C. glutamicum* is able to grow on ethanol as the sole carbon. It is widely used for the large-scale industrial production of the amino acids L-glutamate and L-lysine. Recent metabolic engineering studies have shown that *C. glutamicum* is also able to produce a variety of other commercially interesting compounds, e.g. other L-amino acids, D-amino acids, diamines such as cadaverine or putrescine, organic acids like succinate and bio fuels such as ethanol or isobutanol.

According to the present invention, one or more nucleic acid molecules of the invention may be expressed in the host organism, including in particular at least one heterologous nucleic acid molecule (that is a nucleic acid molecule comprising a nucleotide sequence which is heterologous to the host), and in particular comprising a heterologous sequence encoding an MDH polypeptide. Thus, the host organism may be modified to express one or more copies of a nucleic acid molecule or alternatively may be modified to express one or more copies of a number of different nucleic acid molecules of the invention.

Thus, the microorganism which is modified (or "engineered") to express MDH according to the present invention will contain an exogenously-introduced MDH-encoding nucleic acid molecule as defined herein. In other words, the organism may be transformed with such a MDH-encoding nucleic acid molecule and may be regarded as a transgenic or recombinant organism. As noted above, the nucleic acid molecule may encode a MDH enzyme which is homologous or heterologous (i.e. native or non-native) to that host. Thus, a further copy (or more) of a gene which is native to the host may be introduced. The nucleic acid molecule which is introduced may comprise a nucleotide sequence derived from the native gene, or from a different source.

The MDH may be expressed in combination with other enzymes to allow new features of the organism.

"Expression" as used herein refers to the transcription of a nucleotide sequence into mRNA and consequent translation of said mRNA into a polypeptide product.

As referred to herein, "overexpressing" means that expression of the nucleotide sequence is increased as compared to, or relative to, the level of expression occurring in an organism which has not been modified according to the invention. Expression may be considered in terms of the amount of polypeptide product (e.g. MDH enzyme) produced, which may be determined by any convenient method known in the art. For example, expression can be determined by measuring protein activity (i.e. the activity of the expressed MDH polypeptide). Alternatively, the amount of protein produced can be measured to determine the level of expression, for example Western Blotting or other antibody detection systems, or indeed by any method of assessing or quantifying protein. Realtime PCR may also be used. The assay may be an in vivo or in vitro assay.

Activity may be determined by assaying for alcohol dehydrogenase activity by procedures known in the art and described in the literature, for example as detailed in the Examples below. MDH activity of an encoded protein may for example catalyse the conversion of methanol to formaldehyde and said activity is defined herein as the amount of enzyme needed to produce 1 μmol NADH per minute for which various alcohols may be used a substrate, e.g. ethanol, methanol, propanol, butanol, pentanol, hexanol, isopropanol and 1,3-propanediol. Alcohol dehydrogenase activities may be measured spectrophotometrically as described previously by Hektor et al. (2002; Chem 277(49): 46966-46973).

An alcohol dehydrogenase polypeptide may be expressed, or over-expressed, by any means known in the art, such as by introducing a nucleic acid molecule comprising a nucleotide sequence encoding a MDH polypeptide, e.g. a copy of a native gene, for example expressed from a stronger or unregulated promoter relative to the native gene, and/or by introducing multiple copies of a MDH-encoding nucleic acid molecule.

The organism may also be engineered to introduce additional or alternative regulatory elements.

In a particular embodiment, a MDH-encoding nucleic acid molecule may be expressed from a non-native or heterologous promoter (that is a promoter which is heterologous to the MDH-encoding nucleotide sequence, i.e. is not the native MDH gene promoter) and particularly a strong, non-native or heterologous promoter. Thus, in a particular embodiment, the MDH-encoding gene is not used with its native promoter. A MDH-encoding gene may be introduced which is under the control of a non-native promoter. As referred to herein, a strong promoter is one which expresses a gene at a high level, or at least at a higher level than affected by its native promoter. The term "strong promoter" is a term well known and widely used in the art and many strong promoters are known in the art, or can be identified by routine experimentation. Alternatively, the promoter is an mdh promoter of *B. methanolicus*. However, the choice of promoter is not particularly limited.

Alternatively, a MDH gene may be expressed using a native promoter. The invention encompasses the use of a microorganism which may endogenously express a mdh gene or one which does not. In the case of the former, one or more additional copies of the native gene or a variant thereof or of another MDH or encoding nucleic acid molecule may be introduced, and these may be introduced under the control of a native or non-native promoter. With a native promoter a multi-copy vector may for example be used. In the case of the latter, a MDH (or encoding nucleic acid molecule) is introduced which is heterologous to that host, but which may be under the control of a promoter which is native or non-native to the MDH gene from which the encoding nucleic acid molecule is derived.

Methods for introducing genes or nucleic acid molecules are well known in the art and widely described in the literature and any desired method may be used. The gene (nucleic acid molecule) may thus be introduced using a vector, which may be an autonomously-replicating vector or a vector which allows the gene (nucleic acid molecule) to be integrated into the host genome (e.g. chromosome). The gene (nucleic acid molecule) to be expressed may thus be introduced into an expression vector and the expression vector may then be introduced into the host cell. Methods for constructing expression vectors and introducing them into host cells are well known in the art. Conveniently, the gene encoding MDH may be introduced using a plasmid vector and a host microorganism may be transformed with the plasmid, e.g. by electroporation. The choice of method may depend on the microorganism used. Methods for introducing nucleic acids and vectors into microorganisms are well known and widely described in the literature.

The nucleic acid molecule preferably encodes a polypeptide or protein which is a MDH or a part thereof having MDH activity.

Preferably, the nucleic acid molecule as defined in parts (i) to (vi) above encodes a polypeptide or protein having or retaining the function or activity or properties of the MDH polypeptide as defined by the amino acid sequences of any one of SEQ ID NOs. 2, 4, or 6.

The terms "polypeptide" and "protein" are used interchangeably herein and include any length of amino acid chain (i.e. any polymer or oligomer of amino acids).

As noted above, the invention extends to parts or functional fragments of the nucleotide sequences defined above, by which it is meant parts or fragments that encode a protein or polypeptide which has the same or substantially the same activity as the full length protein as defined above. Tests to determine whether a protein/polypeptide encoded by such a part or fragment has the same or substantially the same activity (e.g. catalytic or enzymatic activity) as the full length polypeptide/protein as defined above include those discussed above. Normally parts or functional fragments of nucleic acid molecules will only have small deletions relative to the full length nucleic acid molecule, e.g. deletions of less than 50, 40, 30, 20 or 10 nucleotides, for example at the 5' end encoding the N-terminus of the protein, the 3' end encoding the C-terminus of the protein or internally within the encoding region, although larger deletions e.g. of at least 60, 70, 80, 90, 100, 150, 200, 300, 400, 500, 600 or 700 nucleotides, or deletions of less than 60, 70, 80, 90, 100, 150, 200, 300, 400, 500, 600 or 700 nucleotides can also be carried out, if the fragment has the same or substantially the same activity (e.g. catalytic or enzymatic activity) as the full length protein as defined above. The activity of the encoded polypeptide or protein can readily be tested to determine whether it shares the same activity as the full length polypeptide or protein, e.g. as set out above.

Representative parts or fragments may comprise at least 50%, and preferably at least 60, 70, 75, 80, 85, 90 or 95% contiguous nucleotides of the nucleotide sequence as set forth in SEQ ID NOs. 1, 3 or 5. Exemplary part or fragment sizes include at least 620, 700, 800, 850, 900, 950, 1000, 1050, 1100 and 1150 nucleotides.

Shorter fragments of the nucleic acid molecule of the invention can be used as probes, e.g. for PCR or hybridisation protocols. Shorter fragments can be e.g. 10-30, 20-25 nucleotides in length. Such probes are useful in protocols for identifying further nucleic acid molecules which share homology with the nucleic acid molecules of the invention.

The term "nucleic acid molecule" as used herein refers to a polymer of RNA or DNA that is single or double stranded, optionally including synthetic, non-natural or altered nucleotide bases. Examples of such polynucleotides include cDNA, genomic DNA and dsRNA, inter alia. Preferably, the nucleic acid molecule is DNA.

Whilst the nucleic acid sequences referred to herein comprise thymidine ("t") nucleotides, it will be understood that the invention also relates to corresponding sequences wherein thymidine is replaced by uridine ("u").

As noted above, the invention includes nucleic acid molecules which are variants of the nucleic acid molecules of SEQ ID NOs. 1, 3 or 5, particularly functionally equivalent variants. The "variant" nucleic acid molecules may thus have single or multiple nucleotide changes compared to the nucleic acid molecules of SEQ ID NOs. 1, 3 or 5. For example, the variants might have 1, 2, 3, 4, or 5 or more nucleotide additions, substitutions, insertions or deletions.

In a further aspect, the invention provides a protein (or polypeptide) having alcohol dehydrogenase, particularly MDH, activity, as hereinbefore defined.

The protein or polypeptide preferably is a MDH or a part thereof having MDH activity. More particularly the part retains the function or activity of properties of the MDH from which it derives (as defined by reference to the amino acid sequence of SEQ ID NOs. 2, 4 or 6).

The protein or polypeptide may alternatively be defined with reference to the encoding nucleic acid sequences and as such the protein or polypeptide of the invention can be encoded by any of the nucleic acid molecules of the invention, as described above.

The invention extends to functional parts or fragments of the full length protein molecules, by which it is meant parts or fragments which have the same or substantially the same activity as the full length proteins as defined above, i.e. they should be considered to be functionally equivalent variants. As noted elsewhere herein, the property can be tested for in various ways in a straightforward manner. Normally these functional fragments will only have small deletions relative to the full length protein molecule, e.g. of less than 50, 40, 30, 20 or 10 amino acids, although as noted above in connection with nucleic acid molecules larger deletions e.g. of up to 60, 70, 80, 90, 100, 150, 200 amino acids or at least 60, 70, 80, 90, 100, 150, 200 amino acids, may be appropriate. In all cases, the fragments should have the same or substantially the same activity as the full length proteins as defined above, i.e. they should be considered to be functionally equivalent variants. These deletions may be at the N terminus, the C terminus or they may be internal deletions.

Representative parts or fragments may comprise at least 50%, and preferably at least 60, 70, 75, 80, 85, 90 or 95% contiguous amino acids of the amino acid sequence as set forth in SEQ ID NOs. 2, 4 or 6.

The polypeptide of the invention as defined above thus include variants of the sequences of SEQ ID NOs. 2, 4 or 6, e.g. sequences having certain levels of sequence identity to the recited sequences. Such variants could be naturally occurring variants, such as comparable proteins or homologues found in other species or more particularly variants found within other microorganisms, (which share the functional properties of the encoded protein as defined elsewhere herein).

Variants of the naturally occurring polypeptides as defined herein can also be generated synthetically e.g. by using standard molecular biology techniques that are known in the art, for example standard mutagenesis techniques such as site-directed or random mutagenesis (e.g. using gene shuffling or error prone PCR). Such mutagenesis techniques can be used to develop enzymes which have improved or different catalytic properties.

Derivatives of the polypeptides as defined herein may also be used. By derivative is meant a polypeptide as described above or a variant thereof which instead of the naturally occurring amino acid, contains a structural analogue of that amino acid. Derivatisation or modification (e.g. labelling, glycosylation, methylation of the amino acids in the protein) may also occur as long as the function of the protein is not adversely affected.

By "structural analogue", it is meant a non-standard amino acid. Examples of such non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids, D-N-methylamino acids.

Sequence identity may be assessed by any convenient method. However, for determining the degree of sequence identity between sequences, computer programs that make multiple alignments of sequences are useful, for instance Clustal W (Thompson et al., (1994) Nucleic Acids Res., 22:

4673-4680). Programs that compare and align pairs of sequences, like ALIGN (Myers et al., (1988) CABIOS, 4: 11-17), FASTA (Pearson et al., (1988) PNAS, 85:2444-2448; Pearson (1990), Methods Enzymol., 183: 63-98) and gapped BLAST (Altschul et al., (1997) Nucleic Acids Res., 25: 3389-3402) are also useful for this purpose. Furthermore, the Dali server at the European Bioinformatics institute offers structure-based alignments of protein sequences (Holm (1993) J. Mol. Biol., 233: 123-38; Holm (1995) Trends Biochem. Sci., 20: 478-480; Holm (1998) Nucleic Acid Res., 26: 316-9).

Multiple sequence alignments and percent identity calculations may be determined using the standard BLAST parameters, (using sequences from all organisms available, matrix Blosum 62, gap costs: existence 11, extension 1). Alternatively, the following program and parameters may be used: Program: Align Plus 4, version 4.10 (Sci Ed Central Clone Manager Professional Suite). DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

A further embodiment of the invention provides a construct, e.g. a recombinant construct, comprising a nucleic acid molecule of the invention as defined herein operably linked to a heterologous expression control sequence. In this context it will be understood that the expression control sequence will be heterologous (i.e. non-native) to the nucleic acid molecule, more particularly heterologous to the nucleotide sequence which encodes the alcohol dehydrogenase polypeptide. In this regard where the encoding nucleotide sequence is not a naturally-occurring sequence, the expression control sequence will be heterologous to the nucleotide sequence from which it is derived. As noted above, combinations of different nucleic acid molecules may be used.

Such an expression control sequence will typically be a promoter. Accordingly the construct will preferably comprise a non-native promoter, particularly a strong, non-native promoter. Optionally, the construct may additionally contain a further one or more genes, and/or one or more suitable regulatory sequences. The optional further one or more genes may be under the control of the same promoter as the MDH-encoding nucleic acid molecule of the invention. The optional one or more regulatory sequences may be non-native regulatory sequences (that is non-native with respect to the encoding nucleotide sequence, or nucleotide sequence)

In the context of this invention, the term "operably linked" refers to the association of two or more nucleic acid molecules on a single nucleic acid fragment so that the function of one is affected by the other. For example, a promoter is operably linked with a coding sequence when it is capable of affecting the expression of that coding sequence (i.e. the coding sequence is under the transcriptional control of the promoter). Coding sequences may be operably linked to regulatory sequences in sense or antisense orientation.

The term "regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, operators, enhancers and translation leader sequences. As used herein, the term "promoter" refers to a nucleotide sequence capable of controlling the expression of a coding sequence or RNA. In general, a coding sequence is located 3' to a promoter sequence. Promoters may be derived in their entirety from a native gene, or be composed of different elements derived from different promoters found in nature, or even comprise synthetic nucleotide segments. It is further recognized that since in most cases the exact boundaries of regulatory sequences have not been completely defined, nucleic acid fragments of different lengths may have identical promoter activity.

A further embodiment of the invention provides a vector comprising a nucleic acid molecule or construct as defined herein.

More particularly, vectors comprising one or more of the MDH-encoding nucleic acid molecules of the invention (or construct of the invention) may be constructed. The choice of vector may be dependent upon the host microorganism, the method that will be used to transform host cells, the method that is used for protein expression, or on another intended use of the vector. The skilled person is well aware of the genetic elements that must be present in a vector in order successfully to transform, select and propagate host cells containing an MDH-encoding nucleic acid molecule or construct of the invention. The skilled person will also recognize that different independent transformation events will result in different levels and patterns of expression and thus that multiple events may need to be screened in order to obtain cells displaying the desired expression level and pattern. Such screening may be accomplished by Southern analysis of DNA, Northern analysis of mRNA expression, Western analysis of protein expression, inter alia.

The invention further provides a microorganism or host, which may be any host organism as discussed above e.g. *E. coli, B. subtilis* and *C. glutamicum*, containing one or more of the nucleic acid molecules, constructs or vectors of the invention. The host is genetically manipulated so as to introduce or alter the expression of MDH. This can be achieved by introducing one or more copies of a MDH-encoding nucleic acid of the invention under the control of a non-native, preferably strong, promoter. Thus genetic material is present in the host organism that is not present in naturally-occurring organism (i.e. exogenous genetic material is present).

In general, the exogenous genetic material is introduced using the process of transformation. Transformation will typically involve a plasmid or other vector which will also contain a gene to enable identification of successfully transformed microorganisms, e.g. a gene for antibiotic resistance (for example against ampicillin) or some other marker. Other methods for selecting transformants are known to the skilled person and include the use of a light sensitive vector, a lux-gene, which causes positive colonies to light up in the dark. Other suitable vehicles for transformation of the bacteria include cosmids and bacteriophage molecules.

The invention will now be further described with reference to the following non-limiting Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. All documents referenced herein are incorporated by reference.

In the Examples reference is made to the following Figures:

FIG. 1: Nucleotide sequence alignments for *B. methanolicus* mdh-MGA3, mdh2-MGA3, mdh3-MGA3, mdh-PB1, mdh1-PB1 and mdh2-PB1.

FIG. 2: (A) Primary sequence alignments of the deduced *B. methanolicus* MGA3 Mdh, Mdh2 and Mdh3 and PB1 Mdh, Mdh1 and Mdh2 proteins. (B) Primary sequence alignments mdh2/mdh3 sub-family (i.e. *B. methanolicus* MGA3 Mdh2 and Mdh3 and PB1 Mdh2 proteins).

FIG. 3. Catalytic activities of purified Mdh (black), Mdh2 (dark grey) and Mdh3 (light grey) on various alcohols (200 mM) tested in vitro. (A) Substrate specificity was analysed for MDHs from *B. methanolicus* MGA3 in vitro. Alcohol substrates were used at concentrations of 500 mM except for pentanol (300 mM) and hexanol (50 mM). The data were calculated from the mean value from two experiments which were done in triplicate. (B) Substrate specificity for MDHs from *B. methanolicus* PB1 was analysed in vitro. Alcohol substrates were used at concentrations of 500 mM except for pentanol (300 mM) and hexanol (50 mM). The data were calculated from the mean value from two experiments which were done in triplicate.

FIG. 4. (A) Determination of temperature optimum for catalytic activity of Mdh, Mdh2 and Mdh3 in vitro. (B) Determination of optimal temperature conditions for the catalysis by MDH proteins from *B. methanolicus* PB1 was carried out in vitro: the specific activity was calculated for 500 mM ethanol; measurements were done in triplicate.

FIG. 5. (A) Temperature stability of MGA3 Mdh, Mdh2 and Mdh3 was tested in vitro. Enzymes were incubated at 45° C. or at 60° C. prior to the enzyme assay. (B) Temperature stability of PB1 Mdh, Mdh1 and Mdh2 was tested in vitro. Enzymes were incubated at 45° C. or at 60° C. prior to the enzyme assay.

FIG. 6. The catalytic activity of Mdh, Mdh2 and Mdh3 was tested in the presence of Act and compared to the level of activity measured when Act was not present. (A) Activation of MDHs with Act from *B. methanolicus* MGA3 was tested in vitro. Tests were performed as triplicates with 500 mM alcohol and 5 μg/ml MDH and Act proteins. (B) Activation of MDHs with Act from *B. methanolicus* PB1 was tested in vitro. Tests were performed as triplicates with 500 mM alcohol and 5 μg/ml MDH and Act proteins.

FIG. 7. (A) Cloning strategies. (B) Physical map of act-pHCMC04 plasmid.

Figure 8:
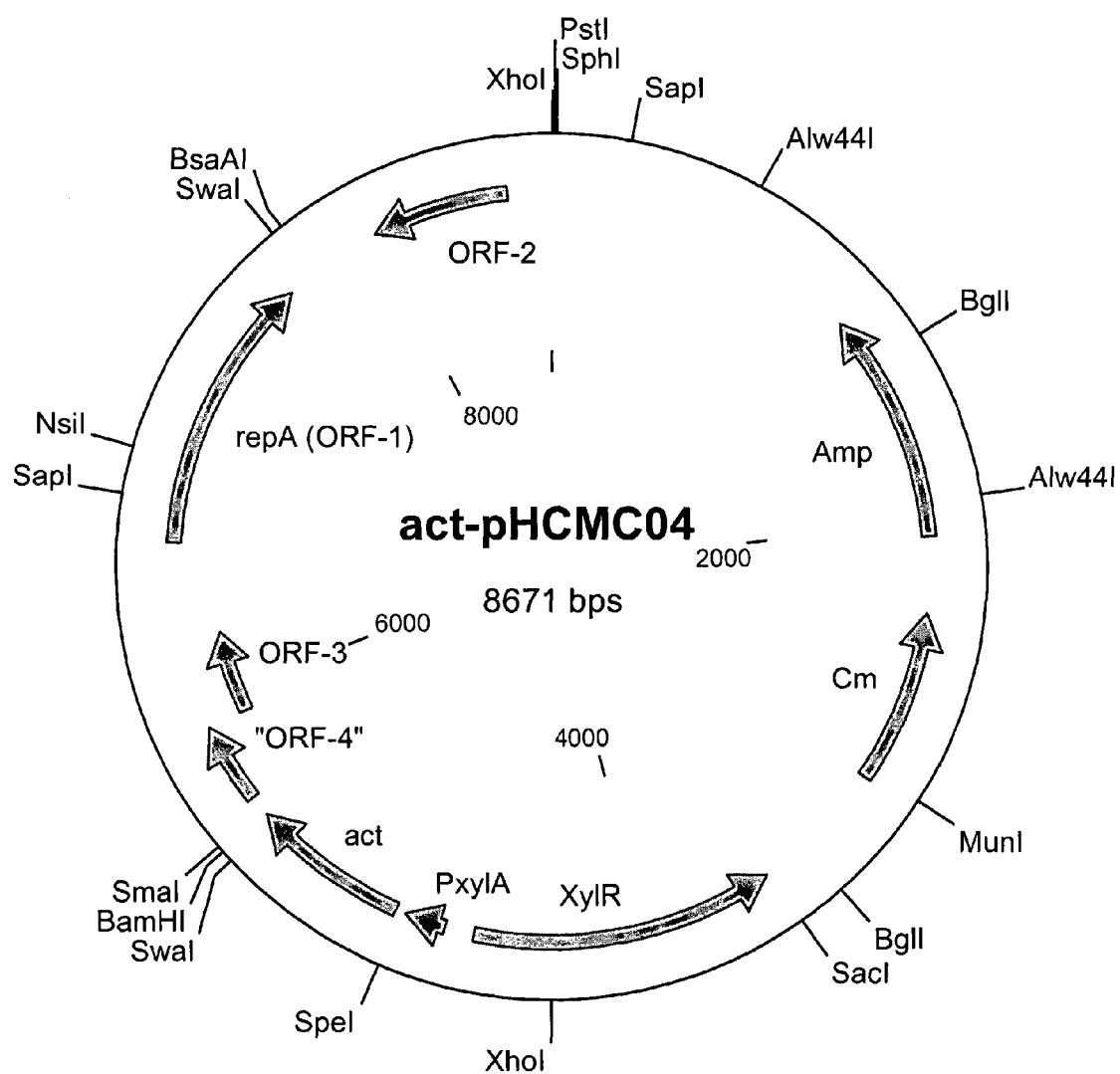

FIG. 8. In vitro activities of recombinant *B. subtilis* strains when tested using ethanol and methanol as substrates.

Figure 9:
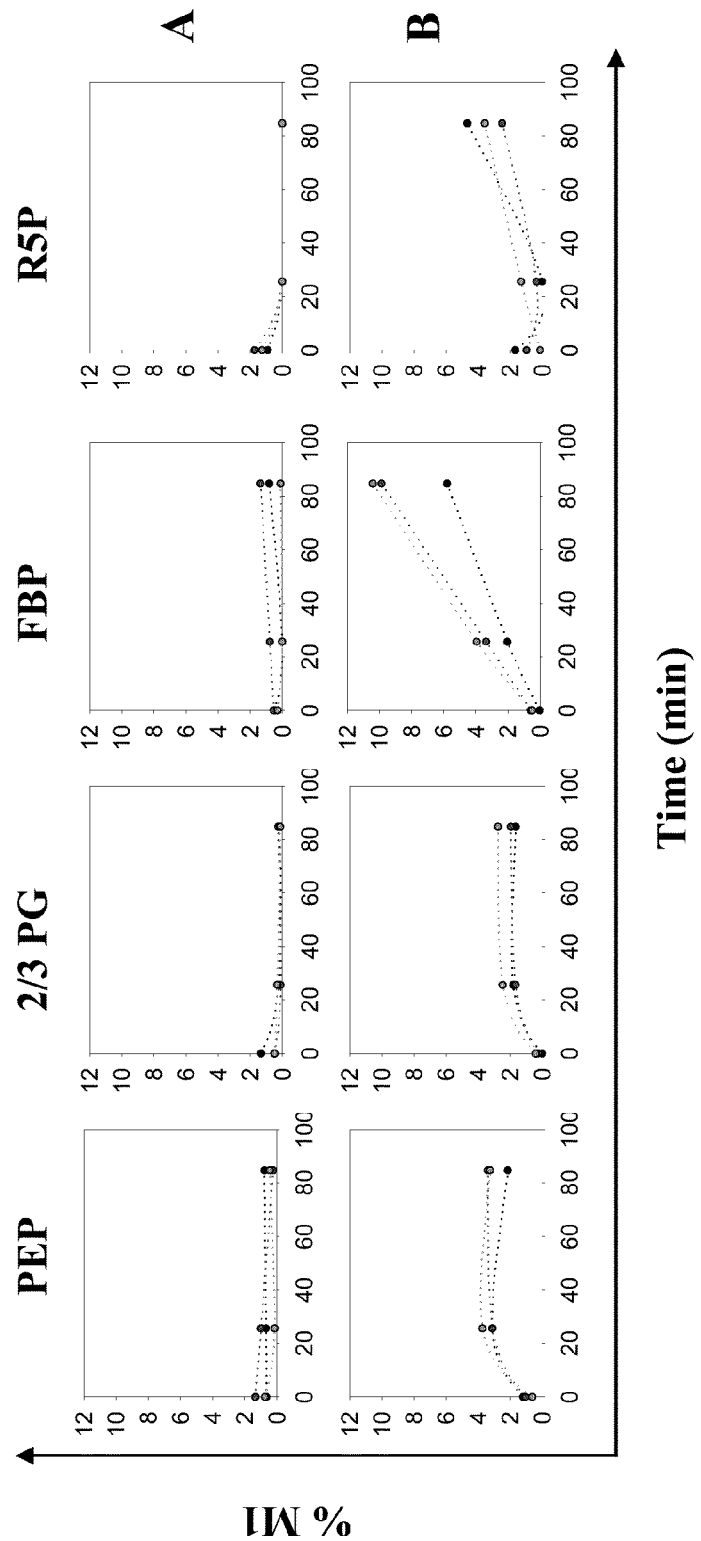

FIG. 9. % of mass isotopomer fraction M1 of different metabolites before (i.e. time zero point) and after (i.e. 30 and 90 minutes time points) $^{13}C$-methanol addition. The three lines represent the results from three independent biological replicates. A: *C. glutamicum* delta ald pEKEX3; B: *C. glutamicum* delta ald strain that expresses Mdh2 (pVWEx1-Mdh2), Hps and Phi (pEKEX3-Hps+Phi). PEP: phosphoenolpyruvate; ⅔ P: 2- and 3-phosphoglycerate; FBP: fructose-bis-phosphate; RSP: ribose-5-phosphate.

Figure 10:
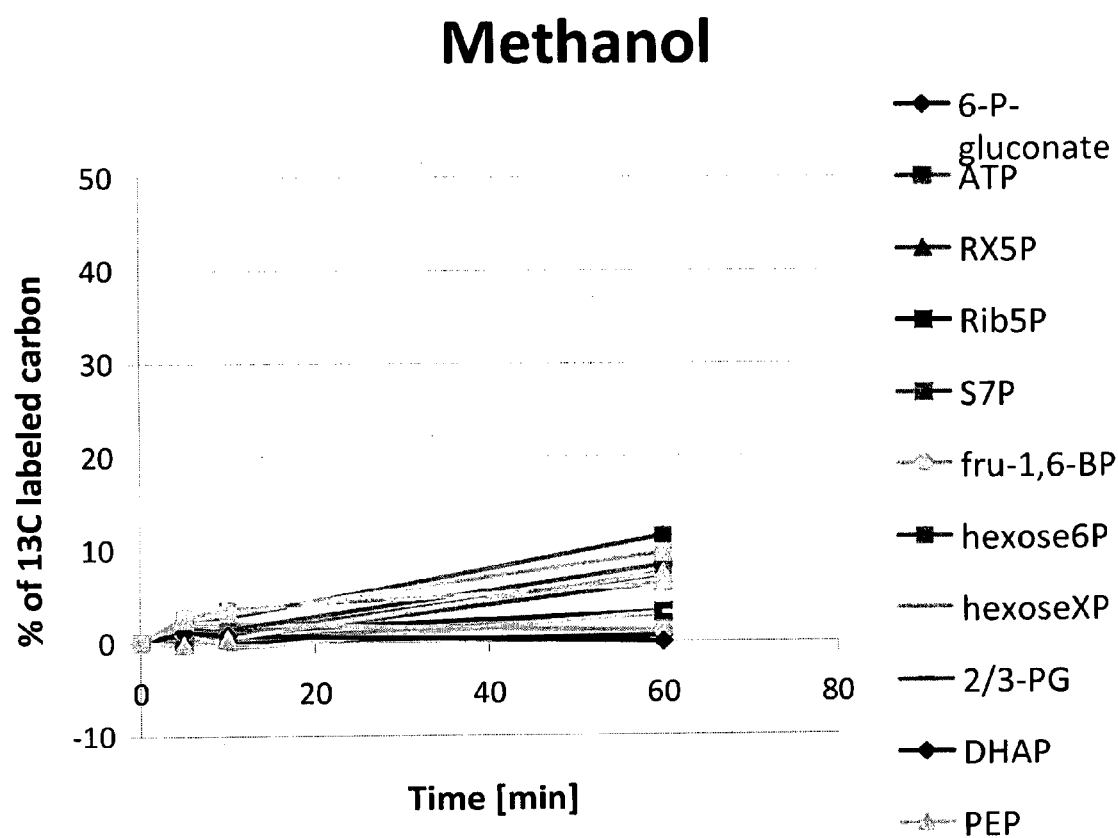

FIG. 10. Metabolic labeling using $^{13}C$ methanol or $^{13}C$ formaldehyde as a substrate. (A) ΔfrmA cells expressing mdh2 and hps phi with $^{13}C$ methanol as a carbon source. (B) ΔfrmA cells expressing hps and phi with $^{13}C$ formaldehyde as a carbon source.

Figure 11:
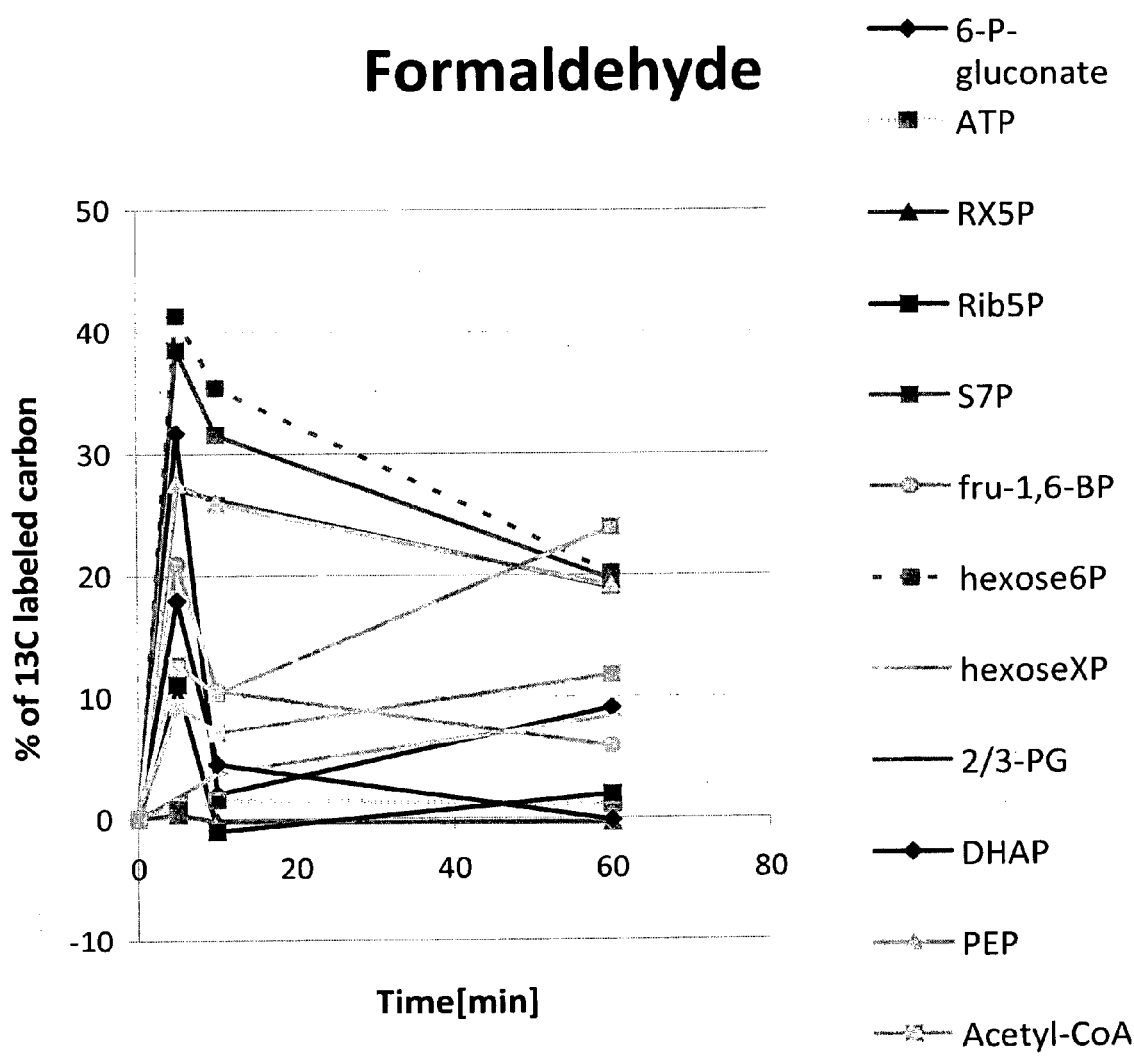

FIG. 11. Building up of the synthetic operon. Each consecutive gene is introduced in the SwaI/BglII restriction sites. The last gene in the operon contains the His$_6$-tag. For the $^{13}C$-labeling experiments (see Example 18) the AMAhxlB- and AMABGFTPrpe-pHCMC04 plasmids were used. RBS: ribosomal binding site.

Figure 12:
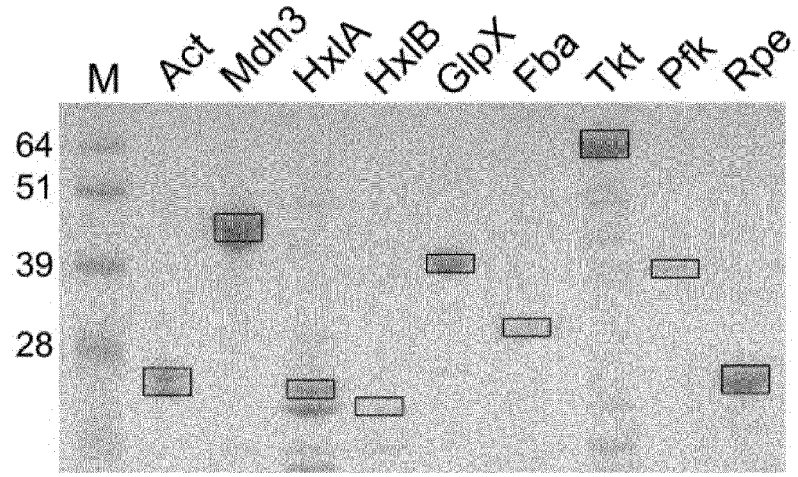

FIG. 12. SDS-PAGE of purified proteins expressed in *B. subtilis* 168. *B. subtilis* strains were used that contained any one of the constructs shown in FIG. 11. Proteins were purified using a HisTrap column and concentrated using Vivaspin columns. Protein bands are indicated in boxes. M: Molecular weight marker.

Figure 13:
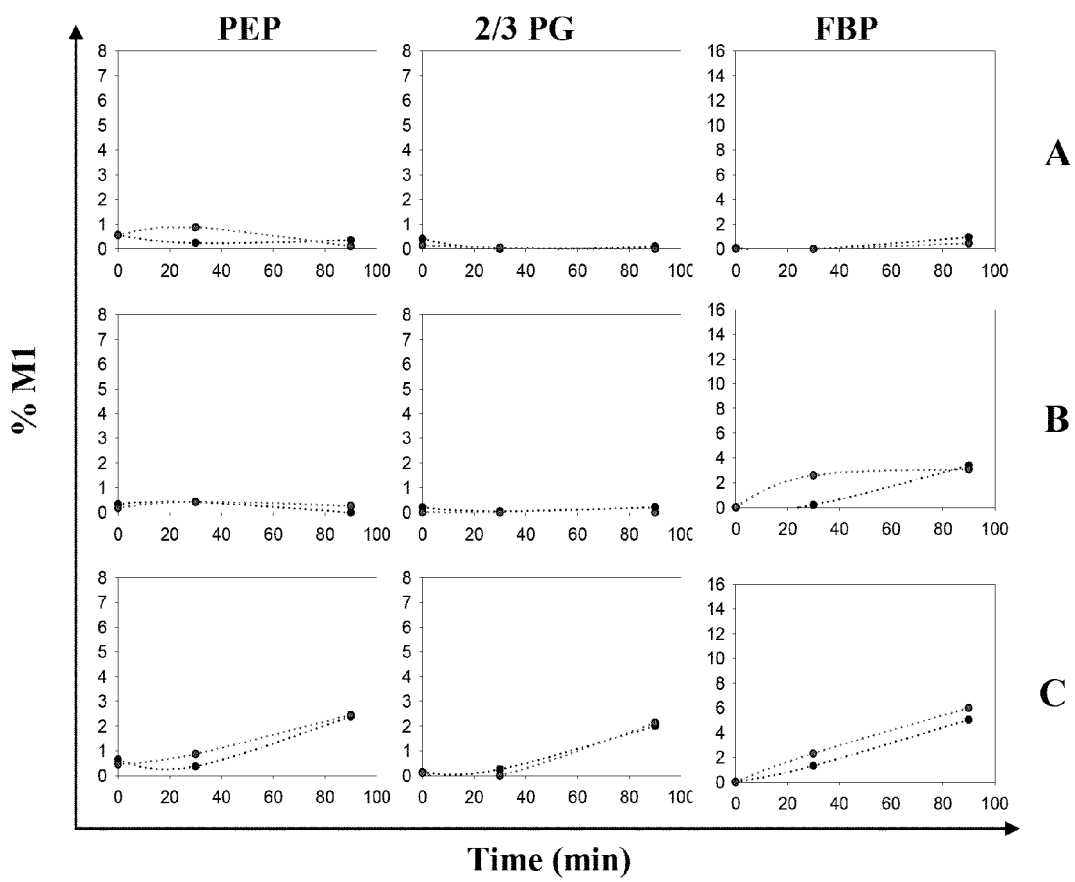

FIG. 13. % of mass isotopomer fraction M1 of different metabolites before (i.e. time zero point) and after (i.e 30 and 90 minutes time points) $^{13}C$-methanol addition. The two lines represent the results from two independent biological replicates. (A): *B. subtilis* 168 pHCMC04; (B): *B. subtilis* 168 AM3AhxlB-pHCMC04; (C): *B. subtilis* 168 AM3ABGFTPrpe-pHCMC04. PEP: phosphoenolpyruvate; ⅔ PG: 2- and 3-phosphoglycerate; FBP: fructose-bis-phosphate.

EXAMPLES

TABLE 1

| Bacterial strains and plasmids used in this study | | |
|---|---|---|
| Strain or plasmid | Description | Reference(s) or source |
| *B. methanolicus* MGA3 | Wild type strain ATCC53907 | ATCC |
| *B. methanolicus* PB1 | Wild type strain ATCC | ATCC |
| *E. coli* DH5α | General cloning host | Bethesda Research Laboratories |
| *E. coli* ER2566 | Carries chromosomal gene for T7 RNA polymerase | New England Bio labs |
| pHP13 | *E. coli*-*B. methanolicus* shuttle vector, Cm$^r$ | (Haima, Bron et al. (1987) Mol Gen Genet 209(2): 335-342; Jakobsen, Benichou et al. (2006) J Bacteriol 188(8): 3063-3072) |
| pGEM-T | *E. coli* cloning vector; Amp$^r$ | Promega |
| pLITMUS28 | *E. coli* cloning vector; Amp$^r$ | Promega |
| pET21a | *E. coli* expression vector, six-His tag, T7 promoter, Amp$^r$ | Novagen |
| pTMB1 | pLITMUS28 with the MGA3 mdh2 gene | This study |
| pTMB2 | pLITMUS28 with the MGA3 mdh3 gene | This study |

TABLE 1-continued

Bacterial strains and plasmids used in this study

| Strain or plasmid | Description | Reference(s) or source |
| --- | --- | --- |
| pET21a_MGA3-mdh | pET21a with the MGA3 mdh coding region under control of T7 and fused to six-His tag | This study |
| pET21a_MGA3-mdh2 | pET21a with the MGA3 mdh2 coding region under control of T7 and fused to six-His tag | This study |
| pET21a_MGA3-mdh3 | pET21a with the MGA3 mdh3 coding region under control of T7 and fused to six-His tag | This study |
| pET21a_MGA3-act | pET21a with the MGA3 act coding region under control of T7 and fused to six-His tag | This study |
| pET21a_PB1-mdh | pET21a with the PB1 mdh coding region under control of T7 and fused to six-His tag | This study |
| pET21a_PB1-mdh1 | pET21a with the PB1 mdh1 coding region under control of T7 and fused to six-His tag | This study |
| pET21a_PB1-mdh2 | pET21a with the PB1 mdh2 coding region under control of T7 and fused to six-His tag | This study |
| pET21a_PB1-act | pET21a with the PB1 act coding region under control of T7 and fused to six-His tag | This study |
| pET21a-nudF | pET21a with the *B. subtilis* nudF coding region under control of T7 and fused to six-His tag | This study |
| *B. subtilis* 168 | Wild type strain 168 | Kunst et al. (1997) Nature 390: 249-256 |
| pHB201 | *E. coli-B. subtilis* shuttle vector, Cm$^r$, Em$^r$ | Bron et al. (1998) J Biotech 64: 3-13 |
| pHCMC04 | *E. coli-B. subtilis* shuttle vector, Cm$^r$ | Nguyen et al. (2005) Plasmid 54: 241-248 |
| act-pHCMC04 | pHCMC04 with the *B. methanolicus* MGA3 act coding gene under control of the xylose-inducible promoter and fused to six-His tag | This study |
| mdh-pHCMC04 | pHCMC04 with the *B. methanolicus* MGA3 mdh coding gene under control of the xylose-inducible promoter and fused to six-His tag | This study |
| mdh2-pHCMC04 | pHCMC04 with the *B. methanolicus* MGA3 mdh2 coding gene under control of the xylose-inducible promoter and fused to six-His tag | This study |
| mdh3-pHCMC04 | pHCMC04 with the *B. methanolicus* MGA3 mdh3 coding gene under control of the xylose-inducible promoter and fused to six-His tag | This study |
| Amdh-pHCMC04 | pHCMC04 with the *B. methanolicus* MGA3 act and mdh coding genes under control of the xylose-inducible promoter and mdh fused to six-His tag | This study |
| Amdh2-pHCMC04 | pHCMC04 with the *B. methanolicus* MGA3 act and mdh2 coding genes | This study |

TABLE 1-continued

Bacterial strains and plasmids used in this study

| Strain or plasmid | Description | Reference(s) or source |
|---|---|---|
| | under control of the xylose-inducible promoter and mdh2 fused to six-His tag | |
| Amdh3-pHCMC04 | pHCMC04 with the *B. methanolicus* MGA3 act and mdh3 coding genes under control of the xylose-inducible promoter and mdh3 fused to six-His tag | This study |

Amp$^r$, ampicillin resistance;
Cm$^r$, chloramphenicol resistance

Materials and Methods

Biological Materials, DNA Manipulations, and Growth Conditions.

The bacterial strains and plasmids used in this study are listed in Table 1. *E. coli* DH5a was used as a standard cloning host, while *E. coli* ER2566 was used as host for recombinant expression of the MDH proteins, Act and NudF. The *E. coli* strains were generally grown at 37° C. in liquid or on solid Luria-Bertani (LB) medium (Sambrook (2001) Cold Spring Harbor Laboratory Press) supplemented with ampicillin (100 µg/ml) or chloramphenicol (10 µg/ml) when appropriate. Recombinant *E. coli* procedures were performed as described by Sambrook and Russell (2001; Cold Spring Harbor Laboratory Press). PCRs were performed by using the Expand High Fidelity PCR system (Roche Applied Science, Indianapolis, Ind.) and DNA sequencing was performed by Eurofins MWG Operon (Ebersberg, Germany, www.eurofinsdna.com). Isolation of *B. methanolicus* MGA3 and PB1 total DNA and recombinant production of MDH, Act and NudF proteins in *E. coli* ER2566 was performed as described previously (Brautaset et al., (2004) J Bacteriol 186(5): 1229-1238; Brautaset et al., (2010) Appl Microbiol Biotechnol 87(3): 951-964). Transformation of *B. methanolicus* MGA3 was performed by electroporation (Jakobsen et al., (2006) J Bacteriol 188(8): 3063-3072). *B. methanolicus* cells were grown at 50° C. in 100 ml of MeOH$_{200}$ medium containing 200 mM methanol, in Mann$_{10}$ medium containing 10 g/liter mannitol, or in SOBsuc medium (Jakobsen, Benichou et al. (2006) J Bacteriol 188(8): 3063-3072), and chloramphenicol (5 µg/l) was added as appropriate.

Construction of Expression Vectors pET21a_mdh-MGA3, pET21a_mdh2-MGA3, pET21a_mdh3-MGA3 and pET21a_act-MGA3:

Due to the high sequence similarity between mdh2 and mdh3 coding regions of MGA3, primers for PCR amplification and concomitant cloning were designed based on unique sequences representing the surrounding regions of the respective genes, and are as follows:

```
con16_rev:
                             (SEQ ID NO: 13)
5'-AACCATGGATGAGGAGGATGTTTGTATGAC-3'
and con18_rev:
                             (SEQ ID NO: 14)
5'-AACCATGGCAAACAAAGGGGATGTATGTATG-3';

con41_rev:
                             (SEQ ID NO: 15)
5'-AGGATCCCCTCCGTTTTGTCGTATTAC-3'
and con43_rev:
                             (SEQ ID NO: 16)
5'-TGGATCCTCTTCGTCTTTGGCGAATTAC-3'.
```

The respective DNA fragments were digested with NcoI+BamHI (recognition sites underlined in the primer sequences), and ligated into the corresponding sites of pLITMUS28 resulting in plasmid, pTMB1 carrying mdh2 and pTMB2 carrying mdh3. The cloned MDH genes in both plasmids were then sequenced. Next, the coding regions of mdh and act were PCR amplified from *B. methanolicus* MGA3 total DNA, and the coding regions of mdh2 and mdh3 were PCR amplified from plasmids pTMB1 and pTMB2, respectively, by using the following PCR primer pairs:

mdh_fwd-MGA3: 5'-<u>CATATG</u>ACAACAAACTTTTTCATTCC-3' (SEQ ID NO: 17) and mdh_rev-MGA3: 5'-<u>CTCGAG</u>CATAGCGTTTTTGATGATTTGTG-3' (SEQ ID NO: 18);

mdh2_fwd-MGA3: 5'-<u>CATATG</u>ACAAACACTCAAAGTGC-3' (SEQ ID NO: 19) and mdh2_rev-MGA3: 5'-<u>CTCGAG</u>CATCGCATTTTTAATAATTTGG-3' (SEQ ID NO: 20);

mdh3_fwd-MGA3: 5'-<u>CATATG</u>AAAAACACTCAAAGTGCATTTTAC-3' (SEQ ID NO: 21) and mdh_rev-MGA3: 5'-<u>CTCGAG</u>CATAGCGTTTTTGATGATTTGTG-3' (SEQ ID NO: 22);

act_fwd-MGA3: 5'-AAA<u>CATATG</u>GGAAAATTATTTGAGG-3' (SEQ ID NO: 23) and act_rev-MGA3: 5'-AAA<u>CTCGAG</u>TTTATTTTTGAGAGCCTCTTG-3' (SEQ ID NO: 24);

Underlined in the forward and reverse primers are restriction sites for NdeI and XhoI, respectively. The resulting PCR products mdh-MGA3 (1149 bp), mdh2-MGA3 (1163 bp), mdh3-MGA3 (1165 bp), and act-MGA3 (570 bp) were directly A/T-ligated into the general cloning vector pGEM-T, and the respective cloned inserts were verified by DNA sequencing. The resulting vectors were then digested with XhoI and NdeI and the inserts were ligated into the corresponding sites in frame with the six-His tag sequence of plasmid pET21a, yielding plasmids pET21a_mdh-MGA3, pET21a_mdh2-MGA3, pET21a_mdh3-MGA3, and pET21a_act-MGA3, respectively.
pET21a_mdh-PB1, pET21a_mdh1-PB1, pET21a_mdh2-PB1, and pET21a_act-PB1:

The coding regions of the mdh-PB1, mdh1-PB1 and mdh2 PB1 genes were PCR amplified from PB1 total DNA by using the following primer pairs:

```
mdh_fwd-PB1:
                                    (SEQ ID NO: 25)
5'-ATACATATGACGCAAAGAAACTTTTTCATTC-3'
and mdh_rev-PB1:
                                    (SEQ ID NO: 26)
5'-ATACTCGAGCAGAGCGTTTTTGATGATTTG-3';

mdh1_fwd-PB1:
                                    (SEQ ID NO: 27)
5'-ATACATATGACTAAAACAAAATTTTTCATTC-3'
and mdh_rev-PB1 (see above);

mdh2_fwd-PB1:
                                    (SEQ ID NO: 28)
5'-ATACATATGACAAACACTCAAAGTATATTTTAC-3'
and mdh2_rev-PB1:
                                    (SEQ ID NO: 29)
5'-ATACTCGAGCATAGCATTTTTAATAATTTGTATAAC-3'.
```

The three resulting PCR products mdh-PB1 (1164 bp), mdh1-PB1 (1164 bp) and mdh2-PB1 (1170 bp) were A/T-ligated into plasmid pGEM-T. The resulting plasmids were digested with XhoI and NdeI (restriction sites underlined in the primers) and ligated into the corresponding sites of plasmid pET21a, yielding plasmids pET21a_mdh-PB1, pET21a_mdh1-PB1, and pET21a_mdh2-PB1, respectively. The act-PB1 coding region was PCR amplified from PB1 total DNA by using the primer pair:

```
act_frw-PB1:
                                    (SEQ ID NO: 30)
5'-TTTTCATATGGGAAAATTATTTGAGGAAA-3'
and act_rev-PB1:
                                    (SEQ ID NO: 31)
5'-TTTTCTCGAGTTTATTTTTGAGAGCCTCTTG-3'.
```

The PCR product act-PB1 was digested with NdeI and XhoI (restriction sites underlined in the primers) and ligated into the corresponding sites of pET21a, resulting in plasmid pET21a_act-PB1.
pET21a_nudF:

The coding region of nudF was PCR amplified from *B. subtilis* 168 total DNA by using the following primer pair:

```
nudF-fwd:
                                    (SEQ ID NO: 32)
5'-TTTTCATATGAAATCATTAGAAGAAAAAACAATTG-3'
and nudF-rev:
                                    (SEQ ID NO: 33)
5'-TTTTCTCGAGTTTTTGTGCTTGGAGCGCTT-3'.
```

The resulting PCR product (572 bp) was A/T-ligated into pGEM-T and the cloned insert was verified by DNA sequencing. The resulting vector was digested with XhoI and NdeI (restriction sites underlined in the primers) and the insert was ligated into the corresponding sites of pET21a, resulting in plasmid pET21a_nudF.

All the constructed vectors were transformed into the expression host *E. coli* ER2566.

Affinity Purification of Recombinant Proteins

The six different MDH proteins, two different Act proteins and NudF were purified from cell extracts of the respective recombinant *E. coli* ER2566 strains by using affinity chromatography, essentially as described previously (Brautaset et al., (2010) Appl Microbiol Biotechnol 87(3): 951-964). Protein concentrations were estimated spectrophotometrically in a NanoDrop spectrophotometer, (Nano Drop Technologies, Wilmington, Del.) with molecular weight and extinction coefficient settings calculated for the MDHs, Act and NudF proteins (data not shown) using the Expasy Prot Param tool (expasy.org/tools/protparam.html) (Gasteiger et al. (2003) Nucleic Acids Res. 31(13): 3784-3788). The purity of the purified proteins were analyzed by sodium dodecyl sulfate-polyacrylamide gel electrophoresis (SDS-PAGE) (Sambrook and Russel, (2001) Cold Spring Harbor Laboratory Press), followed by visual inspection of the resulting images. The purified proteins were snap frozen in liquid $N_2$ and stored at −80° C. until they were thawed on ice and used in biochemical analyses.

Enzyme Assays

Alcohol dehydrogenase activities were measured spectrophotometrically essentially as described previously (Hektor, Kloosterman et al. (2002) Chem 277(49): 46966-46973) and the reaction mixture contained: 100 mM Glycine-KOH pH 9.5 (unless otherwise stated), 5 mM $MgSO_4$, 0.5 mM $NAD^+$ and 500 mM alcohol (methanol, ethanol, propanol, 1,3-propanediol, or butanol). $NAD^+$ was substituted with equal concentrations of $NADP^+$, $FMN^+$, and $FAD^+$, when indicated. The reaction mixture for measurements of formaldehyde reductase activity contained: 50 mM Potassium-phosphate buffer pH=6.7, 0.15 mM NADH, 1 mM DTT and 11.6 mM (0.1-116 mM) formaldehyde. The assay components were mixed in the cuvette and pre-warmed to 45° C., unless otherwise stated. The reactions were started by addition of 5-40 µg of the purified MDH proteins, and the production of NADH was monitored at 340 nm for 4 minutes. One unit of MDH activity was defined as the amount of enzyme needed to produce 1 µmol NADH per minute under the conditions described above. Purified Act (0.1-40 µg) or NudF (20 µg) proteins were added to the reaction mixtures as indicated in the text.

Biochemical Characterization In Vitro of Purified Enzymes

The purified MDH and Act proteins (20 µg) were used in the kinetic experiments performing the methanol dehydrogenase and the formaldehyde dehydrogenase assays essentially as described above. For determination of the $K_m$ for methanol ($K_{m,MeOH}$) and $V_{max}$, the $NAD^+$ concentration was maintained at a saturating level (0.5 mM or 0.15 mM), while the concentration of methanol was varied (0.1-2000 mM). For determination of the $K_m$ for $NAD^+$ ($K_{m,NAD+}$) and $V_{max}$, the methanol concentration was kept constant at a saturating level (500 mM), while the concentration of $NAD^+$ was varied (5-1000 µM). For determination of $K_m$ for formaldehyde ($K_{m,FA}$) and $V_{max}$, the NADH concentration was kept at saturating level (0.5 mM or 0.15 mM), while the concentration of formaldehyde was varied from (0.1-40 mM). Act (20 µg) was added to the reaction mixtures for determination of Kµ,MeOH and $V_{max}$ values in the presence of this activator, as indicated in the text. In general, the slopes of activity versus time were linear in the measured period (data not shown). $K_m$ and $V_{max}$ values were calculated by using nonlinear regression with the Microsoft Excel solver-tool to fit the measured data to the Michaelis-Menten equation, as described previously (Jakobsen et al., (2009) Appl Environ Microbiol 75(3): 652-661). The values obtained from the regression were then compared to the values obtained from Lineweaver-Burk and Hanes-Woolf plots to ensure that the global minimum, not a local minimum, had been found.

Isolation of Total RNA, cDNA Synthesis and Real-Time PCR

The real-time PCR experiments were performed essentially as described previously (Brautaset et al., (2010) Appl Microbiol Biotechnol 87(3): 951-964). Total RNA was isolated from MGA3 and PB1 cell cultures growing exponentially (OD600=1.0.) with mannitol or methanol as the sole carbon source, using the RNAqueous kit (Ambion). The concentration of RNA was determined in a NanoDrop spectrophotometer (Nano Drop Technologies, Wilmington, Del.), and the integrity of total RNA was assessed with an Agilent Bioanalyzer 2100 and the RNA 6000 Nano LabChip Kit (Agilent Technologies, Palo Alto, Calif.). cDNA was synthesized from the isolated total RNA using a first-strand cDNA synthesis kit (Amersham) according to the instructions of the manufacturer, and used as templates for the real-time PCR experiments. Real Time PCR analyses were preformed using the ABI PRISM 7700 Sequence Detection System with its default settings (Applied Biosystems, Foster City, Calif., USA). The PCR primers used were chosen with the assistance of the Primer Express 2.0 software (Applied Biosystems) and were as follows:

```
mdh-MGA3 fwd:
                                    (SEQ ID NO: 34)
5'-ATTCCACCAGCCAGCGTAAT-3'
and mdh-MGA3 rev:
                                    (SEQ ID NO: 35)
5'-CTTAGCTCCAATTTGCTTAAGTCTTG-3';

mdh2-MGA3 fwd:
                                    (SEQ ID NO: 36)
5'-GGATACATGTCAAACACTCAAAGTGC-3'
and mdh2-MGA3 rev:
                                    (SEQ ID NO: 37)
5'-TCTAGACACCATCGCATTTTTAATAATTTGG-3';

mdh3-MGA3 fwd:
                                    (SEQ ID NO: 38)
5'-GGATACATGTAAAACACTCAAAGTGC-3'
and mdh3-MGA3 rev:
                                    (SEQ ID NO: 39)
5'-TCTAGACACCATAGCATTTTTAATAATTTGGATG-3';

mdh-PB1 fwd:
                                    (SEQ ID NO: 40)
5'-TCCACCAGCTAGCGTAATTGG-3'
and mdh-PB1 rev:
                                    (SEQ ID NO: 41)
5'-AACCTGTGCCATGAAGAAATGC-3';

mdh1-PB1 fwd:
                                    (SEQ ID NO: 42)
5'-TCCATCATCCACTGTATTTGG-3'
and mdh1-PB1 rev:
                                    (SEQ ID NO: 43)
5'-ACCTGTGCTGTGAAGGAATGC-3';

mdh2-PB1 fwd:
                                    (SEQ ID NO: 44)
5'-CGTGAAGCTGGTGTGGAAGTATT-3'
and mdh2-PB1 rev:
                                    (SEQ ID NO: 45)
5'-TCCAAACCTTCTGCGACGTT-3'.
```

Relative quantization of the genes in question was performed by normalizing the results, relative to 16s RNA (endogenous control) and a calibrator sample, using a comparative Ct method (2-ΔΔCt method) as described previously (Heid, Stevens et al. (1996) Genome Res 6(10): 986-994; Jakobsen, Benichou et al. (2006) J Bacteriol 188(8): 3063-3072; Brautaset, Jakobsen et al. (2010) Appl Microbiol Biotechnol 87(3): 951-964). The relative differences in transcript levels of the three genes were determent by calculating the ΔCT values given as follows: mdh2 (Ct mdh2-Ct mdh) and the ΔCT value of mdh3 (Ct mdh3-Ct mdh). The primer efficiency of the three genes was tested prior to the other experiments preformed.

3D Modeling of the Deduced MDH Proteins

Structural models of the MGA3 Mdh and Mdh2 proteins were made using the fully automated protein structure homology-modeling server SWISS-MODEL (swissmodel.expasy.org/) (Peitsch (1995) Bio-Technology 13(7): 658-660; Arnold, Bordoli et al. (2006) Bioinformatics 22(2): 195-201; Kiefer, Arnold et al. (2009) Nucleic Acids Res 37 (Database issue): D387-392). Due to the high homology between the deduced primary structures of the MGA3 Mdh2 and Mdh3 proteins, no model search was performed for Mdh3. The gapped blast searches (Altschul et al (1997) J Mol Biol 215 (3): 403-410; Schäffer et al. (2001) Nucleic Acids Res. 29(14): 2994-3005) resulted in 9 common template hits with E values varying from $1 \cdot e^{-98}$ (pdb:3bfj, 1,3 propanediol oxidoreductase) to $1 \cdot e^{-17}$ (pdb:1oj7, *E. coli* K12 YQHD) for Mdh and from $1 \cdot e^{-112}$ (pdb:3bfj) to $2 \cdot e$-14 (pdb:1oj7) for Mdh2. 3D alignments of the template files using Deep view/Swiss pdb viewer (Guex and Peitsch (1997) Electrophoresis 18(15): 2714-2723) showed that they all had very similar folds and the structural models based on the 3bfj template, which had the highest amino acid similarity score both for Mdh and Mdh2, were chosen to represent Mdh and Mdh2. The Deep view/Swiss pdb viewer was also used to visualize the structural models of the MDHs.

Example 1

Genetic Organization of Methanol Dehydrogenase and Activator Protein Genes in *B. methanolicus* Wild-Type Strains MGA3 and PB1

In silico screening of the *B. methanolicus* MGA3 genome sequence (Heggeset et al., 2011) identified mdh encoded by plasmid pBM19, here denoted mdh-MGA3, and two more putative MDH encoding genes in the MGA3 genome, here denoted mdh2-MGA3 and mdh3-MGA3, distantly located on the chromosome. The mdh2-MGA3 and mdh3-MGA3 coding sequences were 96% identical to each other and 65% and 66% identical, respectively, to the mdh-MGA3 coding sequence. Primary sequence alignment of the deduced Mdh2-MGA3 and Mdh3-MGA3 polypeptides revealed that they are 96% identical to each other, and 61% and 62% identical, respectively, to Mdh-MGA3 (FIG. 2).

We have recently obtained fed-batch methanol fermentation results demonstrating that the two *B. methanolicus* wild-type strains MGA3 and PB1 are substantially different with respect to methylotrophic properties. Inspection of the PB1 genome sequence confirmed the presence of three different MDH-encoding genes and one act gene, analogous to MGA3. The mdh-PB1 gene located on plasmid pBM20 was 92% identical with the MGA3 mdh-MGA3 gene and the respective gene products displayed 93% primary sequence identity (FIG. 2). In contrast to MGA3, the sequences of the two chromosomal genes of PB1, denoted mdh1-PB1 and mdh2-PB1, were not very similar. The mdh1-PB1 gene encoded a putative Mdh1 protein with 92% primary sequence identity to the MGA3 Mdh protein while mdh2-PB1 encoded a putative Mdh2 protein with 91% and 92% primary sequence identity to the MGA3 Mdh2 and Mdh3 proteins, respectively. Based on these sequence analyses, it seems like MGA3 and PB1 possesses two sub-types of MDH encoding genes; the "mdh/mdh1" type and the "mdh2/mdh3 type". MGA3 has one mdh/mdh1 type gene (pBM19) and two mdh2/mdh3 type genes (chromosome), while PB1 has two mdh/mdh1 type genes (pBM20 and chromosome) and one mdh/mdh3 type gene (chromosome). The biological impact of these differences was further investigated below.

Example 2

3D Modeling Indicates that the *B. methanolicus* MDHs Belong to Type III Fe-NAD-Dependent Alcohol Dehydrogenase Super-Family The deduced MGA3 Mdh, Mdh2 and Mdh3 primary sequences were subjected to sequence comparisons with proteins in the databases using BLAST (Altschul, Gish et al. (1990) J Mol Biol 215(3): 403-410), indicating that they presumably belong to the type III alcohol dehydrogenases (ADHs) (de Vries, Arfman et al. (1992) J Bacteriol 174(16): 5346-5353), which is a super-family of iron-containing ADHs. The closest homolog of the MDHs with a known 3D structure was the 1,3-propanediol dehydrogenase from *Klebsiella pneumoniae* (PDB ID: 3BFJ, which displayed 46% primary sequence identity with Mdh and 52% primary sequence identity with Mdh2 and Mdh3. This 1,3-propanediol dehydrogenase is a type III Fe-NAD-dependent alcohol dehydrogenase that catalyzes the conversion of 3-hydroxypropionaldehyde into 1,3-propanediol (1,3-PD). The structure of the *B. methanolicus* C1 MDH has previously been analyzed by electron microscopy and it was concluded to be a decamer in which the 10 subunits were organized in two rings of 5 (Vonck, Arfman et al. (1991) J Biol Chem 266(6): 3949-3954). Interestingly, it was recently experimentally demonstrated that the 1,3-PD dehydrogenase had a similar quaternary structure. Based on this, we decided to use the information from the solved 3D structure of the 1,3-PD dehydrogenase to predict the 3D structure of the *B. methanolicus* MGA3 Mdh, to learn more about catalytic active sites in the NAD-dependent alcohol dehydrogenase. The primary amino acid sequence of MGA3 Mdh was sent to Swissmodel, and a model was constructed. The monomers of 1,3 PD dehydrogenase fold into two structural domains that are separated by a cleft. The N-terminal domain contains the binding site of the $NAD^+$ cofactor and the C-terminal domain includes the residues involved in iron binding. A conserved motif GGGSX2DX2K involved in $NAD^+$ cofactor binding was found in the N-terminal region of *B. methanolicus* C1 MDH. This motif is also present in *B. methanolicus* MGA3 Mdh, in position 95-104 and it is also found in the N-terminal region of the 1,3 PD dehydrogenase from *K. pneumoniae*. The 258-290 region of *B. methanolicus* C1 MDH contained several His residues, and was therefore predicted to be involved in metal binding. This is in good accordance with the findings in *K. pneumoniae* 1,3 PD dehydrogenase, were 4 residues responsible for the coordinating position of the iron metal were found. These residues are conserved and correspond to residues Asp193, His197, His262 and His276 in *B. methanolicus* MGA3 Mdh, and are most likely the ones responsible for binding of zinc in this enzyme. In conclusion, these data should indicate that the *B. methanolicus* MDHs belongs to type III Fe-NAD-dependent alcohol dehydrogenase, which was supported by the experimental results provided in the current study (see below).

Example 3

The Purified MDH Proteins from MGA3 and PB1 all Displayed NAD Dependent MDH Activity In Vitro The mdh-MGA3, mdh2-MGA3, mdh3-MGA3, mdh-PB1, mdh1-PB1, and mdh2-PB1 coding regions were PCR amplified and cloned into the *E. coli* vector pET21a, resulting in expression plasmids pET21a_mdh-MGA3, pET21a_mdh2-MGA3, pET21a_mdh3-MGA3, pET21a_mdh-PB1, pET21a_mdh1-PB1, and pET21a_mdh2-PB1, respectively. In the resulting vectors the recombinant genes are transcribed from the strong T7 promoter, and fused in-frame to a 6-His-tag coding sequence at their 3'-ends to simplify purification. The MGA3 and PB1 act genes and the analogous *B. subtilis* nudF gene were similarly cloned into pET21a, resulting in the plasmids pET21a_act-MGA, pET21a_act-PB1 and pET21a-nudF, respectively (Table 1). All constructed expression vectors were transformed into *E. coli* ER2566, and the resulting recombinant strains were cultivated in shake flasks for production of the respective recombinant proteins. The proteins were purified by affinity chromatography to above 95% purity as judged from SDS-PAGE (data not shown), and the Act and NudF proteins were stored for later use (see below).

The six purified MDH proteins were then assayed using methanol as substrate and the results showed that all enzymes are catalytically active (see FIG. 3). To rule out if these proteins can use alternative cofactors, the assays were repeated by substituting $NAD^+$ with $FAD^+$, $FMN^+$ and $NADP^+$. In all cases no catalytic activity was detected (data not shown), confirming that none of these alternative cofactors can be used by the MDHs under these conditions. These results demonstrated that both *B. methanolicus* strains MGA3 and PB1 have three different genes, one located on a plasmid and two located on the chromosome, that all encode active and NAD-dependent MDHs.

Example 4

All the MDHs have Broad Substrate Specificities and Different Alcohol Preferences In Vitro The purified MDH proteins where tested for catalytic activities by using several alternative alcohols, and all enzymes displayed activities on ethanol, propanol, butanol, pentanol, hexanol, isopropanol and 1,3-propanediol as substrates (FIG. 3). Surprisingly, the relative catalytic activities on most of these alternative substrates were substantially higher than with methanol for all six MDHs. The relative catalytic activities on each different alcohol varied substantially between the three MDHs, indicating different substrate preferences among these proteins. For example, the activities of the Mdh3-MGA3 and the Mdh2-PB1 enzymes with propanol were about 25 to 35-fold higher than their activity on methanol. Interestingly, these two enzymes displayed significantly higher catalytic activity than the remaining enzymes on all these substrates, under the conditions tested. All six enzymes also displayed formaldehyde and acetaldehyde reductase activities, which was further investigated below. Based on these data, it was tempting to classify these proteins as ADHs rather than MDHs, capable of catalyzing the conversion of a wide range of different primary and secondary alcohols to aldehydes or ketones.

Example 5

The MDH Proteins Displayed Similar pH and Temperature Optima In Vitro

In order to establish reliable assay conditions for comparative biochemical characterizations, the six MDH proteins were analysed for pH and temperature optima. Due to the much higher catalytic activities of all the MDHs on ethanol compared to methanol (see FIG. 3), we conducted these experiments with ethanol as the substrate to increase sensitivity of the data. The Mdh protein from *B. methanolicus* strain C1 has previously been reported to have a pH optimum of 9.5 (Kloosterman, Vrijbloed et al. (2002) J Biol Chem 277(38): 34785-34792), and the six purified MDHs (20 μg) were therefore tested for activity at pHs ranging between 8.5 and 10.5. All enzymes displayed the highest catalytic activity at pH between 9.5 and 10 (data not shown). Next, the MDHs were assayed at pH 9.5 for activity under temperatures ranging from 25° C. to 50° C., and the results showed that they all had temperature optima between 45° C. and 50° C. (FIG. 4). Based on these data all further MDH assays were run at pH 9.5 and 45° C.

Example 6

Mdh3-MGA3 and Mdh2-PB1 Display Higher Temperature Stabilities Compared to the Remaining MDHs In Vitro The heat stability of the six MDHs was tested by preincubation of the proteins at 45° C. and 60° C. and samples were taken at different time points for enzyme assays. As expected, all enzymes retained essentially all catalytic activity upon preincubations at 45° C. (FIG. 5). The catalytic activities of Mdh-MGA3, Mdh2-MGA3, Mdh-PB1 and Mdh1-PB1 were strongly reduced (up to 90%) upon preincubations at 60° C. for 6 minutes while this treatment presumably had only moderate negative effects on Mdh-MGA3 and Mdh2-PB1 catalytic activities (FIG. 5). A selection of the experiments was repeated in the presence of equal amounts of purified Act, and this had no effect on temperature stability for any of the MDHs (data not shown).

Example 7

All Six MDH Proteins are Catalytically Stimulated by Act In Vitro

Both the MGA3 and the PB1 genome sequences had only one act gene positioned on the chromosome similar to the act gene previously cloned from MGA3 (Brautaset, Jakobsen et al. (2004) J Bacteriol 186(5): 1229-1238). It was thus of interest to investigate if the respective Act proteins could stimulate catalytic activity of all MDH proteins in vitro. To establish reliable conditions, Mdh-MGA3 was first tested together with Act-MGA3 at different relative concentrations of the proteins (1:2-20:1), and using methanol as the substrate. Full activation was reached at a relative concentration of between 1:1 and 5:1 and no inhibition due to relative high activator concentrations was observed (data not shown). For further testing, equal concentrations of MDH and Act (1:1) were always used. Next, similar assays were performed with all six MDHs using methanol as substrate and the data showed that the MDH activities were induced 5 to 7-fold for the MGA3 MDHs (FIG. 6A) and 4 to 10-fold for the PB1 MDHs (FIG. 6B), in the presence of Act.

We then conducted similar analyses but by using ethanol as substrate and the results showed that the catalytic activities were increased 6 to 8-fold for the MGA3 MDHs (FIG. 6B) and 2 to 5-fold for the PB1 MDHs (FIG. 6B), in the presence of Act. Interestingly, when using formaldehyde or acetaldehyde as substrates the presence of Act caused no significant stimulation of catalytic activities for any of the MDHs (data not shown). Thus, Act increases the dehydrogenase versus the reductase activity ratio for all six MDH proteins in vitro.

Example 8

Mdh can Also be Catalytically Stimulated by the *B. subtilis* NudF Protein In Vitro Nudix hydrolase genes are found widespread in bacterial genomes and the *B. methanolicus* act gene is the only member of this family known to encode a regulator protein. The *B. subtilis* nudF gene product, NudF, displays 33% overall primary sequence identity to Act and it has been verified experimentally that NudF belongs to the ADP-ribose pyrophosphatase subfamily. NudF and Act are identical in residues documented to be important for substrate and/or inhibitor binding, metal binding, and the catalytic site. It was investigated whether NudF could substitute for Act in activating the *B. methanolicus* MDHs in vitro. Recombinant strain *E. coli* ER2566 (pET21a-nudF) was cultivated for recombinant production and concomitant purification of NudF. Mdh-MGA3 was chosen as model protein and tested together with NudF using ethanol as substrate as described above, and the results clearly demonstrated that Mdh activity was stimulated equally well (about 8-fold) with NudF as with Act under these conditions (Data not shown). This result shows for the first time that a heterologous Nudix hydrolases can function as an activator protein, and this should also have impact on our current understanding of the biological role of the diverse class of proteins.

Example 9

The MDHs have Similar $V_{max}$ and $K_{m,MeOH}$ Values In Vitro in Absence of Act The MDHs were subjected to kinetic characterizations to determine $V_{max}$ values and $K_m$ values, and to obtain biologically relevant data these experiments were conducted by using methanol as the substrate. The three MDH proteins were assayed for initial reaction rates under optimized assay conditions as described above and with varying methanol concentrations (see Materials and Method), and the data showed that they displayed similar and non-linear Michaelis-Menten kinetics. These results are in accordance with the analogous biochemically characterization of MDH from *B.*

*methanolicus* C1 (Hektor, Kloosterman et al. (2002) Chem 277(49): 46966-46973; Kloosterman, Vrijbloed et al. (2002) J Biol Chem 277(38): 34785-34792). They proposed that MDH in the non-activated state displays a Ping-Pong type of reaction mechanism in which the redox-active cofactor functions as a temporary electron deposit, while MDH in the activated state catalyzes a cofactor independent reaction which displays a ternary complex reaction mechanism. Km and Vmax values were calculated by using nonlinear regression with the Microsoft Excel solvertool to fit the measured data to the Michaelis-Menten equation. The $K_m$ values for methanol were similar and between 150 mM and 250 mM for the MGA3 MDHs and between 160 mM and 220 mM for the PB1 MDHs. The corresponding Vmax values were between 0.04 U/mg and 0.09 U/mg for the MGA3 MDHs and they were between 0.013 and 0.065 U/mg for the PB1 MDHs (Table 2). Together these data indicated that the kinetic constants for all the six MDHs are relatively similar under the conditions tested. We also chose to test the three MGA3 MDHs for initial reaction rates with varying the NAD concentrations, showing that they displayed linear Michaelis-Menten kinetics (data not shown). From non-linear fitting of the Michaelis-Menten equation, the $K_{m,NAD+}$ values were determined to be between 14 μM and 40 μM (Table 2).

TABLE 2

In vitro kinetic constants of purified *B. methanolicus* MDHs in the presence and absence of Act. Assays were performed at 45° C. and at pH 9.5.

| | MGA3: | | | | | |
|---|---|---|---|---|---|---|
| | Mdh | | Mdh2 | | Mdh3 | |
| Variable Substrate | $K_m$ (mM) | $V_{max}$ (U/mg) | $K_m$ (mM) | $V_{max}$ (U/mg) | $K_m$ (mM) | $V_{max}$ (U/mg) |
| Methanol | 200 | 0.08 | 150 | 0.04 | 250 | 0.09 |
| NAD+ | 14 μM | | 22 μM | | | 40 μM |
| Methanol + Act | 12 | 0.5 | 200 | 0.15 | 150 | 0.45 |
| Formaldehyde | 1 | 1.4 | 5 | 1.5 | 15 | 5 |

| | PB1: | | | | | |
|---|---|---|---|---|---|---|
| | Mdh | | Mdh1 | | Mdh2 | |
| Variable Substrate | $K_m$ (mM) | $V_{max}$ (U/mg) | $K_m$ (mM) | $V_{max}$ (U/mg) | $K_m$ (mM) | $V_{max}$ (U/mg) |
| Methanol | 220 | 0.03 | 168 | 0.013 | 164 | 0.065 |
| NAD+ | | | | | | |
| Methanol + Act | 13.9 | 0.2 | 2.3 | 0.056 | 36 | 0.24 |
| Formaldehyde | 2.5 | 0.45 | 11.5 | 0.53 | 1.3 | 1.12 |

Example 10

The $V_{max}$ Values for the MDHs are 4 to 6-Fold Increased in the Presence of Act Kinetic experiments were then preformed by using equal concentrations of MDH and Act in the reaction mixtures (20 μg MDH+20 μg Act). The $V_{max}$ values were increased 4-6-fold compared to in the single enzyme assays (Table 2) confirming that the catalytic activities of all six MDHs are stimulated by Act. These data are in agreement with those presented in FIG. 6.

Example 11

The $K_{m,MeOH}$ Values for Mdh-MGA3, Mdh-PB1 and Mdh1-PB1 are Substantially (Up to 70 Fold) Reduced in the Presence of Act Interestingly, the $K_{m,MeOH}$ was dramatically reduced (17-fold) to 12 mM for Mdh-MGA3 when Act was added to the reaction, while the corresponding $K_{m,MeOH}$ values for both Mdh2-MGA3 and Mdh3-MGA3 remained essentially the same as when tested without Act. For the three PB1 enzymes this was different. For Mdh-PB1 and Mdh1-PB1 the $K_{m,MeOH}$ values were substantially reduced (16-fold and 70-fold, respectively) in the presence of Act, and this value was moderately (4-fold) reduced by Act for Mdh2-PB1 (Table 2). Interestingly, the MGA3-Mdh, PB1-Mdh and PB1-Mdh1 proteins were by us listed into one MDH subgroup based on sequence alignments (see above), and the biological impact of these findings is discussed (see below).

Example 12

The MDHs Generally have Higher $V_{max}$ and Lower $K_m$ Values for Formaldehyde Compared to for Methanol The biological significance of MDH for methanol oxidation during methylotrophic growth is unambiguous, while the biological role of this enzyme as a formaldehyde detoxification system in the methanol consuming cells is less investigated. It was here demonstrated that all enzymes displayed both formaldehyde- and acetaldehyde reductase activities (see above), and we chose to characterize this property kinetically. By using formaldehyde as the substrate the $K_m$ values are 1 mM, 5 mM and 15 mM and the corresponding $V_{max}$ values are 1.4 U/mg, 1.5 U/mg and 5 U/mg for MGA3 proteins Mdh, Mdh2 and Mdh3 respectively (Table 2). For the PB1 proteins the $K_m$ values for formaldehyde were 2.5 mM, 4 mM and 1.3 mM, respectively, and the corresponding Vmax values were 0.45 U/mg, 0.53 U/mg and 1.12 U/mg, respectively. Together, these results show that all six MDHs generally have higher affinity and higher Vmax when formaldehyde is the substrate, compared to when methanol is the substrate.

Example 13

The Three mdh Genes are Transcribed at Different Levels in Exponentially Growing *B. methanolicus* Cells It was previously demonstrated mdh-MGA3 transcription is presumably very high in *B. methanolicus* cells and slightly up-regulated (about 3-fold) in cells growing on methanol versus on mannitol, while the act transcript levels were similar under both growth conditions (Jakobsen et al., (2006) J Bacteriol 188(8): 3063-3072). Here, all three MDH encoding genes from MGA3 were included in a similar analysis and the results showed that the relative transcription levels of mdh-MGA3 and mdh2-MGA3 were 2-fold and 3-fold higher on methanol compared to on mannitol. The transcript level of mdh3-MGA3 was essentially similar under the two different growth conditions. For mdh this result was somewhat different compared to previous data (Jakobsen et al., (2006) J Bacteriol 188(8): 3063-3072), and the reason for this is unknown. Interestingly, the respective Ct values obtained under standardized conditions for the three genes were highly different, with mdh-MGA3 displaying the by far lowest value indicating highest transcripts levels. The Ct mdh2-Ct mdh was found to be 8 and the Ct mdh3-Ct mdh was 14 (taking into consideration the about 100% primer efficiency in all these experiments, these numbers should imply that the mdh2-MGA3 and mdh3-MGA3 transcript levels at about 250-fold and 10.000 fold lower than the mdh transcript level, respectively, under the conditions tested).

The mdh2-MGA3 and mdh3-MGA3 coding sequences are 96% identical at the DNA level and to rule out any cross hybridization of the rt-PCR primers in these experiments, the respective rt-PCR primer pairs (see Materials and Methods) were tested towards plasmid DNAs, pTMB1 and pTMB2, carrying the respective mdh2 and mdh3 gene sequences. The results clearly show that no detectable PCR products were obtained when the mdh2 specific primers were used together with pTMB2 DNA, or alternatively when the mdh3 specific primers were used together with pTMB1 DNA template (data not shown). These data confirmed that the rt-PCR primers used for mdh2-MGA3 and mdh3-MGA3 are specific for their respective targets, confirming that the obtained data should be reliable.

A similar analysis of mdhs from PB1 was carried out and the results showed that mdh-PB1 and mdh2-PB1 transcript levels were essentially similar on mannitol versus methanol growth. Surprisingly, mdh1-PB1 transcript level on mannitol was 14-fold higher than on methanol, and the biological impact of this remained unknown. As for MGA3, we recognized that the relative transcript level of these three genes in PB1 was presumably very different, and the mdh-PB1 gene was transcribed to much higher levels than mdh1-PB1 and mdh2-PB1 (data not shown).

Example 14

Expression of *B. methanolicus* mdh Genes in *E. coli*

Construction of Expression Vectors

The genes coding for Mdh and the Mdh activator protein Act were amplified from pET21a-plasmids harboring genes from *B. methanolicus* strains MGA3 (mdh-MGA3, mdh2-MGA3, mdh3-MGA3 and act-MGA3) and PB1 (mdh-PB1, mdh1-PB1 and mdh2-PB1). The genes were then cloned either into the pSEVA424 plasmid (mdh genes) or in the pSEVA131 plasmid (act gene). For cloning of mdh-MGA3, mdh-PB1, mdh1-PB1 and act-MGA3, EcoRI and HindIII restrictions sites were used, while mdh2-MGA3, mdh2-PB1 and mdh3-MGA3 were cloned by using EcoRI and PstI restriction sites. The resulting expression vectors were transformed into electrocompetent wt *E. coli* K-12 (BW25113) and into *E. coli* K-12 (BW25113) with a deleted frmA gene. Expression Experiments For expression experiments, the cells were cultivated in either Luria-Bertani (LB) medium for in vitro assays or in M9 medium for in vivo assays both containing 20 μg/ml streptomycin for pSEVA424. When Act was co-expressed the medium was supplemented with 100 μg/ml ampicillin. Expression was induced when cells reached OD 0.5 (for in vitro tests) or OD 1 (for in vivo tests) by adding 0.1 mM IPTG (final concentration) for 6 hours. Cells were then harvested by centrifugation. For in vitro assays, crude cell extract was prepared by lysing the cells in a French press following ultracentrifugation. Alternatively, cells were resuspended in M9-medium without glucose for in vivo activity measurements.

Enzyme Assays

In vitro measurements of Mdh activity: For determination of Mdh activity in crude cell extracts, the Mdh dependent formation of NADH was monitored at 340 nm. The assays were performed either at 37° C. or 45° C. in prewarmed buffer solutions. The Mdh assay contained 10-20 μg enzyme, 50 mM $K_2HPO_4$-buffer, pH7.4, 2.5 mM MgCl and 0.5 mM of $NAD^+$ (final concentrations). After 5 min of preincubation, the reaction was started with 1 M of methanol (final concentration).

In vivo measurements of Mdh activity: For determination of Mdh activity in cell suspensions, cells were harvested after IPTG induction, washed and resuspended in M9-medium without glucose and IPTG. OD600 was set to 1 for normalization. The assay was performed at 37° C. or 45° C. in a shaking water bath. The assay was started by addition of 1 M methanol and subsequent measurement of accumulating formaldehyde in the supernatant resulting from the methanol dehydrogenase catalyzed oxidation of methanol. The calculated activities were based on the assumption that 1 l of an OD1 culture contains 0.3 g biomass of which 50% is protein.

Results

In vivo and in vitro activities of different Mdhs from *B. methanolicus* strains MGA3 and PB1 expressed recombinant in *E. coli* are summarized in Table 3 below. Act was cloned from *B. methanolicus* MGA3.

TABLE 3

In vivo and in vitro activities of different Mdhs from *B. methanolicus* strains MGA3 and PB1 expressed recombinantly in *E. coli*.

| | | In vitro [mU/mg] | | | | In vivo [mU/mg] | | | |
|---|---|---|---|---|---|---|---|---|---|
| | | 45° C. | | 37° C. | | 42° C. | | 37° C. | |
| | | +Act | −Act | +Act | −Act | +Act | −Act | +Act | −Act |
| MGA3 | Mdh | 1260 | 251 | 464 | 48 | 1 | 3 | 1 | 1 |
| | Mdh2 | 1910 | 310 | 672 | 59 | 11.3 | 45 | 9 | 32 |
| | Mdh3 | 867 | 113 | 327 | 21 | 24 | 31 | 11 | 24 |
| PB1 | Mdh | n.a. | 78 | n.a. | 26 | n.a. | n.a. | n.a. | 1 |
| | Mdh1 | n.a. | 219 | n.a. | 100 | n.a. | n.a. | n.a. | 0 |
| | Mdh2 | n.a. | 103 | n.a. | 33 | n.a. | n.a. | n.a. | 3 | n.a. = not available

In vitro, all Mdhs displayed higher activity at 45° C. than at 37° C. In addition the in vitro activities of the Mdhs from MGA3 was drastically increased when Act was co-expressed. In vivo the effect of the temperature was much smaller compared to the effect in vitro and the beneficial influence of Act was not detectable. MGA3-Mdh2 showed the overall highest activities both in vitro and in vivo among all genes tested. For the Mdhs from PB1, the picture looks different. Here the Mdh1, which is structurally closely related to Mdh from MGA3, shows the highest activity for most conditions tested. Surprisingly all 3 Mdhs from PB1 showed no or only very weak activity when tested in vivo. This finding is surprising because the in vitro activities at 37° C. look promising. The reason for this is unclear. Based on the available data, mdh2-MGA3 seems to be the overall best choice for maximized methanol dehydrogenase activity in *E. coli* tested both in vitro and in vivo.

Example 15

Expression of *B. methanolicus* mdh Genes in *B. subtilis*

Construction of Expression Vectors

All cloning steps were done using *E. coli* DH5α cells. The act-MGA3 gene was cloned from *B. methanolicus* MGA3 genomic DNA with a forward primer that contains the *B.* subtilis mntA ribosomal binding site (RBS) and a reverse primer that contains a short linker containing the SwaI and BglII restriction sites, and a His6-tag (FIG. 7A). The gene was inserted into the pHB201 and pHCMC04 plasmids using the SpeI and BamHI restriction sites. In the same way the mdh-MGA3 gene was cloned from the pBM19 plasmid from *B. methanolicus* MGA3 and the mdh2-MGA3 and mdh3-MGA3 genes were cloned from *B. methanolicus* MGA3 genomic DNA. These three genes were also ligated into the pHB201 and pHCMC04 plasmids.

For the construction of vectors for co-expression of act and the three different methanol dehydrogenase genes, the methanol dehydrogenase genes were PCR amplified with a forward primer that contains a stop codon and the *B. subtilis* mntA RBS and a reverse primer that contains a short linker containing the SwaI and BglII restriction sites (FIG. 7B). The respective genes were then end-digested with StuI and BglII and ligated into the SwaI and BglII sites of vector act-pHB201. In this way a stop codon is introduced after the act gene and the methanol dehydrogenase genes now contains the His6-tag. After sequencing the genes were transferred to the pHCMC04 plasmid (FIG. 7B) using the SpeI and BamHI restriction sites. Inserts were confirmed by sequencing.

Establishment of Recombinant *B. subtilis* Cells Expressing Methanol Dehydrogenase

*B. subtilis* 168 cells were transformed with the act-MGA3, mdh-MGA3, mdh2-MGA3, and mdh3-MGA3 expression plasmids, and the analogous vectors coexpressing each of the methanol dehydrogenase genes with the act-MGA3 gene. Positive colonies were picked from the plate and the plasmid was isolated and checked by restriction for positive clones. Colonies were picked from plate and grown overnight at 37° C. (250 rpm) and diluted to OD600=0.1 in 20 ml LB containing chloramphenicol (5 µg/ml). After 3 hrs of growth at 37° C. (250 rpm), 500 µl 40% xylose were added to the culture to induce expression. The culture was grown for another 3 hrs and samples of 2 ml were taken. The sample was spun down for 2 min, 11.000×g and the supernatant was removed. The pellet was resuspended in 300 µl Birnboim A for *B. subtilis* (10 mM Tris-HCl pH 8.0; 20% sucrose; 50 mM NaCl; 0.25 mg/ml lysozyme; protease inhibitor) and incubated at 37° C. for 30 minutes. The samples were stored at −80° C. before use. In addition, we took advantage of recombinant *E. coli* cells constructed in the project expressing mdh-MGA3, mdh2-MGA3, mdh3-MGA3 and act-MGA3 from the pET21a plasmid in the in vitro assays.

In Vitro Assays for Methanol Dehydrogenase Activity

The activities of the Mdh proteins were measured by following the formation of NADH spectrophoto-metrically. The reaction mixture contained:

100 µl Glycine-KOH (pH 9.5)
100 µl 5M Methanol (or 5M ethanol)
5 µl 1M $MgSO_4$
10 µl 50 mM $NAD^+$
10 µl sample
(10 µl *E. coli* act-pET21a lysate)
775 µl $H_2O$ The cuvets and reaction mixture without cell lysate were pre-incubated at 50° C. Formation of NADH was followed for 10 minutes at 340 nm at 50° C. The total activity was calculated by dividing the increase in absorption units per min by the extinction coefficient (6.23 $cm^{-1}$ $mm^{-1}$) and the total protein concentration in U/mg total protein. All assays were performed both by using methanol and ethanol as alternative substrates.

Results

All three genes tested, mdh-MGA3, mdh2-MGA3, and mdh3-MGA3 expressed active methanol dehydrogenases in host *B. subtilis*, while act-MGA3 alone expresses no detectable methanol dehydrogenase activity (FIG. 8). In general, the activities were significantly higher when using ethanol instead of methanol as the substrate, for all three genes tested (this is similar to what is observed when these enzymes have been purified from recombinant *E. coli* cells). In all cases, methanol dehydrogenase activities were significantly stimulated by Act. When the act and the methanol dehydrogenase genes are co-expressed from the same plasmid in *B. subtilis* 168, it seems that the Mdh2 protein is most active. However, we noticed that when Act is supplied from *E. coli* lysates, then the mdh-MGA3 genes is the most active. Thus, the mdh2-MGA3 gene—co-expressed together with act-MGA3—is the overall best choice for maximized methanol dehydrogenase activity in *B. subtilis* when tested in vitro.

Example 16

Methanol Incorporation into Genetically Engineered *C. glutamicum*

$^{13}C$ Labeling Experiments

For the labeling experiments we used the *C. glutamicum* delta ald strain that expresses Mdh2-MGA3 (pVWEx1-Mdh2), Hps and Phi (pEKEX3–Hps+Phi). As a negative control the *C. glutamicum* delta ald strain with the empty pEKEX3 plasmid was used. All *C. glutamicum* strains were grown on M9 medium containing (per liter) 3.48 g $Na_2HPO_4.12 H_2O$, 0.60 g of $KH_2PO_4$, 0.51 g of NaCl, 2.04 g of $NH_4Cl$, 0.10 g of $MgSO_4$, 4.38 mg of $CaCl_2$, 15 mg of $Na_2EDTA.2H_2O$, 4.5 mg of $ZnSO_4.7H_2O$, 0.3 mg of $CoCl_2.6H_2O$, 1 mg of $MnCl_2.4H_2O$, 1 mg of $H_3BO_3$, 0.4 mg of $Na_2MoO_4.2H_2O$, 3 mg of $FeSO_4.7H_2O$ and 0.3 mg of $CuSO_4.5H_2O$. For all the cultivation (M9 or LB), 1 mM of IPTG was used as inducer and 100 µg/ml of spectinomycin and 25 µg/ml of kanamycin were added in the medium as resistant markers. All the cultivations were performed at 30° C. Cell strains were plated from a glycerol stock on a LB agar plate (10 g/l of tryptone, 5 g/l of yeast extract, 10 g/l of NaCl, and 16 g/l agar) and grown afterwards on a LB liquid medium for 6 hours. The liquid pre-cultures containing M9 medium plus 3 g/l ribose were inoculated from the LB cultures at a final $OD_{600}$ of 0.6 for 12 hours. For the labeling experiments, the liquid cultures containing M9 medium were inoculated from the M9 (+ribose) cultures at a final $OD_{600}$ of 0.8. One cultivation sample was taken before addition of $^{13}C$-methanol (i.e. zero minute time point), then 40 mM of $^{13}C$-methanol was added and two cultivation samples were taken at 30 and 90 minutes. In order to quench the metabolic activity and extract the intracellular metabolites, cultivation samples were dispensed into a cold (−20° C.) solution of acetonitrile/methanol/0.1M formic acid (40/40/20 vol/vol). The labeling patterns of intracellular metabolites were measured using a Dionex ICS 2000 system (Dionex, Sunnyvale, USA) coupled to a triple quadrupole QTrap 4000 mass spectrometer (Applied Biosystems, Foster City, USA).

Results

As expected, no labeling in the mass isotopomer fraction Ml (i.e. molecules that have one carbon atom labeled) was detected in the wild-type strain after the $^{13}C$-methanol pulse (FIG. 9A). Significant label incorporation into metabolites was observed in the mutant expressing the two recombinant reactions from the RuMP pathway (Hps and Phi) and the NAD-dependent methanol dehydrogenase from *B. methan-* olicus MGA3 (Mdh2-MGA3) (FIG. 9B). While the labeling content was increased in the fructose-bis-phosphate and ribose-5-phosphate between 30 and 90 minutes, it stayed constant in the phosphoenolpyruvate and ⅔-phosphoglycerate. These data clearly demonstrate that the introduced methylotrophic pathway operates in vivo, leading to assimilation of methanol into central carbon metabolism.

It should be noted that in these and the further experiments described below, technical limitations meant that it was not possible to examine $^{13}$C-labelling of formaldehyde directly. However, by also expressing downstream RuMP pathway enzymes, it was possible to analyse incorporatation of the $^{13}$C into metabolites and thus indirectly detect assimilation of $^{13}$C-labelled methanol. Furthermore, the activity of the recombinantly expressed Mdh has been demonstrated in vitro in the above-described experiments, see for example Examples 3-6 above.

Example 17

Methanol Incorporation into Genetically Engineered E. coli

Results

We used metabolic labeling experiments to prove that Mdh, Hps and Phi are functional in living cells. Cells expressing all three proteins were fed with either $^{13}$C labeled methanol or $^{13}$C formaldehyde and incorporation of both C-1 compounds into several metabolites could be demonstrated.

For the experiments we used E. coli cells lacking the gene for the formaldehyde dehydrogenase (ΔfrmA) expressing mdh2, hps and phi or hps and phi alone from different pSEVA plasmids (424 and 131). All genes used for the experiments were derived from B. methanolicus MGA3. Precultures were obtained at 37° C. in optimized M9 minimal medium containing ribose as the sole carbon source. For the experiments the cells were transferred into fresh M9 medium without ribose. The experiments were started by the addition of either $^{13}$C-labelled methanol or formaldehyde. To check for incorporation, samples were taken at different time points, the metabolism was stopped by cold quenching and the samples were subsequently analysed by LC-MS analysis.

When methanol was added as the only substrate (FIG. 10A) labeling could be detected in several metabolites such as pentose 5-phosphates, hexose 6-phosphates, phosphoenolpyruvate and acetyl-CoA. More in depth analysis revealed that several metabolites necessary for the RuMP cycle, e.g. pentose 5-phosphates, showed incorporation of multiple labeled carbon compounds, indicating the operation of a complete functional cycle. When formaldehyde was used (FIG. 10B) the incorporation of labelled C-atoms occurred as well (in fact, it occurred faster relative to methanol incorporation suggesting that Hps and Phi work faster than Mdh or that the amount of C-5 precursor molecules needed for formaldehyde incorporation or the formaldehyde concentration produced from methanol was limited). In a control experiment using $^{13}$C-labelled methanol as the substrate, it was found that expression of Hps and Phi alone did not allow assimilation of the $^{13}$C-labelled methanol (data not shown).

The findings clearly show that the three introduced methylotrophic modules are functionally expressed. We also show that the expression of the three proteins lead to incorporation of methanol and formaldehyde into biomass via the established RuMP cycle. Using methanol or formaldehyde as a carbon source we could show that the assimilation of formaldehyde via Hps and Phi is much faster than the assimilation of methanol but might be limited by the availability of C5-precursor molecules.

Example 18

Methanol Incorporation into Genetically Engineered B. subtillis

Construction of Expression Vectors

All cloning steps were done using E. coli DH5a cells. The act-MGA3 gene was cloned from B. methanolicus MGA3 genomic DNA with a forward primer that contains the B. subtilis mntA ribosomal binding site (RBS) and a reverse primer that contains a short linker containing the SwaI and BglII restriction sites, and a His6-tag (FIG. 7A). The gene was inserted into the pHB201 plasmid using the SpeI and BamHI restriction sites. For the construction of vectors for co-expression of act, mdh3, hxlA, hxlB, glpX, fba, tkt, pfk and rpe, the genes were PCR amplified with a forward primer that contains a stop codon and the B. subtilis mntA RBS and a reverse primer that contains a short linker containing the SwaI and BglII restriction sites (FIG. 11). For amplification of act and mdh3 genomic DNA of B. methanolicus MGA3 was used, for the glpX, fba, tkt, pfk and rpe genes the pBM19 plasmid from B. methanolicus MGA3 was used, and for the hxlA and hxlB genes genomic DNA of B. subtilis 168 was used. The respective genes were then end-digested with StuI and BglII and ligated into the SwaI and BglII sites of the vector. The genes were sequentially introduced into the vector, thereby building up a synthetic operon of nine genes (FIG. 11). In this way, a stop codon is introduced after the each gene and the last gene in the synthetic operon now contains the His$_6$-tag. After the introduction of each gene in the synthetic operon, correct insertion was verified by sequencing. After sequencing the synthetic operons were transferred to the pHCMC04 plasmid (FIG. 7B) using the SpeI and BamHI restriction sites. Inserts were confirmed by sequencing.

Expression of RuMP Pathway Genes in B. subtilis 168

For establishment of recombinant B. subtilis cells expressing RuMP pathway enzymes, B. subtilis 168 cells were transformed with the vectors containing RuMP pathway genes (FIG. 7A). Positive colonies were picked from the plate and the plasmid was isolated and checked by restriction for positive clones. Colonies were picked from plate and grown overnight at 37° C. (250 rpm) and diluted to OD$_{600}$=0.1 in 100 ml MSR medium (25 g/l yeast extract, 15 g/l tryptone, 3 g/l K$_2$HPO$_4$, 1% glucose) supplemented with vitamins and chloramphenicol (5 μg/ml). After 3 hrs of growth at 37° C. (250 rpm), 1.25 ml 40% xylose was added to the culture to induce expression. The culture was grown for another 3 hrs and cells were spun down for 10 min, 4,000×g and the supernatant was removed. The pellet was washed with MSR medium and resuspended in 4 ml Birnboim A for B. subtilis (a lysis buffer containing 2 mM Tris-HCl (pH 7.4), 20% Sucrose, 50 mM NaCl, and 0.25 mg/ml lysozyme) and incubated at 37° C. for 30 minutes. The sample was centrifuged for 20 minutes at 13,000×g at 4° C. and the supernatant was used for HisTrap purification.

Purified protein fractions were combined and concentrated using Vivaspin (trade mark) columns (GE Healthcare). Purified proteins were visualized by SDS-PAGE and Coomassie staining (FIG. 12). We show that every protein that contains the His$_6$-tag was expressed from the synthetic operons (FIG. 11).

13C-Labeling Experiments

For the labeling experiments we used the *B. subtilis* strain that expresses Act, Mdh3, HxlA and HxlB and the strain that expresses Act, Mdh3, HxlA, HxlB, GlpX, Fba, Tkt, Pfk and Rpe. As a negative control the *B. subtilis* strain with the empty pHCMC04 plasmid was used. All *B. subtilis* strains were grown on M9 medium containing (per liter) 3.48 g $Na_2HPO_4.12H2O$, 0.60 g of $KH_2PO_4$, 0.51 g of NaCl, 2.04 g of $NH_4Cl$, 0.10 g of $MgSO_4$, 4.38 mg of $CaCl_2$, 15 mg of $Na2EDTA.2H_2O$, 4.5 mg of $ZnSO_4.7H2O$, 0.3 mg of $CoCl_2.6 H_2O$, 1 mg of $MnCl_2.4H_2O$, 1 mg of $H_3BO_3$, 0.4 mg of $Na_2MoO_4.2H_2O$, 3 mg of $FeSO_4.7H_2O$ and 0.3 mg of $CuSO_4.5H_2O$, 10 g of xylose (i.e. inducer) and 5 mg of chloramphenicol. All the cultivations were performed at 37° C. Cells strains were plated from a glycerol stock on a LB agar plate (10 g/l of tryptone, 5 g/l of yeast extract, 10 g/l of NaCl, and 16 g/l agar) containing 5 µg/ml of chloramphenicol and grown afterwards on a LB+chloramphenicol liquid medium for approximately 5 hours. The liquid pre-cultures containing M9 medium were inoculated from the LB cultures at a final $OD_{600}$ between 1.4 and 1.8. One cultivation sample was taken before addition of $^{13}$C-methanol (i.e. zero minute time point), then 40 mM of $^{13}$C-methanol was added and two cultivation samples were taken at 30 and 90 minutes. In order to quench the metabolic activity and extract the intracellular metabolites, cultivation samples were dispensed into a cold (−20° C.) solution of acetonitrile/methanol/0.1M formic acid (40/40/20 vol/vol). The labeling patterns of intracellular metabolites were measured using a Dionex ICS 2000 system (Dionex, Sunnyvale, USA) coupled to a triple quadrupole QTrap 4000 mass spectrometer (Applied Biosystems, Foster City, USA).

Results

As expected, no labeling in the mass isotopomer fraction M1 (i.e. molecules that have one carbon atom labeled) was detected in the wild type strain after the $^{13}$C-methanol pulse (FIG. 13A). In addition, no labeling was found in the mutant expressing the two recombinant reactions from the RuMP pathway (HxlA and HxlB), the activator protein (Act), and the NAD-dependent methanol dehydrogenase (Mdh3), but for which none of the genes from the pentose phosphate pathway (PPP) were overexpressed (FIG. 13B). However, when PPP genes were overexpressed in addition to the previous four genes, significant labeling incorporation was detected (FIG. 13C). These data clearly demonstrate that the introduced methylotrophic pathway operates in vivo, leading to assimilation of methanol into central carbon metabolism. These results also show that the supply of C-5 precursor molecules through the PPP is a bottleneck for methanol incorporation in *B. subtilis*. However, this can be alleviated by overexpressing genes encoding PPP-related enzymes.

The invention claimed is:

1. A recombinant nucleic acid vector comprising a nucleotide sequence encoding, a polypeptide having methanol dehydrogenase activity, the nucleotide sequence selected from the group consisting of:
   (i) a nucleotide sequence as set forth in any one of SEQ ID NOs: 1 (mdh2-MGA3), 3 (mdh3-MGA3), or 5 (mdh2-PB1);
   (ii) a nucleotide sequence having at least 90% sequence identity with a nucleotide sequence as set forth in any one of SEQ ID NOs: 1, 3 or 5:
   (iii) a nucleotide sequence which is degenerate with any one of the nucleotide sequences of SEQ ID NOs: 1, 3 or 5;
   (iv) a nucleotide sequence encoding a polypeptide whose amino acid sequence is set forth in any one of SEQ ID NOs: 2 (Mdh2-MGA3), 4 (Mdh3-MGA3) or 6 (Mdh2-PB1);
   (v) a nucleotide sequence encoding a polypeptide which has an amino acid sequence having at least 90% sequence identity with an amino acid sequence as set forth in any one of SEQ ID NOs: 2, 4 or 6; and
   (vi) a nucleotide sequence which is complementary to the nucleotide sequence of any one of (i) to (v).

2. A recombinant polypeptide having methanol dehydrogenase activity and comprising an amino acid sequence having at least 90% sequence identity with an amino acid sequence as set forth in any one of SEQ ID NOs: 2, 4 or 6.

3. The recombinant vector of claim 1, wherein the at least 90% sequence identity is at least 95% sequence identity.

4. The recombinant vector of claim 1, wherein the nucleotide sequence is operably linked to a heterologous expression control sequence.

5. A host microorganism comprising the recombinant vector of claim 1.

6. The host microorganism of claim 5, wherein the host microorganism is a bacterium selected from the genus *Escherichia, Corynebacterium* or *Bacillus*.

7. The host microorganism of claim 5, wherein the host microorganism is *E. coli, C. glutamicum, B. subtilis* or *B. methanolicus*.

8. A method for introducing exogenous alcohol dehydrogenase activity in a host microorganism, the method comprising;
   introducing the recombinant nucleic acid vector of claim 1 into the host microorganism; and
   growing the host microorganism under conditions in which the nucleotide sequence is expressed.

9. The recombinant polypeptide according to claim 2, wherein the amino acid sequence having at least 90% sequence identity with the amino acid sequence as set forth in any one of SEQ ID NOs: 2, 4 or 6 is an amino acid sequence having at least 91, 92, 93, 94, 95, 96, 97, 98 or 99% sequence identity with the amino acid sequence as set forth in any one of SEQ ID NOs: 2, 4 or 6.

10. The recombinant nucleic acid vector of claim 1, wherein the nucleotide sequence having at least 90% sequence identity with the nucleotide sequence as set forth in any one of SEQ ID NOs: 1, 3 or 5 is a nucleotide sequence having at least 91, 92, 93, 94, 95, 96, 97, 98 or 99% sequence identity with the nucleotide sequence as set forth in any one of SEQ ID NOs: 1, 3 or 5.

11. The recombinant nucleic acid vector of claim 1, wherein the amino acid sequence having at least 90% sequence identity with the amino acid sequence as set forth in any one of SEQ ID NOs: 2, 4 or 6 is an amino acid sequence having at least 91, 92, 93, 94, 95, 96, 97, 98 or 99% sequence identity with the amino acid sequence as set forth in any one of SEQ ID NOs: 2, 4 or 6.

12. The method of claim 8, wherein the host microorganism is *E. coli, C. glutamicum, B. subtilis* or *B. methanolicus*.

* * * * *